US008753866B2

(12) United States Patent
Penttila et al.

(10) Patent No.: US 8,753,866 B2
(45) Date of Patent: Jun. 17, 2014

(54) INCREASED PRODUCTION OF SECRETED PROTEINS BY RECOMBINANT EUKARYOTIC CELLS

(75) Inventors: Merja E. Penttila, Helsinki (FI); Michael Ward, San Francisco, CA (US); Huaming Wang, Fremont, CA (US); Mari J. Valkonen, Helsinki (FI); Markku La Saloheimo, Helsinki (FI)

(73) Assignee: Danisco US Inc., Palo Alto, CA (US)

( * ) Notice: Subject to any disclaimer, the term of this patent is extended or adjusted under 35 U.S.C. 154(b) by 212 days.

(21) Appl. No.: 12/639,921

(22) Filed: Dec. 16, 2009

(65) Prior Publication Data

US 2010/0221775 A1 Sep. 2, 2010

Related U.S. Application Data

(60) Division of application No. 10/663,450, filed on Sep. 15, 2003, now Pat. No. 7,662,584, which is a continuation of application No. 09/816,277, filed on Mar. 23, 2001, now abandoned, which is a continuation-in-part of application No. 09/534,692, filed on Mar. 24, 2000, now abandoned.

(51) Int. Cl.
*C12N 1/15* (2006.01)
*C12P 21/02* (2006.01)

(52) U.S. Cl.
USPC .................. 435/254.11; 435/70.1; 435/71.1

(58) Field of Classification Search
None
See application file for complete search history.

(56) References Cited

U.S. PATENT DOCUMENTS

| 5,010,182 | A |   | 4/1991  | Brake et al. ............... 536/27 |
|-----------|---|---|---------|-------------------------------------|
| 5,364,770 | A | * | 11/1994 | Berka et al. ............. 435/69.1  |
| 5,541,094 | A | * | 7/1996  | Anton et al. ............. 435/136   |
| 5,665,585 | A | * | 9/1997  | Torkkeli et al. ........... 435/203  |
| 5,874,276 | A |   | 2/1999  | Fowler et al. ............ 435/209   |

FOREIGN PATENT DOCUMENTS

| EP | 0 117 060   | 8/1984  |
|----|-------------|---------|
| EP | 0 362 179   | 4/1990  |
| GB | 2 211 504   | 7/1989  |
| WO | WO 90/13646 | 11/1990 |

OTHER PUBLICATIONS

Bailey et al. Biotechn. Appl. Biochem. 17:65-76, 1993.*
Zurbriggen et al., J. Biotech. 13:267-278, 1990.*
Ausubel et al., Current Protocols in Molecular Biology, (1987) Greene Publishing and Wiley Interscience, N. Y., (Supplemental through 1999).
Altschul el et al., "Basic Local Alignment Search Tool," J. of Mol. Biol., vol. 215, pp. 403-410, 1990.
D. Benson et al., "GenBank", Nucleic Acids Research, vol. 26, pp. 1-7, 1998.
Blond-Elguindi et al., "Affinity Panning of a Library of Peptides Displayed on Bacteriophages Reveals the Binding Specificity of BiP," Cell, vol. 75, pp. 717-728, Nov. 1993.
Chapman et al., "Translational attenuation mediated by an mRNA intron," Current Biology, vol. 7, pp. 850-859, Oct. 1997.
Cox et al., "A Novel Mechanism for Regulating Activity of a Transcription Factor that Controls the Unfolded Protein Response," Cell, vol. 87, pp. 391-404, Nov. 1996.
Cox et al., "Transcriptional Induction of Genes Encoding Endoplasmic Reticulum Resident Proteins Requires a Transmembrane Protein Kinase," Cell, vol. 73, pp. 1197-1206, Jun. 1993.
Dunn-Coleman et al., "Commercial Levels of Chymosin Production by *Aspergillus*," Bio/Technology, vol. 9, pp. 976-981, Oct. 1991.
Gething et al., "Cell-surface expression of influenza haemagglutinin from a cloned DNA copy of the RNA gene," Nature, vol. 293, pp. 620-625, Oct. 1981.
Gietz et al., "Improved method for high efficiency transformation of intact yeast cells," Nucleic Acids Research, vol. 20, p. 1425, 1992.
Gonzalez et al., "Mechanism of non-spliceosomal mRNA splicing in the unfolded protein response pathway," EMBO J., vol. 18, pp. 3119-3132, 1999.
Graham et al., "Characteristics of Human Cell Line Transformed by DNA from Human Adenovirus Type 5," J. Gen. Virol. vol. 36, pp. 59-72, 1977.
Hammond et al., "Quality control on the secretory pathway," Curr. Biol., vol. 7, pp. 523-529, 1995.
Harmsen et al., "Overexpression of binding protein and disruption of the PMR1 gene synergistically stimulate secretion of bovine prochymosin but not plant Thaumatin in yeast," App. Microbiol, Biotechnol. vol. 46, pp. 365-370, 1996.
Harris et al., "Molecular cloning and nucleotide sequence of cDNA coding for calf preprochymosin," Nucleic Acids Research, vol. 10, pp. 2177-2187, 1982.
Heinkoff et al., "Amino acid substitution matrices from protein blocks," Proc. Natl. Acad. Sci. USA, vol. 89, pp. 10915-10919, Nov. 1992.
Hess et al., "Cooperation of Glycolytic Enzymes," Adv. in Enzyme Reg., vol. 7, pp. 149-167, 1968.
Hitzeman et al., "Isolation and Characterization of the Yeast 3-Phosphoglycerokinase Gene (PGK) by an Immunological Screening Technique," J. of Biolog. Chem., Vol, 255, No. 24, pp. 12073-12080, 1980.
Holland et al., "Isolation and Identification of Yeast Messenger Ribonucleic Acids Coding for Enolase, Glyceraldehyde-3-phosphate Dehydrogenase, and Phosphoglycerate Kinase," Biochemistry, vol. 17, No. 23, pp. 4900-4907, 1978.

(Continued)

*Primary Examiner* — Nancy T Vogel
(74) *Attorney, Agent, or Firm* — Danisco US Inc.

(57) ABSTRACT

Described herein are methods for increasing the amount of protein secreted by a cell. In one case, a cell is provided which contains a heterologous nucleic acid encoding a protein having unfolded protein response modulating activity and a heterologous nucleic acid encoding a protein of interest to be secreted. In one case, the protein having unfolded protein response modulating activity is selected from the proteins selected from the group consisting of HAC1, PTC2 and IRE1. The protein of interest can be any secreted protein such as a therapeutic or an industrial enzyme. For example the protein can be selected from the group consisting of lipase, cellulase, endo-glucosidase H, protease, carbohydrase, reductase, oxidase, isomerase, transferase, kinase, phosphatase, alpha-amylase, glucoamylase, lignocellulose hemicellulase, pectinase and ligninase.

8 Claims, 34 Drawing Sheets

(56) References Cited

OTHER PUBLICATIONS

Howard et al., "The unfolded protein response signal transducer Ire1p promotes secretion of heterologous proteins in *Saccharomyces cerevisiae*," J. of Cell. Bioch. Suppl., No. 19B, 1995, p. 209.

Hsiao et al., "High-frequency transformation of yeast by plasmids containing the cloned yeast ARG4 gene," Proc. Natl. Acad. Sci. USA, vol. 76, pp. 3829-3833, Aug. 1979.

Jeenes et al., "Isolation and characterization of a novel stress-inducible PDI-family gene from *Aspergillus niger*," Gene, vol. 193, 1997, pp. 151-156.

Kaiser et al., "The use of Phage Lambda Replacement Vectors in the Construction of Representative Genomic DNA Libraries," IRL Press, Oxford, pp. 1-47, 1985.

Karlin et al., "Applications and statistics for multiple high-scoring segments in molecular sequences," Proc. Natl. Acad. Sci. USA, vol. 90, pp. 5873-5877. Jun. 1993.

Kawahara et al., "Endoplasmic Reticulum Stress-induced mRNA Splicing Permits Synthesis of Transcriptions Factor Hac1p/Ern4p that Activates the Unfolded Protein Response," Mol. Biol. of the Cell, vol. 8, pp. 1845-1862, Oct. 1997.

Keown et al., "Methods for Introducing DNA into Mammalian Cells," Methods in Enzymology, vol. 185, pp. 527-537, 1990.

McMillan et al., "The cellular response to unfolded proteins; intercompartmental signaling," Curr. Opinion in Biotechnology, vol. 17, pp. 540-545, 1994.

Mansour et al., "Disruption of the proto-oncogene int-2 in mouse embryo-derived stem cells: a general strategy for targeting mutations to non-selectable genes," Nature, vol. 336, pp. 348-352, Nov. 1988.

Mantei et al., "Rabbit β-globin mRNA production in mouse L cells transformed with cloned rabbit β-globin chromosomal DNA," Nature, Vol, 281, pp. 40-46, Sep. 1979.

Mather et al., "Establishment and Characterization of Two Distinct Mouse Testicular Epithelial Cell Lines," Biol. of Reprod. vol. 23, pp. 243-252, 1980.

Motenecourt et al., "Selective Screening Methods for the Isolation of High Yielding Cellulase Mutants of *Trichoderma reesei*," Amer. Chem. Society, vol. 181, pp. 289-301, 1979.

Mori et al., Palindrome with Spacer of One Nucleotide Is Characteristic of the cis-Acting Unfolded Protein Response Element in *Saccharomyces cerevisiae*, J. Biol. Chem., vol. 273, No. 16, pp. 9912-9920, 1998.

Mori et al., "A Transmembrane Protein with a cdc2$^+$/CDC28-Related Kinase Activity Is Required for Signaling from the ER to the Nucleus," Cell, vol. 74, pp. 743-756, Aug. 1993.

Mori et al., "Cloning of *Saccharomyces cervisiae* gene ERN4 encodin transcription factor UPRF responsible for the unfolded protein-response (UPR) pathway leading to the induction of ER-localized stress proteins," Chemical Abstracts, vol. 128, No. 26, Jun. 29, 1998 Columbus. Ohio, US.

Needleman et al., "A General Method Applicable to the Search for Similarities in the Amino Acid Sequence of Two Proteins," *J. Mol. Biol.*, vol. 48. pp. 443-453, 1970.

Pahl et al., "A novel signal transduction pathway from the endoplasmic reticulum to the nucleus is mediated by transcription factor NF-κB," *EMBO J.*, vol. 14, pp. 2580-2588, 1995.

Parlati et al., "*Saccharomyces cerevisiae* CNE1 Encodes an Endoplasmic Reticulum (ER) Membrane Protein with Sequence Similarity to Calnexin and Calreticulin and Functions as a Constituent of the ER Quality Control Apparatus," J. Biol. Chem., vol. 270, pp. 244-253, Jan. 1995.

Pearson et al., "Improved tools for biological sequence comparison," Proc. Natl. Acad. Sci. USA, vol. 85, pp. 2444-2448, Apr. 1988.

Penttila et al., "Expression of Two *Trichoderma reesei* Endoglucanases in the Yeast *Saccharomyces cerevisiae*," Yeast, vol. 3, pp. 175-185, 1987.

Penttila et al., "A versatile transformation system for the cellulolytic filamentous fungus *Trichoderma reesei*," Gene, vol. 61, pp. 155-164, 1987.

Punt et al., "Analysis of the role of the gene bipA, encoding the major endoplasmic reticulum chaperone protein in the secretion of homologous and heterologous proteins in black *Aspergilli*," Appl. Microbiol. Biotechnol, vol. 50, pp. 447-454, 1998.

Robinson et al., "Protein Disulfide Isomerase Overexpression Increases Secretion of Foreign Proteins in *Saccharomyces cerevisiae*," Bio/Technology. vol. 12, pp. 381-384, Apr. 1994.

Ruohonen et al., "Modifications to the ADH1 promoter of *Saccharomyces cerevisiae* for efficient production of heterologous proteins," *J. of Biotechnology*, vol. 39, pp. 193-203, 1995.

Ruohonen et al., "Efficient secretion of *Bacillus amyloliguefaciens* α-amylase cells by its own signal peptide from *Saccharomyces cerevisiae* host," Gene, vol. 59, pp. 161-170, 1987.

Saloheimo et al., "A novel, small endoglucanase gene, eg15, from *Trichoderma reesei* isolated by expression in yeast," Mol. Microbiol. vol. 13, pp, 219-228, 1994.

Saloheimo et al., "The protein disulphide isomerase gene of the fungus *Trichoderma reesei* is induced by endoplasmic reticulum stress and regulated by the carbon source," Mol. Gen. Genet. Vol, 262, pp. 35-45, 1999.

Sambrook et al., Molecular Cloning: A Laboratory Manual, New York: Cold Spring Harbor Press, 1989.

Shamu et al.,"Oligomerization and phosphorylation of the Ire1p kinase during intracellular signaling from the endoplasmic reticulum to the nucleus," EMBO J., vol. 15, pp. 3028-3039, 1996.

Sherman, F., "Getting started with Yeast," Methods in Enzymology, vol. 194, pp. 3-21, 1991.

Shoemaker et al., "Molecular Cloning of Exo-Cellobiohydrolase I derived from *Trichoderma reesei*," Bio/Technology, vol. 1, pp. 691-696, 1983.

Sidrauski et al., "The Transmembrane Kinase Ire1p Is a Site-Specific Endonuclease That Initiates mRNA Splicing in the Unfolded Protein Response," Cell, vol. 90, pp. 1031-1039, 1997.

Sidrauski et al., "tRNA Ligase Is Required for Regulated mRNA Splicing in the Unfolded Protein Response," Cell, vol. 87, pp. 405-413, 1996.

Smith, T., "Comparison of Biosequences," Adv. In App. Math. vol. 2, pp. 482-489, 1981.

Solingen et al., "Fusion of Yeast Spherplasts," J. of Bacteriol., vol. 130, pp. 946-947, 1977.

Stalbrand et al., "Cloning and expression in *Saccharomyces cerevisiae* of a *Trichoderma reesei* β-Mannanase Gene Containing a Cellulose Binding Domain," App Environ. Microbiol. vol. 61, pp. 1090-1098, 1995.

Urlaub et al., "Isolation of Chinese hamster cell mutants deficient in dihydrofolate reductase activity," Proc. Natl. Acad. Sci. USA, vol. 77, pp. 4216-4220. Jul. 1980.

Verduyn et al., "Effect of Benzoic Acid on Metabolic Fluxes in Yeasts: A Continuos-Culture Study on the Regulation of Respiration and Alcoholic Fermentation," Yeast, vol. 8, pp. 501-517, 1992.

Wach et al., "New Heterologous Modules for Classical or PCR-based Gene Disruptions in *Saccharomyces cerevisiae*," Yeast, vol. 10, pp. 1793-1808, 1994.

Ausubel et al., Current Protocols in Molecular Biology, (1987) Greene Publishing and Wiley Interscience, N.Y., (Supplemental through 1999).

Bowring, C. and Llewellyn, D. Differences in HAC1 mRNA Processing and Translation between Yeast and Mammalian Cells Indicates Divergence of the Eukaryotic ER Stress Response, Biochemcial and Biophysical Research Communications 287:789-800, 2001.

Clark, H. et al, The Unfolded protein Response Signal Transducer Ire1p Promotes Secretion of Heterologous Proteins in *Saccharomyces cereviseae*, J. Cell Bioch Supp., No. 19B, p. 209, 1995.

Dunn-Coleman et al., "Commercial Levels of Chymosin Production by *Aspergillus* " Bio/Technology, vol. 9, pp, 976-981, Oct. 1991.

Gething et al., "Cell-surface expression of nfluenza haemagglutinin from a cloned DNA copy of the RNA gene," Nature, vol. 293, pp. 620-625, Oct. 1981.

Gonzalez et al., "Mechanism of non-spliceosomal mRNA splicing in the unfolded protein response pathway," EMBO J., Vol, 18, pp. 3119-3132, 1999.

Harmsen et al., "Overexpression of binding protein and disruption of the PMR1 gene synergistically stimulate secretion of bovine prochymosin but not plant Thaumatin in yeast," App. Microbiol. Biotechnol. vol. 46, pp. 365-370, 1996.

(56) References Cited

OTHER PUBLICATIONS

Harris et al., "Molecular cloning and nucleotide sequence of cDNA coding for calf preprochymosin," Nucleic Acids Research, vol. 10, pp. 2177-2187, 1982.

Hitzeman et al., "Isolation and Characterization of the Yeast 3-Phosphoglycerokinase Gene (PGK) by an Immunological Screening Technique," J. of Biolog. Chem., vol. 255, No. 24, pp. 12073-12080, 1980.

Jeenes et al., " Isolation and characterization of a novel stress-inducible PDI-family gene from *Aspergillus niger*," Gene, vol. 193, 1997, pp. 151-156.

Karlin et al., "Applications and statistics for multiple high-scoring segments in molecular sequences," Proc. Natl. Acad. Sci. USA, vol. 90, pp. 5873-5877, Jun. 1993.

McMillan et al., "The cellular response to unfolded proteins: intercompartmental signaling," Curr. Opinion in Biotechnology, vol. 17, pp. 540-545, 1994.

Mantei et al., "Rabbit β-globin mRNA production in mouse L cells transformed with cloned rabbit β-globin chromosomal DNA," Nature, vol. 281, pp. 40-46, Sep. 1979.

Mori et al., "Cloning of *Saccharomyces cervisiae* gene ERN4 encodin transcription factor UPRF responsible for the unfolded protein-response (UPR) pathway leading to the induction of ER-localized stress proteins," Chemical Abstracts, vol. 128. No. 26, Jun. 29, 1998 Columbus, Ohio, US.

Needleman et al., "A General Method Applicable to the Search for Similarities in the Amino Acid Sequence of Two Proteins," *J. Mol. Biol.*, vol. 48, pp. 443-453, 1970.

Penttila et al., "Expression of Two *Trichoderma reesei* Endoglucanases in the Yeast *Saccharomyces cerevisiae*," Yeast vol. 3, pp. 175-185, 1987.

Punt et al., " Analysis of the role of the gene bipA, encoding the major endoplasmic reticulum chaperone protein in the secretion of homologous and heterologous proteins in black *Aspergilli*," Appl. Microbiol. Biotechnol, vol. 50, pp. 447-454, 1998.

Robinson et al., "Protein Disulfide Isomerase Overexpression Increases Secretion of Foreign Proteins in *Saccharomyces cerevisiae*," Bio/Technology, vol. 12, pp. 381-384, Apr. 1994.

Ruohonen et al., "Efficient secretion of *Bacillus amyloliquefaciens* α-amylase cells by its own signal peptide from *Saccharomyces cerevisiae* host," Gene, vol. 59, pp. 161-170, 1987.

Saloheimo et al., "A novel, small endoglucanase gene, eg15, from *Trichoderma reesei* isolated by expression in yeast" Mol. Microbiol. vol. 13, pp. 219-228, 1994.

Saloheimo et al., "The protein disulphide isomerase gene of the fungus *Trichoderma reesei* is induced by endoplasmic reticulum stress and regulated by the carbon source," Mol. Gen. Genet. vol. 262, pp. 35-45, 1999.

Schroder, M. et al, IRE1-and HAC1-independent Transcriptional Regulation in the Unfolded Protein Response of Yeast, Molecular Biology 49 (3): 591-606, 2003.

Shamu, C.E. Splicing: Hacking into the unfolded protein response, Current Biology 8: R121-R123, 1998.

Shamu et al., "Oligomerization and phosphorylation of the Ire1p kinase during intracellular signaling from the endoplasmic reticulum to the nucleus," EMBO J., vol. 15, pp. 3028-3039, 1996.

Urlaub et al., "Isolation of Chinese hamster cell mutants deficient in dihydrofolate reductase activity," Proc. Natl. Acad. Sci. USA, vol. 77, pp. 4216-4220, Jul. 1980.

Valkonen et al, Effects of Inactivation and Constitutive Expression of the Unfolded-Protein Response Pathway on Protein Production in the Yeast *Saccharomyces cerevisiae*, Applied and Environmental Microbiology 69(4):2065-2072, 2003.

Wang et al., 2000, Current Genetics, In Press.

Welihinda et al., "Protein Serine/Threonine Phosphatase Ptc2p Negatively Regulates the Unfolded-Protein Response by Dephosphorylating Ire1p Kinase," Mol. and Cell. Biol., vol. 18, pp. 1967-1977, 1998.

Wiertz et al., "Sec61-mediated transfer of a membrane protein from the endoplasmic reticulum to the proteasome for destruction," Nature, vol. 384, pp. 432-438, 1996.

Databased EMBL EBI; Oct. 20, 1998 "*A. nidulans* cDNA clone z2g07al.r1".

Databased EMBL EBI; Feb. 8, 1998 "*A. nidulans* cDNA clone c7a10a1.f1".

Databased EMBL EBI; Feb. 8, 1998 "*A. nidulans* cDNA clone i2c04a1.f1".

Databased EMBL EBI; May 20, 1998 "*A. nidulans* cDNA clone v1h01a1.r1".

Databased EMBL EBI; Nov. 8, 1999 "*Metarhizium anisopliae* mRNA; expressed sequence tog Ma#1855".

Databased SWALL EBI; Nov. 1, 1995 (Nov. 1, 1999) "HAC1 of *S. cervisiae*".

Databased SWALL EBI; Nov. 1, 1995 (Nov. 11, 1999) "Protein phosphatase 2C homlog 2 (PP2C-2) of *S. pombe*".

Databased SWALL EBI; Oct. 1, 1993 "Ser/Thr protein kinase IRE1 precusor of *S. cerevisiae*".

\* cited by examiner

```
GCAGAGGCCACTCTGTCCTCTTCTGCCTGACTCATCACTCCTGACACAGCATCACCAAGGGGAAGCACTGCACTGGACACAGCCACGCC          90
GCTTCCCACTGACTCATTGGGACTGGCGCCGTTGCCTGTCATGACTGTTCGCATCGTCATCAACGATGACTCGTCATCGACTGCTTCGCTT        180
TGATTGCTTCTCCTCCACTCCTCTCCTCCCGTCCCTTTCGAAGAGAAACAGTTGGTCGACGTCACAAGCACATTCACAAAAATCAAACAACATATCCCCAT   270
CGAAAAAACCAACTCCGTCCCTTTCGAAGAGAAACAGTTGGTCGACGTCACAAGCACATTCACAAAAATCAAACAACATATCCCCAT              360
CTTTCATATACCACACGCTTATGCAGTGAGTGAGAGCATCGTCATAATCAACACATCAGTCAAAGCGAACTGCGCTCGG                     450
CAACACGACACGGCAGGCAACATGGCGTTCCAGCAGTCGTCTCCCCTCGTCAAGTTTGAGGCCTCTCCCGCCGAATCCTTCCTCTCCGCC          540
                   M  A  F  Q  Q  S  S  P  L  V  K  F  E  A  S  P  A  E  S  F  L  S  A
CCCGGCGACAACTTCACATCCCTCTTCGCCGACTCAACACCCTTAACCCTCGGGACATGATGACCCCTGACAGCGTCGCCGAC                 630
 P  G  D  N  F  T  S  L  F  A  D  S  T  P  S  T  L  N  P  R  D  M  M  T  P  D  S  V  A  D
ATCGACTCTCGCCTGTCCGTCATCCCCGAATCACAGGACGCGGAAGATGACGAATCACACTCCGCTACCGCACCCTCTACCTCA               720
 I  D  S  R  L  S  V  I  P  E  S  Q  D  A  E  D  D  E  S  H  S  T  S  A  T  A  P  S  T  S
GAAAAGAAGCCCGTCAAGAAGAGGAAATCATGGGGCCAGGTTCTTCCTGAGCCCAAGACCAACCTCCCTCCTCGgtatgtcactgcaaca          810
 E  K  K  P  V  K  K  R  K  S  W  G  Q  V  L  P  E  P  K  T  N  L  P  P  R
cggctcaacttgatacaaacttgcatcctaaccaaacgttactgtagAAAAACGTGCAAAGACGGAAGATGAAAAGGAGCAGCGCCGTCGA         900
                                                K  R  A  K  T  E  D  E  K  E  Q  R  R  V  E
GCGTGTTCTCCGCAACGCGCCGGCGCCGCGAGCGCAAGGCTCTCGAGGTCGAGGCTCGAAGCGCAACAAGGAGCTCGAGAAGCGCAACAAGGAGCT    990
 R  V  L  R  N  R  R  A  A  Q  S  S  R  E  R  K  R  L  E  V  E  A  L  E  K  R  N  K  E  L
CGAGACGCTCCTCATCAACGTCCAGAAGACCAACCTGATCCTCGTCGAGGAGCTCAACCGCTTCAGGCGTCAGCTCAGCAGCGGCGTCGTCACCCG   1080
 E  T  L  L  I  N  V  Q  K  T  N  L  I  L  V  E  E  L  N  R  F  R  R  S  S  G  V  V  T  R
```

FIG. 7A

```
CTCGTCCTCCCCCCTCGACTCTCTCCAGGACAGCATCACTCTCTCCCAGCAACTCTTTGGCTCGCGGGATGGCAAACCATGTCCAACCC  1170
 S  S  S  P  L  D  S  L  Q  D  S  I  T  L  S  Q  Q  L  F  G  S  R  D  G  Q  T  M  S  N  P

CGAGCAGTCCTTGATGGACCAGATCATGAGATCTGCCGCTAACCCTACCGTTAACCCGGCCTCTCTTCCCCCTCCCCCATCTC  1260
 E  Q  S  L  M  D  Q  I  M  R  S  A  A  N  P  T  V  N  P  A  S  L  S  P  S  L  P  P  I  S

GGACAAGGAGTTCCAGACCAAGGAGGAGGACGAGGAGCAGGCCGACGAAGAGATGGAGCAGACATGGCACGAGACCAAAGAAGC  1350
 D  K  E  F  Q  T  K  E  E  D  E  E  Q  A  D  E  E  E  M  E  Q  T  W  H  E  T  K  E  A

CGCCGCCGCCAAGGAGAAGAACAGCAAGCAGTCCCGCGTCTCCACTGATTCGACACAGCGTCCTGcagagatgttgtcgacccgcAGTG  1440
 A  A  A  K  E  K  N  S  K  Q  S  R  V  S  T  D  S  T  Q  R  P  A                           V TCAATCGGTGGTGGAGATGCCGCTGTCCCTGTTCTCTTCCAGAACCTGGGCTGAACTCCGGGCCAAACTGCCTTGGCCTTGGCCTTGGATGATGGT  1530
 S  I  G  G  D  A  A  V  P  V  F  S  D  D  A  G  A  N  C  L  G  L  D  P  V  H  Q  D  D  G CCCTTTCAGCATCGGCCATTCTTTCGGCCTGTCAGCGCAGATGCAGATCGCTATCTCCTGAAAGCCAACTTCTGCCTTCGCCCAAC  1620
 P  F  S  I  G  H  S  F  G  L  S  A  A  L  D  A  D  R  Y  L  L  E  S  Q  L  L  A  S  P  N GCCTCAACTGTTGACGACGATTATCTGGCTGGTTCTGACTCCGACTAGACTTCGACATCAAC  1710
 A  S  T  V  D  D  D  Y  L  A  G  D  S  A  A  C  F  T  N  P  L  P  S  D  Y  D  F  D  I  N GACTTCCTCACAGACGACGCAAACCACGCCTATGACATTGTGGCAGCGAGCAACTATGCCGCTGCCGAGCTGGACCTCGAG  1800
 D  F  L  T  D  D  A  N  H  A  A  Y  D  I  V  A  A  S  N  Y  A  A  A  D  R  E  L  D  L  E ATCCACGACCCTGAGAATCAGATCCCGTTCGCGACATTCCCTTCGCATCAGCAGCCCCAGTCGGCGGTCTCTCATGGATGCGACGATGGCGGC  1890
 I  H  D  P  E  N  Q  I  P  S  R  H  S  I  Q  Q  P  Q  S  G  A  S  S  H  G  C  D  D  G  G ATTGCGGTTGGTGTCTGAGGGATCCGGGGACGCGACGATCGGGGCTCCGAGTCTTGTGCGACGCGGGCGACTGCGAGCTGGAACG  1980
 I  A  V  G  V
```

FIG. 7B

```
GTGCCTACGCAGCGGTGACCTTGCCGTGTCTCGAGAAGTCCTCATCACCCTGTGTGGGCCGTGAAGGTGGAGGAGGAGGATTCGCCTGAG 2070

GCAGCACAAGAAGCAGGCCGCGGCTCTCGACCCCGAGAAGCGCGCCTCCTTGGCAGACAAGAAGAACCGACAACAACAACAACAACAACA 2160

CCAGTATCAGATTCCTTCGTTTTCAAAATAGTTAGCATATGTGGTTTTTTAATGGGCAATGGGGCCGATGGCAACACGGTAGAGGCAACA 2250

AGGGTTTGACTACACCTCCCAAAGGGATACGGCGCACAGCGAGGTTAATGACAAGGCTAAGATGGGCCTTTTTTTTTATGATATGAGAAC 2340

CTCTTCATCTCCCTTTACACTTCTCTAGATGGTAGTGATGATATACTGTACCAAAATACAACGTCTACCTAGTGCT 2418
```

*FIG. 7C*

```
GCCATCCTTGGTGACTGAGCCCCAAACACTTTCACTGGTCGGGATAGTAGCCTCTGGCTTCGATTCGCTATGACACCGTGGCCTCTGTCCT    90

AAGTGACTCAGGCAAGGCAATCCCAGTTCCAACTTCGCAACCTCATCAACCACCTGTCCGTCTAGTTGCAGTTATCAGACT    180

TGAGTTGTATGAAATCAGACAGACCGGTTTCCGCAGTGAAATGGAGGACGCTTTCGCAAACTCTTTGCCTACTACCCCGTCATTGGAGG    270
  M  K  S  A  D  R  F  S  P  V  K  M  E  D  A  F  A  N  S  L  P  T  T  P  S  L  E

TTCCTGTGCTCACTGTCTCCCGGCTGACACATCTCTTGGCTGTCAGACAAAGTGGTGGCTCAGACAAAGCCTGAGGAGAAGAAGCCAGCGA    360
 V  P  V  L  T  V  S  P  A  D  T  S  L  R  T  K  N  V  V  A  Q  T  K  P  E  E  K  K  P  A

AGAAAAAGAAAGTCCTGGGGCCAGAATTACCAGTTCCCAAGACAAACTTACCTCCAAGgtgtgtgatacctcaagagtcaactcctact    450
 K  K  K  S  W  G  Q  E  L  P  V  P  K  T  N  L  P  P  R cctgctaataactaccacagAAAACGCGCTAAGACAGAAGATGAGAAGAGCAGCCGCCGATTGAGCGCCGGAGTTCTTCGCAACCGGCAGCC    540
                     K  R  A  K  T  E  D  E  K  E  Q  R  R  I  E  R  V  L  R  N  R  A  A GCACAAACCTCTCGCGAGCGCAAGAGACTTGAAATGGAGAAGTTAGAAAGCGAGAAGATTGATATGGAACAAAACCAGTTCCTTCTT    630
 A  Q  T  S  R  E  R  K  R  L  E  M  E  K  L  E  S  E  K  I  D  M  E  Q  N  Q  F  L  L CAGCGTCTCGCCCAGATGGAGGCTGAGAACAACCGTTTAAGTCAGCAAGTTGCTCAGTCAGGTTGCCCAGAGGTTCGGGGATCCCGCCACAGC    720
 Q  R  L  A  Q  M  E  A  E  N  N  R  L  S  Q  Q  V  A  Q  L  S  A  E  V  R  G  S  R  H  S ACTCCAACTTCCAGTTCCCCGCGTCAGTTTCGCCAACTCTTCATCTCTGGCTGAGTCCCCGATTTGACACAACATCCT    810
 T  P  T  S  S  P  A  S  V  S  P  T  L  T  P  T  L  F  K  Q  E  G  D  E  V  P  L  D  R ATCCCTTTTCCAACTCCAGTTCCCCAACTCTTAAGCCTTCAGTCGTAAGGAGATGAGTTCCTGACCGC    900
 I  P  F  P  S  V  T  D  Y  S  P  T  L  K  P  S  S  L  A  E  S  P  D  L  T  Q  H  P GCagcgatgttgtgcgacctgcagtgtcagtcggCGGGGCTCGAAGGAGATGAAAGTGCCCTCACGCTTTTCGACTTCGGAGCCATTA    990
 A                                  V  S  V  G  G  L  E  G  D  E  S  A  L  T  L  F  D  L  G  A  S  I
```

FIG. 8A

```
AGCATGAGCCTACACATGACCTTACAGCTCCTCTTTCTGACGATGATTCATCCCTTGAGTCAGATT  1080
 S  M  S  L  H  M  T  L  Q  L  L  F  L  T  M  I  S  L  E  S  D
 K  H  E  P  T  H  D  L  T  A  P  L  S  D  D  D  F  R  R  L  F  N  G  D  S  S  L  E  S  D

CTTCACTCCTTGAAGACGGGTTCGCTTTTGACGTTCTCGACTCAGGAGATTTATCAGCATTCCATTTGATTCATGGTTGATTTTGACA  1170
 S  S  L  E  D  G  F  A  F  D  V  L  D  S  G  D  L  S  A  F  P  F  D  S  M  V  D  F  D

CCGAGCCTGTCACCCTCGAAGATCTCGAGCAAACCAACGGCCTTTCGGATTCAGCTTCTTGCAAGGCCTGTAGCTTGCAACCCAGCCATG  1260
 T  E  P  V  T  L  E  D  L  E  Q  T  N  G  L  S  D  S  A  S  C  K  A  A  S  L  Q  P  S  H

GCGCGTCCACTTCGCGATGCCAGCGGGCAGGCCAGTGCAGCATTGCAGCTGCGTGAGAGGTTTTGACGGAAGACCGTCTGGTTCCGATGTT  1350
 G  A  S  T  S  R  C  D  G  Q  G  I  A  A  G  S  A

GTAGAGGGTCGATGGAGCTGGGAATCCTTGTTAACGCTAGCGTCGGCGATAAATCTTCTTGAGAAACCGGAGCGACGAAGAAGAACCTTG  1440

AGGGTCTTGATTCGTTAAAGCGGGGTCGGCGTATTGATTCGGGAAGCGGTACAGGGTCATACGGAGTTCACGGAGTTCAACTAGCCCA  1350

AGAGAGGCGTTGACGTCTCGGAGAAAGGGCTTATGATAATTGTATATTAGCGTGTCCACTATTCAATGTAAGAGCGAGCAATTG  1615
```

FIG. 8B

```
T. reesei     MAFQQSSPLVKFEASPAESFLSAPGDNFTSLFADSTPSTLNPRDMMTPDS  50
A. nidulans   MKSADRFSPVKMEDA-------------------FANSLPTTPSLEVPVLTVS  34
              *       **  **   .                 ** * *.*     .  *

T. reesei     VADIDSRLSVIPESQDAEDDESHSTSATAPSTSEKKPVKKRKSWGQVLPE 100
A. nidulans   PADTSLRTKNVVAQTKPE----------------EKKPAKKRKSWGQELPV  69
              ** *  *                *          **** ******** **

T. reesei     PKTNLPPRKRAKTEDEKEQRRVERVLRNRRAAQSSRERKRLEVEALEKRN 150
A. nidulans   PKTNLPPRKRAKTEDEKEQRRIERVLRNRAAAQTSRERKRLEMEKLESEK 119
Yeast         *KSTLPPRKRAKTKEEKEQRRIERILRNRRAAHQSREKKRLHLQYLERKC  71
              *. ********* .****** **.**** **  ***.***  .. **

T. reesei     KELETLLINVQKTNLILVEELNRFRRSSGVVTRSSSPLDSLQDSITLSQQ 200
A. nidulans   IDMEQQN---QFLLQRLAQMEAENNRLSQQVAQLSAEVRGSRHSTPTSSS 166
Yeast         SLLENLLNSVNLEK--LADHE     *  *  *.   *.  .   *  *
               .*            .  *.

T. reesei     LFGSRDGQTMSNPEQSLMDQIMRSAANPTVNPASLSPSLPPISDKEFQTK 250
A. nidulans   PASVSPTLTPTLFKQEGDEVPLDRIPFPTPSVTDYSPTLKPSSLAE---- 212
                 *    *     .  **        .  **. **.* * *

T. reesei     EEDEEQADEDEEMEQTWHETKEAAAAKEKNSKQSRVSTDSTQRPAVSIGG 300
A. nidulans   -----------------------------------SPDLTQHPAVSVGG 226
                                                 * * ** ****.**

T. reesei     DAAVPVFSDDAGANCLGLDPVHQDDGPFSIGHSFGLSAALDADRYLLESQ 350
A. nidulans   LEGDESALTL---FDLGASIKHEPTHDLTAPLSDDDFRRLFNGDSSLESD 273
                            **  *     *    *      *       ***

T. reesei     LLASPNASTVDDDYLAGDSAACFTNPLPSDYDFDINDFLTDDANHAAYDI 400
A. nidulans   SSLLEDGFAFDV----LDSGDLSAFPFDSMVDFDTEPVTLEDLEQTNGLS 319
                 .  *        **    . *  * *  ***    .*    .

T. reesei     VAASNYAAADRELDLEIHDPENQIPSRHSIQQPQSGASSHGCDDGGIAVGV 451
A. nidulans   DSASCKAASL-------------------QPSHGASTSRCDGQGIAAGSA 350
              .**  **  .                   ** ***. ** ** *** *
```

FIG. 10

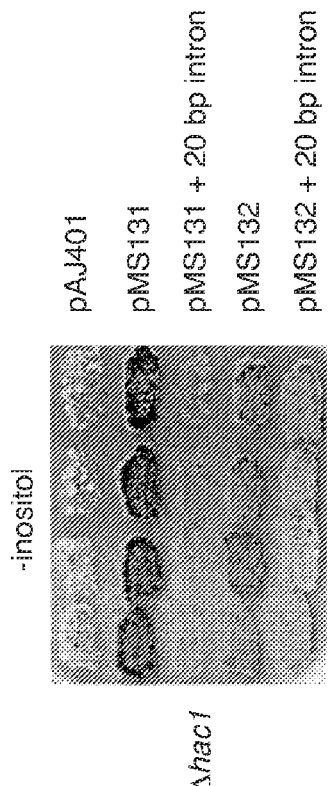
FIG. 15A
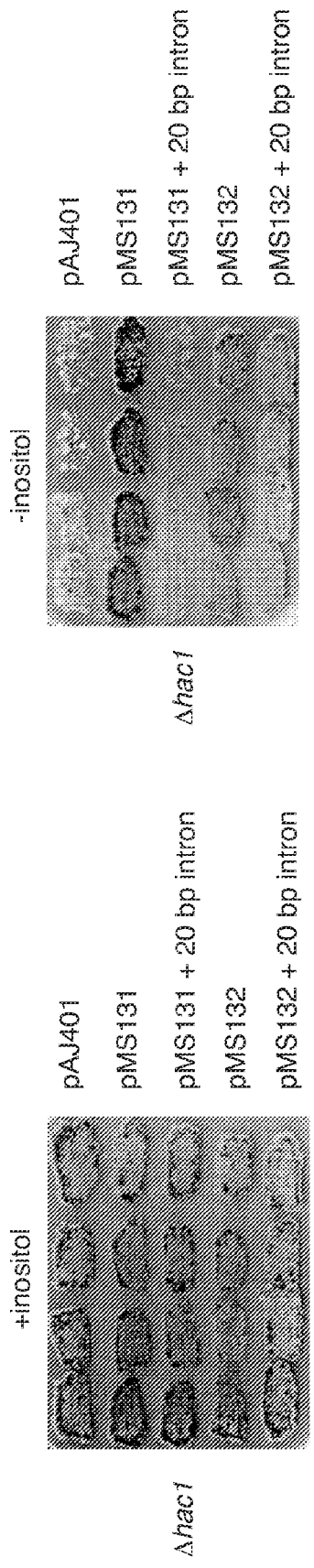
FIG. 15B
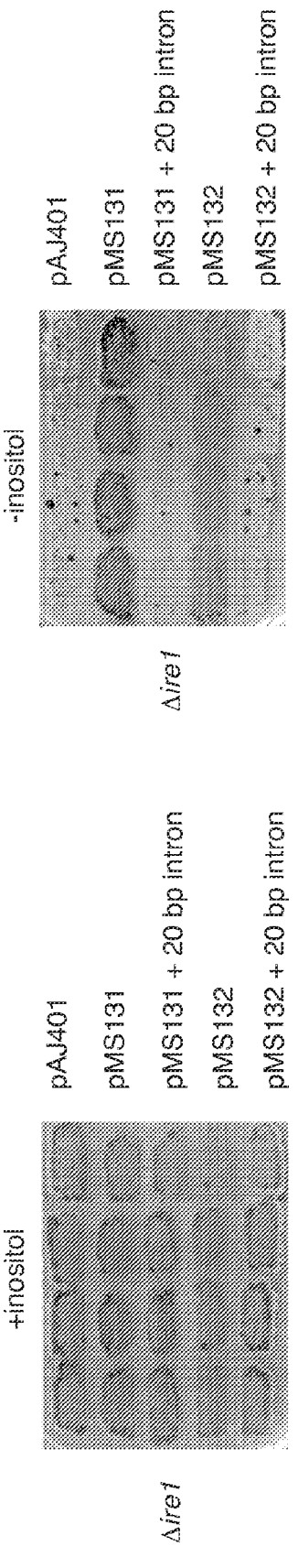
FIG. 15C
FIG. 15D

```
  1 TTTGAACAGCAGATCGTTACTGCCTACCCAGACGTTACAGTCCACGAGCTCACGGAGGAC
    F  E  Q  Q  I  V  T  A  Y  P  D  V  T  V  H  E  L  T  E  D
 61 GATGAATTCTTAGTAATCGCTTGCGATGgtgggtttcccctcaactttgccgctctgttc
    D  E  F  L  V  I  A  C  D  G
121 cacaatctgatatactacagGAATCTGGGATTGCCAGTCTTCCCAAGCCGTGGTCGAATT
                        I  W  D  C  Q  S  S  Q  A  V  V  E  F
181 CGTTCGCCGCGGTATCGCGGCCAAGCAGGATCTCTATCGGATTTGTGAAAACATGATGGA
    V  R  R  G  I  A  A  K  Q  D  L  Y  R  I  C  E  N  M  M  D
241 CAACTGTCTCGCTTCCAACAGTGAGACTGGTGGAGTTGGCTGTGACAACATGACAATGGT
    N  C  L  A  S  N  S  E  T  G  G  V  G  C  D  N  M  T  M  V
301 CATTATAGGTCTCCTCAATGGAAAAACTAAGGAAGAGTGGTACAACCAGATCGCGGAGCG
    I  I  G  L  L  N  G  K  T  K  E  E  W  Y  N  Q  I  A  E  R
361 GGTTGCTAACGGCGACGGCCCTTGTGCTCCGCCCGAATACGGCAAGTCTCTCGAGGAACC
    V  A  N  G  D  G  P  C  A  P  P  E  Y  G  K  S  L  E  E  P
421 CACGGCCTCCAATCCCTACTGACTGAACCGTGGGGGTTGCAGCTGAATTCCGAGGACCTG
    T  A  S  N  P  Y  *
481 GAATCCATAACCATTTTGAAGAGAACCCGGACGAGTACGAGATCGACCACGATCGCTCCC
541 GCCCATTCAACGTGCGTTCTGGTAGAATAATTCTTTTGGGAGATGGCAGCACGTTAATTC
601 CAGGAAAACAGAATGACGAGGAACTCTTTGACCAAACCGGGGAGGAGAATCACCCAGACC
661 AAGTGCAACGCCAGAATACCGACACAGAAAGAAATGACCGTGAAGGGACGCCTGGGCCTC
721 AATCCGCGGCTCCCCAGACGAACACGTCCGCTTCGGATGGCTCAGAGCCTTCTAACACAC
781 CGCAGAAACCCGCCTCTTCGTAGCTTCGTCATGAGATTTACGCCTGATTCCCTTCATTTT
841 GGTTCCTGAAACGACTCGTGATTTCACGATCCACACCCGCCGCCCATCTCCACGCCCGG
901 TGCCGAAGCCTCACAATTCTGCCCCATACGGTCGCTCATTGATTTTCTGTTTCTCACGA
961 TTTGAAGGCGCATTGGTGCTTGTGACCGCGAAGATGCGAAAGAGACGGACCATATCATCC
1021 CCTTCTATCTCTTGTTTTAATCCCATCTTCTTACTTTTTACGAGCTCATCCAGATCAAAT
1081 CACCTTCGTGTTACTCCAGGATGGATATCTTTGAGAATTCGCCGAATGGGTGGAGGCATC
1141 TTCTTTCCCTGTCATCTTTCTTCTCTATGTTTGCACATGCCGCAAGCGGCAGGCCTCACG
1201 AGAGTACGTTTGTTTCATGTCTCGACATAAGATACCGCAACAACCACTATTGACGAACTT
1261 TATAA
```

*FIG. 24*

```
   1                        GACGAGCCTCGATCCGCCTCGACGCCGCTGGTTTCCCCCTTCTTTCTCCCCCCT
  61        TCAGCCACGTCCTCGTGTCCTATAACCTTTCGCAGCCTACGGTCCCGCCTCCAGAGGTCT
 121        CGCGTCCCTGAGTACCAAACGATAGAAACAAGACTGCTATCTTTGTCGTGCTGCCTCCTC
 181        CCCTCCTCGACGCTTTTCCTCCCCCTCGATCGCTTTCCCGGCCCTCGTGAGACGTCGCAG
 241        CCATGGGCCAAACCCTCTCGGAGCCCGTTGTCGAAAAGACTTCCGAAAAGGGCGAGGATG
                M  G  Q  T  L  S  E  P  V  V  E  K  T  S  E  K  G  E  D
 301        ACAGACTCATCTACGGCGTGTCCGCCATGCAGGGCTGGCGCATCAGCATGGAGGACGCTC
             D  R  L  I  Y  G  V  S  A  M  Q  G  W  R  I  S  M  E  D  A
 361        ACACGGCTGAGCTGAATCTCCCCCCACCTGACAACGACACCAAGACGCACCCCGACAGGC
             H  T  A  E  L  N  L  P  P  P  D  N  D  T  K  T  H  P  D  R
 421        TGTCCTTTTTCGGAGTCTTCGACGGACACGGAGGAGACAAAGTAGCGTTATTCGCAGGCG
             L  S  F  F  G  V  F  D  G  H  G  G  D  K  V  A  L  F  A  G
 481        AGAACATTCACAACATTGTTTTCAAGCAGGAGAGCTTCAAATCCGGTGATTACGCTCAGG
             E  N  I  H  N  I  V  F  K  Q  E  S  F  K  S  G  D  Y  A  Q
 541        GTCTCAAGGACGGCTTTCTCGCTACGGATCGGGCTATTCTCAACGACCCCAAATACGAAG
             G  L  K  D  G  F  L  A  T  D  R  A  I  L  N  D  P  K  Y  E
 601        AGGAAGTCTCTGGCTGCACTGCCTGCGTCACCCTGATTGCCGGAAACAAACTATATGTCG
             E  E  V  S  G  C  T  A  C  V  T  L  I  A  G  N  K  L  Y  V
 661        CCAACGCCGGTGATTCTCGAAGCGTGCTGGGCATCAAGGGACGGGCCAAACCCCTATCCA
             A  N  A  G  D  S  R  S  V  L  G  I  K  G  R  A  K  P  L  S
 721        ACGACCACAAGCCTCAGCTTGAAACGGAGAAGAACCGAATCACAGCCGCTGGCGGTTTCG
             N  D  H  K  P  Q  L  E  T  E  K  N  R  I  T  A  A  G  G  F
 781        TCGACTTTGGCCGAGTCAACGGCAATCTGGCTCTGTCGCGTGCCATTGGCGACTTTGAAT
             V  D  F  G  R  V  N  G  N  L  A  L  S  R  A  I  G  D  F  E
 841        TCAAGAAGAGCGCCGAGCTGTCCCCCGAAAACCAGATCGTTACCGCCTTTCCCGATGTCG
             F  K  K  S  A  E  L  S  P  E  N  Q  I  V  T  A  F  P  D  V
 901        AGGTGCACGAGCTTACAGAGGAGGACGAGTTCCTGGTGATTGCCTGTGACGGTATCTGGG
             E  V  H  E  L  T  E  E  D  E  F  L  V  I  A  C  D  G  I  W
 961        ATTGCCAATCTTCCCAGGCTGTTGTTGAGTTTGTGCGACGAGGCATCGCCGCCAAGCAGG
             D  C  Q  S  S  Q  A  V  V  E  F  V  R  R  G  I  A  A  K  Q
1021        ACCTTGACAAGATCTGCGAGAACATGATGGACAACTGCCTTGCGTCCAACTCAGAAACGG
             D  L  D  K  I  C  E  N  M  M  D  N  C  L  A  S  N  S  E  T
1081        GTGGCGTCGGCTGCGACAACATGACCATGGTCATCATCGGCTTCCTGCACGGCAAGACCA
             G  G  V  G  C  D  N  M  T  M  V  I  I  G  F  L  H  G  K  T
1141        AGGAGGAGTGGTATGACGAAATTGCCAAGAGAGTGGCCAACGGAGACGGCCCCTGTGCCC
             K  E  E  W  Y  D  E  I  A  K  R  V  A  N  G  D  G  P  C  A
1201        CCCCGGAATATGCCGAGTTCCGCGGTCCCGGCGTTCACCACAACTACGAAGACAGCGACA
             P  P  E  Y  A  E  F  R  G  P  G  V  H  H  N  Y  E  D  S  D
1261        GCGGCTACGACGTCGACGCCGACAGCGGCGGCAAGTTTAGCCTTGCCGGATCCCGGGGTC
             S  G  Y  D  V  D  A  D  S  G  G  K  F  S  L  A  G  S  R  G
1321        GCATCATCTTCCTGGGCGACGGCACCGAAGTCCTGACGGGCTCCGACGACACGGAGATGT
             R  I  I  F  L  G  D  G  T  E  V  L  T  G  S  D  D  T  E  M
1381        TTGACAATGCTGACGAGGACAAGGACCTTGCGAGCCAGGTGCCCAAGAGCTCCGGCAAGA
             F  D  N  A  D  E  D  K  D  L  A  S  Q  V  P  K  S  S  G  K
1441        CCGATGCAAAGGAGGAGACAGAGGCCAAGCCGGCACCAGAGGCGGAGTCGTCCAAACCCG
             T  D  A  K  E  E  T  E  A  K  P  A  P  E  A  E  S  S  K  P
1501        CGGATGGGTCGGAGAAGAAGCAAGACGAAAAGACACCCGAGGAGAGTAAGAAGGATTAGG
             A  D  G  S  E  K  K  Q  D  E  K  T  P  E  E  S  K  K  D  *
1561        TGGTCCTCTTGAATTCTTTGGGCTCGTCTCCTTGAAGCCCCCGCTGGTGTTGTTGATGG
1621        CGTGTGTTTGTGTGTACGTGTGGCATAATTCTTTTTTCTTCCCATCACCGCTACTCAAAA
1681        AACCCCAGGCGTGAGGGCATTTTTAAATCGCATAGGGAGTGGGGGAGAGACGGGAGAGGC
1741        TCTGGAACGAAACATTCTGGGAGACAAGGCAGAGAGCGTAGGGGCGGTTTAGACATTGAG
1801        TGTTGCTCGTTAAAAAAAAAAAAAAAAAAAA
```

*FIG. 25*

```
CGGAGGCAAGAGTCATAGACGCGGGAAGAAGAAAATTGAGAGTGAGAAAGAGGAATCTGA   60
  G  G  K  S  H  R  R  G  K  K  K  I  E  S  E  K  E  E  S  D
TCACGCCCTGGCACCTTGCAACCCCCGGCTGGGCCCGATGCCGGGTTAGCTCTCACCCG   120
 H  A  P  G  T  L  Q  P  P  A  G  P  D  A  G  L  A  L  T  R
CACTGCATCTAATGAGGTGTTTGAAGCGGACGGTGTCATCCAGATTGGCCGTTTGAAGGT   180
  T  A  S  N  E  V  F  E  A  D  G  V  I  Q  I  G  R  L  K  V
CTTTACGGCTGACGTTCTGGGTCATGGAAGCCACGGGACAGTTGTTTACCGCGGGTCGTT   240
  F  T  A  D  V  L  G  H  G  S  H  G  T  V  V  Y  R  G  S  F
TGACGGCCGAGACGTCGCGGTCAAACGTATGCTGGTGGAGTTCTATGATATTGCATCGCA   300
  D  G  R  D  V  A  V  K  R  M  L  V  E  F  Y  D  I  A  S  H
CGAAGTGGGATTGTTGCAGGAAAGCGATGATCATAACAACGTTATCCGATGTTATTGCCG   360
  E  V  G  L  L  Q  E  S  D  D  H  N  N  V  I  R  C  Y  C  R
TGAGCAAGCCAAGGGTTTCTTCTACATCGCCCTTGAACTGTGTCCGGCTTCTTTGCAGGA   420
  E  Q  A  K  G  F  F  Y  I  A  L  E  L  C  P  A  S  L  Q  D
TGTGGTAGAACGACCAGACGCGTTCCCGCAGCTAGTCAATGGTGGCTTGGATATGCCGGA   480
  V  V  E  R  P  D  A  F  P  Q  L  V  N  G  L  D  M  P  D
CGTCTTGCGTCAAATTGTCGCCGGTGTCCGGTACCTACACTCTCTCAAAATCGTACACCG   540
  V  L  R  Q  I  V  A  G  V  R  Y  L  H  S  L  K  I  V  H  R
TGACTTGAAGCCTCAAAATATCCTGGTCGCCGCTCCTCGAGGCCGTATCGGTTCTCGGGC   600
  D  L  K  P  Q  N  I  L  V  A  A  P  R  G  R  I  G  S  R  A
CATCCGGCTTCTGATTTCGGACTTTGGCTTGTGCAAGAAACTTGAGGATAACCAGAGTTC   660
  I  R  L  L  I  S  D  F  G  L  C  K  K  L  E  D  N  Q  S  S
ATTCAGGGCAACCACGGCCCATGCTGCTGGTACTCCGGGTGGAGGGCTCCCGAACTGCTT   720
  F  R  A  T  T  A  H  A  A  G  T  P  G  G  G  L  P  N  C  L
GTGGATGACGACAAGAGCCGGTAATCAGGGTTCAGAGTCTCAAAATACGGAGTCATCTGA   780
  W  M  T  T  R  A  G  N  Q  G  S  E  S  Q  N  T  E  S  S  E
GCCGGCGGTCGTCGATCCCCAGACGAATCGACGAGCCACCCGAGCCATTGATATCTTCTC   840
  P  A  V  V  D  P  Q  T  N  R  R  A  T  R  A  I  D  I  F  S
CCTGGGATGTGTCTTCTACTACGTCCTAACTCGAGGATGTCATCCTTTTGACAAGAATGG   900
  L  G  C  V  F  Y  Y  V  L  T  R  G  C  H  P  F  D  K  N  G
CAAGTTCATGCGCGAAGCAAATATCGTCAAGGGGAATTTCAATCTCGATGAGTTACAGCG   960
  K  F  M  R  E  A  N  I  V  K  G  N  F  N  L  D  E  L  Q  R
TCTAGGAGAGTATGCGTTTGAAGCAGACGATCTTATCCGATCAATGTTGGCACTTGATCC  1020
  L  G  E  Y  A  F  E  A  D  D  L  I  R  S  M  L  A  L  D  P
ACGTCAACGgtatgtcccaacaacatcttcctttgccttgtggcgtagcgtactaatctc  1080
  R  Q  R
cacagCCCCGACGCAAGCGCTGTGTTAACCCATCCTTTCTTCTGGAATCCGTCCGACCGC  1140
         P  D  A  S  A  V  L  T  H  P  F  F  W  N  P  S  D  R
CTTAGCTTCCTCTGTGACGTTTCGGACCACTTCGAGTTCGAACCGAGAGATCCTCCATCT  1200
  L  S  F  L  C  D  V  S  D  H  F  E  F  E  P  R  D  P  P  S
GACGCTCTTCTGTGTCTAGAGTCTGTAGCCTCTGATGTCATTGGCCCTGAAATGAATCCT  1260
  D  A  L  L  C  L  E  S  V  A  S  D  V  I  G  P  E  M  N  P
CAAACTCCTGCCAAAGACTTCAAAGACAGTCTCGGAAGCAGCGAAAATACACCGGCTCC  1320
  Q  T  P  A  K  G  L  Q  R  Q  S  R  K  Q  R  K  Y  T  G  S
AAAAATGCTGGACTTGATGCGAGCCCTGCGGAACAAGCGCAACCACTACAATGATATGCCG  1380
  K  M  L  D  L  M  R  A  L  R  N  K  R  N  H  Y  N  D  M  P
GAGCATTTGAAAGCTCATATTGGTGGGCTGCCGGAGGGTTACTTGAATTTCTGGACCGTG  1440
  E  H  L  K  A  H  I  G  G  L  P  E  G  Y  L  N  F  W  T  V
CGTTTCCCGAGTTTGCTGATGAGTTGTCATTGGGTGATTGTTGAACTGGGATTGACGAAG  1500
  R  F  P  S  L  L  M  S  C  H  W  V  I  V  E  L  G  L  T  K
ACGGATCGGTTCCAAGAGATATTTTACGCCATTGGAGTAGGTTGTTGCGTACTGGTTCAG  1560
  T  D  R  F  Q  E  I  F  Y  A  I  G  V  G  C  C  V  L  V  Q
AAATATATTG
  K  Y  I
```

FIG. 26

```
   1  GCACGAGCAAGATACGGCCTCTCGCACCAAGGAGACACGCATATTCGTGGTACCATCGGC
  61  TGAGGGTGAAGGGGGGTTCAACACAGCACAACTCAGCGACCACTGGACTGGTGGAGCCGA
 121  AGCCCACGATCGAATCCACAGCCTGCACCACTTTCTCCTCGTCATATTCGCGGGGACTCA
 181  CAAGCGGTTTCCGTTGCCTTCGAATTCGACAGAGCTGCGACTGCGAGTCATTTCAGCGAC
 241  TCTAAACCTACTCCTTTGGCTGCTGCGCGGGACTGGTTCTGCCCAGCCTCTCCTACTCGA
 301  CCAACCGACGTCCTCTTTCTGCTTCCTCATCCCTTTCTCCTTTGACGTCCGAGCGTCAGA
 361  GCGAATTTTTCCTTGCTTCTTCGTTTGGGCCGGGAATGGCTTCTCTGGCATCGCAACAGC
 421  CTCTACCTCTCCGTTGGTAGAGCCATAGCCTGCAGCTCCCCATGTGATCCGCTCTCCGTC
 481  TCTCCGGCACCCCGACTTTCGTCTCGATCATGATGCGGCGACCCCCGAGCCAAGGACGAT
                                                                  M
 541  GGTCCGCGTCGCATCAGAAGCTCTCCTGGCTTTTGCCTTTATTCTCATACCATGGCTCCA
       V  R  V  A  S  E  A  L  L  A  F  A  F  I  L  I  P  W  L  Q
 601  ACTTGCCGATGCTCAGCAGCAGCCTCAGCAGCCCAGATTCGAATTCACTCACAAAGAGG
       L  A  D  A  Q  Q  Q  P  Q  Q  P  Q  I  R  I  H  S  Q  R  G
 661  CGACGCGCCCCTTGACAAAGTCGCCGACGATGCAACACCCGTTGGTACGCAACACATGC
       D  A  P  L  D  K  V  A  D  D  A  N  T  R  W  Y  A  T  H  A
 721  TGCACCAGACGTGCACCCCGAAGCGAAGTTCGACACCGTCAACAGGAAGCAAAAGCAGCA
       A  P  D  V  H  P  E  A  K  F  D  T  V  N  R  K  Q  K  Q  Q
 781  GTCGACCGCTTCGCCCCAGCAACACCAGAAATATCGACGAGCCCCCTATGACTACGCCAG
       S  T  A  S  P  Q  Q  H  Q  K  Y  R  R  A  P  Y  D  Y  A  S
 841  CAAGGACAAGGCCCAGAACCGATATGCGCAGCACCCTATCCGCGAATCCGAGAAACCAAA
       K  D  K  A  Q  N  R  Y  A  Q  H  P  I  R  E  S  E  K  P  N
 901  CTACGTAAAAGTCCCCAACGATGCGAGCGCCCTCGCAACTTTAGCTCCGGCTCAGCCCGT
       Y  V  K  V  P  N  D  A  S  A  L  A  T  L  A  P  A  Q  P  V
 961  CCGAGCACCACACACCTCACGACATCACTGGCCCAGCAGCAGCGCCGCTTCTGGGCTGGC
       R  A  P  H  T  S  R  H  H  W  P  S  S  A  A  S  G  L  A
1021  CTCGCCGCACAATGCGCGGAGTCTGGAGGACTGGGAAGTTGAAGACTTTGTTCTTCTGGC
       S  P  H  N  A  R  S  L  E  D  W  E  V  E  D  F  V  L  L  A
1081  GACCGTCGATGGAGACCTCTATGCCAGCGACCGAAAGACCGGTCGGCACCTCTGGCACCT
       T  V  D  G  D  L  Y  A  S  D  R  K  T  G  R  H  L  W  H  L
1141  CGAGGTCGACCAGCCAGTGGTTGAAACCAAACACTACCGAACAAACAACTCCGTCCTCGA
       E  V  D  Q  P  V  V  E  T  K  H  Y  R  T  N  N  S  V  L  D
1201  CGACGACTATCGCCCCGTCGACCACTACATCTGGGCCGTCGAGCCGAGCCGCGATGGAGG
       D  D  Y  R  P  V  D  H  Y  I  W  A  V  E  P  S  R  D  G  G
1261  GCTCTATGTATGGATCCCCGACTCCGGAGCGGGCCTCGTCAGGACCGGCTTCACCATGAA
       L  Y  V  W  I  P  D  S  G  A  G  L  V  R  T  G  F  T  M  K
1321  GCACCTCGTTGAAGAACTTGCTCCATACGCCGGCGACGAGCCCCCCGTTGTCTATACCGG
       H  L  V  E  E  L  A  P  Y  A  G  D  E  P  P  V  V  Y  T  G
1381  AGACAAGAAGACGACCATGGTCACCCTGGACGCCGCTACCGGGCGCGTTCTCAAATGGTT
       D  K  K  T  T  M  V  T  L  D  A  A  T  G  R  V  L  K  W  F
1441  TGGCTCTAGCGGCTCCCAAGTCAACGAAGCCGAGAGCTGCCTTCGGCCCAATGCCTTTGA
       G  S  S  G  S  Q  V  N  E  A  E  S  C  L  R  P  N  A  F  D
1501  CGACAGGGATACCACAGAGTGCAGCTCCATGGGCACAATCACGCTGGGAAGGACCGAGTA
       D  R  D  T  T  E  C  S  S  M  G  T  I  T  L  G  R  T  E  Y
```

*FIG. 27A*

```
1561 CACGGTGGGCATCCAGAGGCGAGACGGTCGCCCTATCGCAACCTTGAAGTACGCAGAATG
      T  V  G  I  Q  R  R  D  G  R  P  I  A  T  L  K  Y  A  E  W
1621 GGGACCCAACACCTTTGACAGCGACCTCTACCAGCAATACCACGCCTCGTTGGACAACCA
      G  P  N  T  F  D  S  D  L  Y  Q  Q  Y  H  A  S  L  D  N  H
1681 TTACATCACCAGTCAGCACGACGGGAGAATTTACGCGTTTGACAAGTCACAGGCAGAAAA
      Y  I  T  S  Q  H  D  G  R  I  Y  A  F  D  K  S  Q  A  E  N
1741 CGACCTGCCCCTCTACACCCACAAGTTTTCGTCTCCCGTCGCCCGGGTCTTCGATGTCTG
      D  L  P  L  Y  T  H  K  F  S  S  P  V  A  R  V  F  D  V  C
1801 TCGACCGTGGGATGCGAATGCGGGAAGCAACCCGGAGCTGGTGGTTCTCCCCCAACCTCC
      R  P  W  D  A  N  A  G  S  N  P  E  L  V  V  L  P  Q  P  P
1861 AATTCCAGCGCTTGATGAGAGCACTGTCAAGATGCGAAGCAACAGCATCTTCCTCAACCA
      I  P  A  L  D  E  S  T  V  K  M  R  S  N  S  I  F  L  N  Q
1921 GACTGAAAGCGGCGACTGGTATGCGCTCTCCGGCCGTGCGTATCCGCTTATACTCGATGC
      T  E  S  G  D  W  Y  A  L  S  G  R  A  Y  P  L  I  L  D  A
1981 CCCCGTGGCCCAGATCTCGCGGGACGACTTGTGGGATATGGCCCATGCCTTTGATTCCAT
      P  V  A  Q  I  S  R  D  D  L  W  D  M  A  H  A  F  D  S  I
2041 TAACCCAAATAAGCTGTCCAAGGCCCTGGTGGGAACCCACTTTCTGAATCCCGTCAAGAG
      N  P  N  K  L  S  K  A  L  V  G  T  H  F  L  N  P  V  K  S
2101 CACCGGTTACCATCAGCCGCCGACGCTCCCTGCCGGCGCCCTCGACGAGTATTACGAGGA
      T  G  Y  H  Q  P  P  T  L  P  A  G  A  L  D  E  Y  Y  E  D
2161 CTTGGAGAACGCCTCAAACAATGCTCACGCCGTGACAAACACTGTTCCGGAGGAGCCCAC
      L  E  N  A  S  N  N  A  H  A  V  T  N  T  V  P  E  E  P  T
2221 CATCATCACCAAAGTCAAGGCTCTTCCGCAGAGTGCTGCGAACAGCGTCATTGACTTTGT
      I  I  T  K  V  K  A  L  P  Q  S  A  A  N  S  V  I  D  F  V
2281 CAGCAACCCCATTCTCATCATTTTCTTGATAGGCTCCTTGATCTACAACGAAAAGAAGCT
      S  N  P  I  L  I  I  F  L  I  G  S  L  I  Y  N  E  K  K  L
2341 GCGACGGTCGTATCATCGGTTCCGGACTCATGGCACAATCAAGGACGTCTATCCCTTCTT
      R  R  S  Y  H  R  F  R  T  H  G  T  I  K  D  V  Y  P  F  F
2401 CGTTATCGAATCTGAGGCCGGAGATGAATCAGGTGATGACAAGGACGGTGTGTTCCCATC
      V  I  E  S  E  A  G  D  E  S  G  D  D  K  D  G  V  F  P  S
2461 TTCGCCGTCTCCGCGCAGTCAACCCCAGGACCAAAATGCGGAAGACCACCTGTCCAGACA
      S  P  S  P  R  S  Q  P  Q  D  Q  N  A  E  D  H  L  S  R  H
2521 CAAGGTGGAGAGGAATGCCGGCGACCAGGACAAGGTCAAGGACAACAGGAGCCTGCATGA
      K  V  E  R  N  A  G  D  Q  D  K  V  K  D  N  R  S  L  H  D
```

FIG. 27B

```
2581 CGTTTCTGACACCTTGGAACCGAGCAACAAGACTGTTGAGAAAACGGCCGATGTGGTCAA
       V  S  D  T  L  E  P  S  N  K  T  V  E  K  T  A  D  V  V  K
2641 GCAAGTGGATGTAGCTGGCCCTGACGCACCCTCGACGGACTCCAATGGTGCTGCACCGGA
       Q  V  D  V  A  G  P  D  A  P  S  T  D  S  N  G  A  A  P  E
2701 GAAGAAGAAGAAGGCTCACCGAGGCCGTCGTGGCGGTGTCAAGCACAGAAAGGGTCGGCC
       K  K  K  K  A  H  R  G  R  R  G  G  V  K  H  R  K  G  R  P
2761 CACCGACGGCTCGCAGTCTCATGAAAACGACCCAGCTCTCACTACAGTGGACGAGGCTGT
       T  D  G  S  Q  S  H  E  N  D  P  A  L  T  T  V  D  E  A  V
2821 AAGCAATGCGAAGAAGCTGGGTGACCGGCCAAGCCTGGAACCCGACGTCATGACCATCTA
       S  N  A  K  K  L  G  D  R  P  S  L  E  P  D  V  M  T  I  Y
2881 CAACGACATGCAAGCCGTCACGGGCTCTGTTATCAGCATGGGAAACATCGAGGTCGATAC
       N  D  M  Q  A  V  T  G  S  V  I  S  M  G  N  I  E  V  D  T
2941 GGATGTCGAGCTTGGCATGGGCAGCAACGGTACTGTCGTATTTGCTGGCCGATTCGATGG
       D  V  E  L  G  M  G  S  N  G  T  V  V  F  A  G  R  F  D  G
3001 CAGGGACGTCGCCGTCAAGAGAATGACGATTCAGTTCTACGACATTGCCACGCGAGAAAC
       R  D  V  A  V  K  R  M  T  I  Q  F  Y  D  I  A  T  R  E  T
3061 TAAGTTGCTGCGCGAGAGTGACGACCACCCCAATgtaaatcagccctcatcgtttcaccc
       K  L  L  R  E  S  D  D  H  P  N
3121 attttcccttcgctaacgtaaccactgtctgcacGTCATTCGGTATTACTCACAAGTGCA
                                           V  I  R  Y  Y  S  Q  V  Q
3181 GCGAGGCGACTTCCTGTATATTGCCTTGGAACGCTGCGCTGCTTCATTGGCAGATGTCAT
       R  G  D  F  L  Y  I  A  L  E  R  C  A  A  S  L  A  D  V  I
3241 TGAAAAGCCGTATGCCTTTGGTGAATTGGCCAAGGCTGGACAAAAGGACCTACCGGGCGT
       E  K  P  Y  A  F  G  E  L  A  K  A  G  Q  K  D  L  P  G  V
3301 CTTGTACCAAATCACCAACGGCATCAGCCACTTGCACTCTCTGCGGATTGTTCATCGAGA
       L  Y  Q  I  T  N  G  I  S  H  L  H  S  L  R  I  V  H  R  D
3361 CTTGAAGCCTCAAAACATCTTGGTCAACTTGGACAAGGACGGCAGACCAAGGCTCTTGGT
       L  K  P  Q  N  I  L  V  N  L  D  K  D  G  R  P  R  L  L  V
3421 GTCGGACTTTGGCCTGTGTAAGAAACTGGAGGATAGACAGTCTTCGTTCGGAGCAACGAC
       S  D  F  G  L  C  K  K  L  E  D  R  Q  S  S  F  G  A  T  T
3481 AGGCCGAGCCGCTGGAACGTCGGGATGGCGTGCCCCGAACTGCTTCTCGATGACGACGG
       G  R  A  A  G  T  S  G  W  R  A  P  E  L  L  L  D  D  D  G
3541 ACAGAATCCCGCAGCCATCGATAGCAGTACGCACAGCGGCTCTCACACCATCCTCGTGGG
       Q  N  P  A  A  I  D  S  S  T  H  S  G  S  H  T  I  L  V  G
3601 AGACCCCAACTCGCTTTCCAATGGAGGGCGAGCCACGAGGGCCATTGACATCTTCTCCCT
       D  P  N  S  L  S  N  G  G  R  A  T  R  A  I  D  I  F  S  L
3661 TGGCCTTGTCTTCTTCTACGTGCTCACCAATGGATCCCACCCGTTTGACTGTGGCGACAG
       G  L  V  F  F  Y  V  L  T  N  G  S  H  P  F  D  C  G  D  R
3721 ATATATGCGGGAGGTGAACATTCGAAAGGGCAACTACAATCTCGATCCATTGGACGCTCT
       Y  M  R  E  V  N  I  R  K  G  N  Y  N  L  D  P  L  D  A  L
3781 GGGCGACTTTGCCTACGAAGCCAAGGATCTGATTGCGTCCATGCTCCAGGCCTCTCCCAA
       G  D  F  A  Y  E  A  K  D  L  I  A  S  M  L  Q  A  S  P  K
3841 GGCACGACCCCGACTCGCGAGAGGTCATGGCCCACCCTTTCTTCTGGTCTCCGAAGAAGCG
       A  R  P  D  S  R  E  V  M  A  H  P  F  F  W  S  P  K  K  R
3901 TCTGGCCTTTTTGTGCGACGTGTCGGATTCTCTGGAGAAGGAGGTGCGAGATCCTCCGTC
       L  A  F  L  C  D  V  S  D  S  L  E  K  E  V  R  D  P  P  S
3961 GCCTGCCTTGGTCGAGCTGGAGCGACATGCGCCGGAGGTCATTAAGGGAGACTTCTTGAA
       P  A  L  V  E  L  E  R  H  A  P  E  V  I  K  G  D  F  L  K
4021 GGTGCTCACGCGCGACTTTGTCGAGTCGCTGGGCAAGCAGCGCAAGTACACCGGGAACAA
       V  L  T  R  D  F  V  E  S  L  G  K  Q  R  K  Y  T  G  N  K
4081 GCTGCTCGACCTGTTGCGCGCTCTTCGCAACAAGCGGAATCACTACGAAGACATGTCGGA
       L  L  D  L  L  R  A  L  R  N  K  R  N  H  Y  E  D  M  S  D
4141 CTCGCTGAAGCGCAGCGTGGGATCACTCCTGATGGGTATCTTGCTTATTGGACGGTCAA
       S  L  K  R  S  V  G  S  L  P  D  G  Y  L  A  Y  W  T  V  K
4201 GTTCCCGATGCTGTTGCTGACGTGCTGGAACGTGGTGTATAATCTCGAGTGGGAGAAGAC
       F  P  M  L  L  L  T  C  W  N  V  V  Y  N  L  E  W  E  K  T
4261 GGATCGGTTCAGGGAGTACTATGAGCCTGCCGGATTGTAGAAGAAGAAAAGGAAGAGAA
       D  R  F  R  E  Y  Y  E  P  A  G  L  *
4321 AAGAAAGGCCTCTTGCTTGTTTGGTTGCTGTATATCTTTTTGCTCGAAGATGGAAACGGA
4381 AAATATTGGGGAAGTTGCATGGGAAGTGAACAAAAGAGGGGAAAAATGGTGAATGTGAAA
4441 GCAAAGTCGGTTAGCGGGTGGGCATGGTCGTCATCCATGTAATTGTTTCAGCTTCTGTTG
4501 CATCAAAAGCGTTGTGTTTTCGTTCTTT
```

*FIG. 27C*

```
  1  CTTTTTATTGTTCTATGGTTCTTAAGGACACCTGTCCTTCTTGGCCCTATCCTTCTTGTT
                    M  V  L  K  D  T  C  P  S  W  P  Y  P  S  C

61  GTCTGGTACACTTGACCCCAGGCACCACTTGGCCTGGCCCCCCAGCTTCCCCG
      C  L  V  H  L  T  P  G  T  T  W  P  G  L  A  P  P  A  S  P

121  TTATGACACGGTGGCCTGTGTTCCTGTGACAGGGCAAGCAGACGTCCTCCACAAGCTGT
      V  M  T  R  W  P  V  F  L
                                     M  E  E  A  F
181  GTCGACCTACATCACCGTCCTCCCTTGCAGTGCGGTTAAGATAAGGCTCATAGTAAATCG
241  ATTGATCCACACAATTAAAGATCAATCACCTGTCACGCTTGAAATGATGGAAGAAGCATTCT

301  CTCCAGTCGACTCCCCGCCTCCCCGACGCCTGAGTTGCCATTGTTGACAGTGTCCC
      S  P  V  D  S  L  A  G  S  P  T  P  E  L  P  L  L  T  V  S

361  CGGCGGGACACGTCGCTTGATGACTCGTCAGTACAGGCCAGGGGAGACCAAGGCCGAAGAGA
      P  A  D  T  S  L  D  D  S  S  V  Q  A  G  E  T  K  A  E  E

421  AGAAGCCTGTGAAGAAGAGAAAGAGTCATGGGCCAGGAATTGCCAGTCCCGAAGACTAACT
      K  K  P  V  K  K  R  K  S  W  G  Q  E  L  P  V  P  K  T  N

481  TGCCCCCAAGGAAACGGGCCAAGACTGAAGATGAGAAAGAGCAACGTCGTATCGAGGCCG
      L  P  P  R  K  R  A  K  T  E  D  E  K  E  Q  R  R  I  E  R
```

FIG. 28A

```
541  TTCTTCGCAATCGTGCGGCAGCACAAACATCACGCGAGCGCAAGAGGCTCGAAATGGAGA
     V   L   R   N   R   A   A   A   Q   T   S   R   E   R   K   R   L   E   M   E

601  AGTTGGAAAATGAGAAGATTCAGATGGAACAGCAAAACCAGTTCCTTCTGCAACGACTAT
     K   L   E   N   E   K   I   Q   M   E   Q   Q   N   Q   F   L   L   Q   R   L

661  CCCAGATGGAAGCTGAGAACAATCGCTTAAACCAACAAGTCGCTCAACTATCTGCTGAGG
     S   Q   M   E   A   E   N   N   R   L   N   Q   Q   V   A   Q   L   S   A   E

721  TCCGGGGGCTCCCCGTGGCAACACTCCCCAAGCCCGGCTCCCCCGTCTCCAGCTTCTCCTACCC
     V   R   G   S   R   G   N   T   P   K   P   G   S   P   V   S   A   S   P   T

781  TAACTCCTACCCTATTTAAACAAGAACGCGACGAAATCCCTCTTGAACGGATTCCTTTCC
     L   T   P   T   L   F   K   Q   E   R   D   E   I   P   L   E   R   I   P   F

841  CCACACCCTCTATCACCGACTACTCCCCTACCCTTGAGGCCTTCCACTCTGGCTGAGTCCT
     P   T   P   S   I   T   D   Y   S   P   T   L   R   P   S   T   L   A   E   S

901  CCGACGTGACACAACATCCTGCAGcggtgttgtgcgacctgcagTGTCCGTCGCTGGACT
     S   D   V   T   Q   H   P   A                           V   S   V   A   G   L 961  CGAAGGAGAAGGAAGTGCCCTCTCTCTTTGACGTCGGCTCAAACCCTGAACCTCACGC
     E   G   E   G   S   A   L   S   L   F   D   V   G   S   N   P   E   P   H   A
```

*FIG. 28B*

```
1021  TGCCGATGATCTTGCAGCTCCCTCTTTCTGACGATGACTTCCACCGCCTATTCAACGTTGA
         A  D  D  L  A  A  P  L  S  D  D  D  F  H  R  L  F  N  V  D
1081  TTCACCCGTTGGGTCAGATTCTTCAGTCCTTGAAGACGGTTCGCCTTTGACGTTCTCGA
         S  P  V  G  S  D  S  S  V  L  E  D  G  F  A  F  D  V  L  D
1141  CGGAGGAGATCTATCAGCATTTCCATTTGATTTCTATGGTTGATTTCGACCCCGAATCTGT
         G  G  D  L  S  A  F  P  F  D  S  M  V  D  F  D  P  E  S  V
1201  TGGCTTCGAAGGCATCGAGCCGCCCCACGGTCTTCCGGATGAGACTTCTCGCCAGACTTC
         G  F  E  G  I  E  P  P  H  G  L  P  D  D  E  T  S  R  Q  T  S
1261  TAGCCGTGCAACCCAGCCTTGGCGCCGTCCACTTCGCCGATGCCAGGGCAGGGCATTGCAGC
         S  V  Q  P  S  L  G  A  S  T  S  R  C  D  G  Q  G  I  A  A
1321  TGGCTGTTAGCGAGCAGTTTCGCCAGGGAGATGCATCGGCTGTCGATGGTAACGGAGTCC
         G  C
1381  AATGGAGCTGGGAGTCTTTGTTGTTGACCTTGGCGTGACGATAGACCTACTCGAACAGCCGG
1441  GACGACGCAAACGAAATCTTGAGCGGTTTGAAATCAGCGAAAACTGACGGCGAAGTAATA
1501  TTGGCAAGTCTCAAAGGAGTACACGGAGTTCATGGAGTTCACGAAGCACCCAAGAGGCGT
1561  TGACGTCTCTCCTTATGGCAAGCATAGTTGAGGTTCCGGCTGTAAATTATCATAAATCC
1621  TTATAATTTTATTCTAGATTTCAATACAGCAGTTGTCTGCTCATC
```

*FIG. 28C*

INCREASED PRODUCTION OF SECRETED PROTEINS BY RECOMBINANT EUKARYOTIC CELLS

RELATED APPLICATIONS

This application is a Continuation-In-Part of U.S. application Ser. No. 09/534,692, filed Mar. 24, 2000, and is hereby incorporated by reference in its entirety.

FIELD OF THE INVENTION

This invention relates to cells which have been genetically manipulated to have an elevated unfolded protein response (UPR) resulting in an increased capacity to produce secreted proteins.

BACKGROUND OF THE INVENTION

The secretory pathway of eukaryotic organisms is of interest since cells can be engineered to secrete a particular protein of interest. The secretory pathway starts by translocation of the protein into the lumen of the endoplasmic reticulum (ER). In the ER the proteins fold into their final three-dimensional conformation and the core part of the N-glycans are attached to them. A quality control mechanism involving the proteins calnexin and calreticulin also resides in the ER, letting only completely folded proteins continue on the secretory pathway to the next compartment (Hammond and Helenius, 1995, Curr. Opinion Cell Biol. 7:523-529). Secretory proteins that do not fold properly are transported back to the cytoplasm by the translocation machinery and are degraded by the proteasome system (Wiertz et al., 1996, Nature 384:432-438).

The folding and glycosylation of the secretory proteins in the ER is assisted by numerous ER-resident proteins. The chaperones like Bip (GRP78), GRP94 or yeast Lhs1p help the secretory protein to fold by binding to exposed hydrophobic regions in the unfolded states and preventing unfavourable interactions (Blond-Elguindi et al., 1993, Cell 75:717-728). The chaperones are also important for the translocation of the proteins through the ER membrane. The foldase proteins like protein disulphide isomerase and its homologs and prolyl-peptidyl cis-trans isomerase assist in formation of disulphide bridges and formation of the right conformation of the peptide chain adjacent to proline residues, respectively. A machinery including many protein components also resides in the ER for the addition of the N-linked core glycans to the secretory protein and for the initial trimming steps of the glycans.

The levels of the chaperone and foldase proteins found in the ER are regulated at the transcriptional level. For each gene there is a basic level of transcription that can be increased in response to various stimuli. A large amount of secretory protein in the ER (secretory load) can induce the mammalian GRP78 gene, and this induction is mediated through the NF-κB transcription factor (Pahl and Baeuerle, 1995, EMBO J. 14:2580-2588). Furthermore, the ER chaperone and foldase genes are upregulated when the amount of unfolded protein increases in the ER. This induction has been named unfolded protein response (UPR) and it has been described in mammalian cells, yeast and filamentous fungi (McMillan et al., 1994, Curr. Opinion in Biotechnol. 5:540-545). The induction can be caused by treatment of cells with reducing agents like DTT, by inhibitors of core glycosylation like tunikamycin or by Ca-ionophores that deplete the ER calcium stores. The promoters of mammalian and yeast genes regulated by UPR have a conserved sequence region called UPR element, where the transcription factor responsible for the induction binds.

When the unfolded protein response pathway is active, a signal is tranduced from the ER lumen to the transcription machinery in the nucleus. A protein implicated in the UPR induction is the IRE1 protein of yeast (Cox et al., 1993, Cell 73:1197-1206, Mod et al., 1993, Cell 74:143-156). It is large protein having a transmembrane segment anchoring the protein to the ER membrane. A segment of the IRE1 protein has homology to protein kinases and the C-terminal tail has some homology to RNAses. It is believed that the IRE1 protein may be the first component of the UPR signal transduction pathway, sensing the ER lumen for the presence of unfolded proteins and transmitting the signal eventually to a transcription factor inducing the ER-protein genes. It has been reported that the IRE1 protein oligomerizes and gets phosphorylated when the UPR is activated (Shamu and Walter, 1996, EMBO J. 15:3028-3039). Over-expression of the IRE1 gene in yeast leads to constitutive induction of the UPR (Id.). Phosphorylation of the IRE1 protein occurs at specific serine or threonine residues in the protein.

Another protein reportedly implicated in the regulation of the UPR pathway is PTC2, a yeast protein phosphatase encoded by the PTC2 gene (Welihinda et al., 1998, Mol. Cell. Biol. 18, 1967-1977). The IRE1 protein is phosphorylated when the UPR pathway is turned on (Shamu and Walter, 1996, EMBO J. 15:3928-3039), and PTC2 dephosphorylates the IRE1 protein and regulates the UPR.

It has further been reported that the yeast transcription factor mediating the UPR induction of the chaperone and foldase genes is the HAC1 protein (Cox and Walter, 1996, Cell 87:391-404, Sidrauski et al., 1996, Cell 87:405-413). It belongs to the bZIP family of transcription factors, having a basic DNA-binding region and a leucine zipper dimerisation domain. The binding of the HAC1 protein to the UPR element of ER-protein gene promoters has been demonstrated (Mod et al., 1998, J. Biol. Chem. 273: 9912-9920). The action of the HAC1 protein is regulated by its amount in the cells; none of the protein can be found in uninduced cells and upon UPR induction it appears rapidly. The HAC1 protein amount is dependent of the splicing of the respective mRNA. In uninduced conditions the intron present in the HAC1 gene close to the translation termination codon is not spliced off, and this intron prevents the formation of HAC1 protein by preventing the translation of the mRNA (Chapman and Walter, 1997, Curr. Biol. 7, 850-859, Kawahara et al., 1997, Mol. Biol. Cell 8, 1845-1862). When UPR is induced, the intron is spliced and the mRNA is translated to form HAC1 protein that activates the promoters of its target genes. The HAC1 intron is spliced by an mechanism not currently described for any other system, involving the RNAse activity of the IRE1 protein and a tRNA ligase (Sidrauski and Walter, 1997, Cell 90, 1031-1039, Gonzales et al., 1999, EMBO J. 18, 3119-3132, Sidrauski et al., 1996, Cell 87, 405-413). The unfolded protein response can be induced constitutively in yeast by transformation with a UPR inducing version of the HAC1 gene. (Cox and Walter, supra.)

Thus, as indicated above, there are a number of reports regarding the secretory pathway. Additionally, there are reports on how to increase secretion so as to provide greater yields of heterologous proteins. Greater yields of protein are generally of interest to industry to provide more of a particular protein and to facilitate purification.

For example, in one report random mutagenesis of the host organism has been performed followed by screening for increased yield of a secreted protein. In another report, there has been fusion of a heterologous protein to an efficiently secreted endogenous protein in order to increase the yield of secretion of the heterologous protein. Both of these methods have been of limited success and other methods to improve protein secretion are desirable.

In other studies, there has reportedly been increased yields of secreted heterologous proteins in yeast by either overexpression or deletion of the yeast ER foldase or chaperone genes on an individual or pairwise basis. For example, overexpression of either the protein disulphide isomerase (PDI) or the KAR2 (homologous to the gene for the mammalian ER chaperone BiP) genes in yeast has been shown to increase the extracellular accumulation of certain secreted heterologous proteins (Robinson et al., 1996, Bio/Technology, 12:381-384; Harmsen, et al., 1996, Appl. Microbiol. Biotechnol., 46:365-370). In contrast, deletion of the CNE1 gene, encoding an ER chaperone homologous to mammalian calnexin, reportedly can lead to increased secretion of a heterologous protein (Parlati et al., 1995, *J. Biol. Chem.* 270:244-253, Harmsen, supra.). The effect of over-expression or deletion of individual or pairs of ER chaperones or foldases has also been reported on in filamentous fungi, however, increased secretion was not obtained. (Punt, et al., 1998, Appl. Microbiol. Biotech, 50:447-454; Wang, et al., 2000, Current Genetics, 37:57-64).

Therefore, it is desirable to provide new methods to increase production of secreted proteins in eukaryotic cells which are simple and consistent. It is also desirable to provide compositions such as novel genes to be used in methods for the increased production of secreted proteins. It is further desirable to provide eukaryotic cells according to the invention which are transformed with heterologous genes so as to have an increased capacity to produce secreted proteins.

SUMMARY OF THE INVENTION

Provided herein are methods for increasing the secretion of a heterologous protein in a cell comprising inducing an elevated unfolded protein response (UPR). The increase in protein secretion is compared to a level of protein secreted by the cell when the UPR is not elevated by the methods described herein. In one aspect, the method includes inducing the elevated UPR by increasing the presence of the HAC1 protein in the cell. In one aspect of the invention, the presence of the HAC1 protein can be increased by a number of methods. For example, the HAC1 gene can be overexpressed compared to its native state. Overexpression can be achieved by a variety of ways including the use of preferred vectors and promoters as further described herein. In one embodiment, the HAC1 protein is increased in a cell by transformation of said cell by a nucleic acid comprising a UPR inducing form of a HAC1 recombinant nucleic acid.

The HAC1 nucleic acid encoding a HAC1 protein can be from a variety of sources. It is understood that in one embodiment, HAC1 is used interchangeably with had, etc., and one embodiment is meant to encompass HAC1 homologs. Additionally, the skilled artisan can ascertain by the context whether the HAC1 is a nucleic acid, protein or either. In one embodiment, a HAC1 nucleic acid is isolated from yeast. In another embodiment, a HAC1 nucleic acid is isolated from filamentous fungi such as *Trichoderma* or *Aspergillus*.

In another aspect of the invention, the elevated UPR is induced by modulating the levels of IRE1 protein or PTC2 protein in said cell. Nucleic acids encoding IRE1 or PTC2 can be isolated from yeast or filamentous fungi such as *Trichoderma* or *Aspergillus*. In a preferred embodiment the nucleic acid encoding IRE1 or PTC2 is isolated from *T. reesei, A. nidulans* or *A. niger*.

The cell from which the protein is secreted can be any cell having an UPR. Cells having an UPR include all eukaryotes including but not limited to mammalian cells, insect cells, yeast and filamentous fungi.

Also provided herein is an isolated nucleic acid encoding a HAC1 protein, wherein said HAC1 has unfolded protein response inducing activity and has less than 50% similarity to yeast HAC1 protein. In another embodiment, an isolated nucleic acid encoding a HAC1 protein is provided, wherein said HAC1 protein has unfolded protein response inducing activity and wherein said HAC1 comprises a DNA binding region that has greater than 70% similarity to the DNA binding region of filamentous fungi HAC1. Embodiments of a DNA binding region are shown at amino acids 84-147 of the *T. reesei* protein shown in FIG. 10, at amino acids 53-116 of the *A. nidulans* protein shown in FIG. 10, and at amino acids 45-109 of the *A. niger* protein shown in FIG. 28. In one embodiment, the HAC1 protein encoded by the HAC1 nucleic acid provided herein has an amino acid sequence having greater than 70% similarity to the sequence of FIG. 7, FIG. 8 or FIG. 28. The proteins encoded by such nucleic acids are also provided herein.

In one embodiment, the nucleic acid provided herein encodes an amino acid sequence as set forth in FIG. 7, FIG. 8 or FIG. 28. In yet another embodiment, the nucleic acid provided herein has a nucleic acid sequence as set forth in FIG. 7, FIG. 8 or FIG. 28. The proteins encoded by such nucleic acids are also provided herein.

Further provided herein is an isolated nucleic acid encoding a PTC2 protein wherein said PTC2 protein modulates unfolded protein response and wherein said PTC2 protein has at least 70% similarity to the amino acid sequence of FIG. 24 or FIG. 25. In preferred embodiments the PTC2 protein has preferably at least 80%, more preferably at least 90% or more preferably at least 95% similarity to said amino acid sequences. In one aspect, the PTC2 protein has an amino acid sequence as set forth in FIG. 24 or FIG. 25. In another aspect, the PTC2 nucleic acid has a nucleic acid sequence as set forth in FIG. 24 or FIG. 25. The proteins encoded by such nucleic acids are also provided herein. It is understood that as used herein, PTC2 can be used interchangeably with ptc2 and ptcB, and that in one embodiment, PTC2 encompasses homologs. Moreover, the context in which the term is used will determine whether PTC2 is a nucleic acid, a protein or either.

Also provided herein is a nucleic acid encoding an IRE1 protein having unfolded protein response modulating activity and having at least 60% similarity to an amino acid sequence as shown in FIG. 26 or FIG. 27. In preferred embodiments the IRE1 protein has at least 70%, preferably at least 80%, more preferably at least 90% or even more preferably at least 95% similarity to said amino acid sequences. In one aspect, IRE1 has an amino acid or nucleic acid sequence as shown in FIG. 26 or FIG. 27. It is understood that as used herein, IRE1, Ire1 and IreA can be used interchangeably, and that in one embodiment, IRE1 includes homologs. Moreover, the context in which the term is used will determine whether IRE1 is a nucleic acid, a protein or either.

The nucleic acids provided herein may be obtained from a variety of sources including but not limited to filamentous fungi such as *Trichoderma* and *Aspergillus*. In a preferred embodiment the nucleic acids are obtained from *T. reesei, A. nidulans* or *A. niger*.

Also provided herein is a cell containing a heterologous nucleic acid encoding a protein having unfolded protein response modulating activity and a heterologous nucleic acid encoding a protein of interest to be secreted. In one aspect, said protein having unfolded protein response modulating activity is selected from the group consisting of HAC1, PTC2 and IRE1. In another embodiment, said protein of interest is selected from the group consisting of lipase, cellulase, endoglucosidase H, protease, carbohydrase, reductase, oxidase, isomerase, transferase, kinase, phosphatase, alpha-amylase, glucoamylase, lignocellulose hemicellulase, pectinase and ligninase.

Further aspects of the invention will be understood by the skilled artisan as further described below.

BRIEF DESCRIPTION OF THE FIGURES

FIG. 7 depicts an embodiment of a nucleotide (SEQ ID No. 1) and deduced amino acid sequence (SEQ ID No. 2) of *T. reesei* HAC1. The introns are shown in lower case letters.

FIG. 8 depicts an embodiment of a nucleotide (SEQ ID No. 3) and deduced amino acid sequence (SEQ ID No. 4) of *Aspergillus nidulans* (*A. nidulans*) hacA. The introns are shown in lower case letters.

FIG. 10 depicts an amino acid sequence alignment of the *T. reesei* HAC1 (SEQ ID No: 2), *A. nidulans* hacA (SEQ ID No: 4) and *S. cerevisiae* HAC1 (SEQ ID No: 60) proteins. Identical amino acids are shown by asterisks and similar ones by dots. Yeast HAC1 is homologous to the other sequences at the DNA binding domain area. The DNA binding domain is approximately at amino acids 84-147 for *T. reesei* (SEQ ID No: 5) and approximately at amino acids 53-116 for *A. nidulans* (SEQ ID No: 6).

FIG. 15 depicts complementation of *S. cerevisiae* HAC1 and IRE1 disruptions (DHAC1 and DIRE1, respectively) with different forms of the *T. reesei* HAC1 cDNA. The growth of transformants on media with and without inositol is shown. pAJ401 is the expression vector without any insert. pMS131 has the full-length *T. reesei* HAC1 cDNA in pAJ401. pMS132 has the *T. reesei* HAC1 cDNA without its 5' flanking region in pAJ401.

FIG. 24 depicts an embodiment of a nucleotide (SEQ ID No. 7) and deduced amino acid sequence (SEQ ID No. 8) of the fragment isolated from the *A. nidulans* ptcB gene. The intron is shown in lower case.

FIG. 25 depicts an embodiment of a nucleotide (SEQ ID No. 9) and deduced amino acid sequence (SEQ ID No. 10) of the *T. reesei* ptc2 cDNA.

FIG. 26 depicts an embodiment of a nucleotide (SEQ ID No. 11) and deduced amino acid sequence (SEQ ID No. 12) of the fragment isolated from the *A. nidulans* ireA gene. The intron is shown in lower case.

FIGS. 27A-27C depict an embodiment of a nucleotide (SEQ ID No. 13) and deduced amino acid sequence (SEQ ID No. 14) of the *T. reesei* IRE1 gene. The intron is shown in lower case.

FIG. 28A-28C. The nucleotide (SEQ ID No. 15) and deduced amino acid sequence (SEQ ID No. 16) of *Aspergillus niger* var. *awamori* hacA cDNA. The 20 bp unconventional intron (SEQ ID No. 17) is shown in lower case letters. The amino acid sequences of the upstream open reading frame (SEQ ID No. 18) and the HACA protein (SEQ ID No. 19) are shown below the nucleotide sequence.

DETAILED DESCRIPTION OF THE INVENTION

Figure 1:
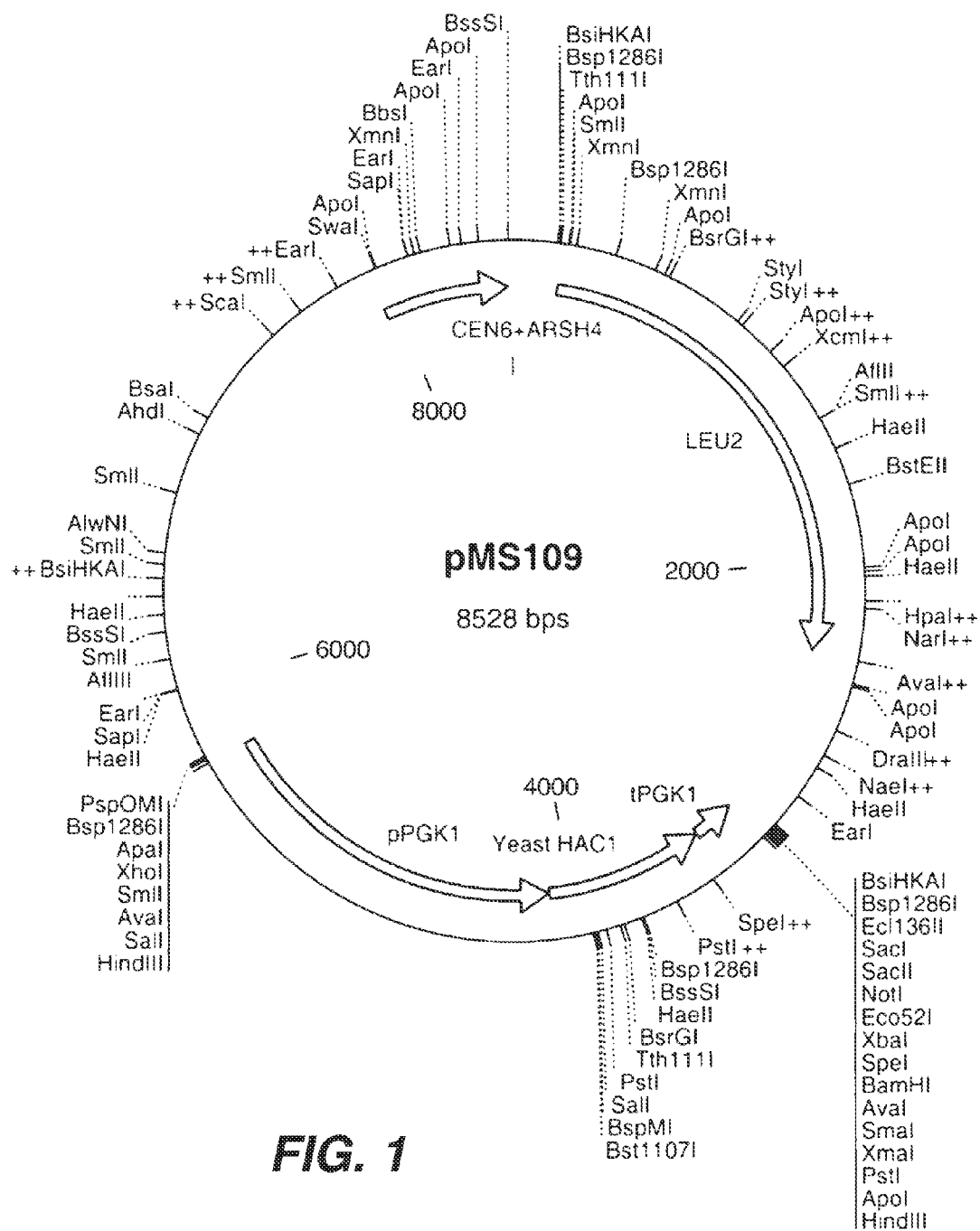
FIG. 1 depicts a map of the plasmid pMS109, an embodiment of a plasmid constructed for the expression of the truncated yeast HAC1 gene.

The invention will now be described in detail by way of reference only using the following definitions and examples.

All patents and publications, including all sequences disclosed within such patents and publications, referred to herein are expressly incorporated by reference.

Provided herein are methods and compositions for increasing the secretion of a protein in a cell comprising inducing an elevated unfolded protein response (UPR). The compositions provided herein include nucleic acids, proteins, and cells.

In one embodiment UPR refers to the unfolded protein response which occurs in response to an increase in unfolded protein in the ER. In a method provided herein, the UPR is elevated. In one embodiment, "elevated" UPR refers to an increase in the response compared to the response which would have been induced based on the amount of unfolded protein in the ER. In one embodiment, elevated refers to an increase with respect to the length of time the response occurs. In each embodiment, the elevated UPR results in an increased capacity for the cell to produce secreted proteins compared to another cell of the same type containing the same amount of unfolded protein in the ER. Preferably, the cell having an elevated UPR in accordance with the present invention produces more secreted protein in the same amount of time as a cell not having an elevated UPR.

In one aspect, the method includes inducing the elevated UPR by modulating the amount or presence of one or more UPR modulating proteins in said cell. In one embodiment, the UPR modulating protein is selected from the group consisting of HAC1, PTC2 or IRE1. UPR modulating proteins are further discussed below. It is understood that the modulating protein can be obtained by increasing the presence of a nucleic acid which encodes a modulating protein. The protein used in the methods herein have UPR modulating activity as further discussed below, and the nucleic acids encode a protein which has UPR modulating activity. Modulating means that an increase in the protein can lead to an increase or a decrease in the UPR. Thus, in one embodiment, the presence of a modulating protein is increased as further discussed below to reach an elevated UPR. In another embodiment, the modulating protein is decreased or eliminated to reach an elevated UPR. In a preferred embodiment, HAC1 and/or IRE1 are increased so as to reach an elevated UPR.

In one embodiment, inducing UPR means that the unfolded protein response as a whole is induced or maintained as it would be by unfolded protein in the ER. The unfolded protein response involves increased expression and regulation of multiple ER foldases and chaperones. Thus, in one embodiment, manipulation of ER foldases or chaperones on an individual gene basis would not be considered an induction of UPR. Thus, in a preferred embodiment, UPR modulating activity results in an elevated UPR wherein an elevated UPR results in upregulation of ER chaperones and foldases and increased secretion of proteins.

The nucleic acids encoding the UPR modulating proteins can be obtained from a variety of sources. Preferred organisms include but are not limited to *Saccharomyces cerevisiae*, *Aspergillus* spp. and *Trichoderma* spp. Also other suitable yeasts and other fungi, such as *Schizosaccharomyces pombe*, *Kluyveromyces lactis*, *Pichia* spp., *Hansenula* spp., *Fusarium* spp., *Neurospora* spp. and *Penicillium* spp. can be used. Homologous genes from other organisms can also be used. In one aspect, homologous genes refer to genes which are related, but not identical, in their DNA sequence and/or perform the same function are homologous with each other and are called each other's homologues.

HAC1, PTC2, or IRE1 amino acid and nucleic acid sequences have been described for yeast. For example, for HAC1, see GenBank accession number E15694; for PTC2, see GenBank accession number U72498; for IRE1, see Gen- Bank accession number Z11701. Sequences of GenBank accession numbers are incorporated herein by reference. GenBank is known in the art, see, e.g., Benson, D A, et al., Nucleic Acids Research 26:1-7 (1998) and http://www.ncbi.nlm.nih.gov/. In one embodiment, HAC1, PTC2, or IRE1 are isolated from a species other than yeast, preferably a filamentous fungi, insect cell, mammalian cell or other eukaroyote. Sequences for HAC1 are provided in FIGS. 7, 8 and 28. Sequences for PTC2 are provided in FIGS. 24 and 25. Sequences for IRE1 are provided in FIGS. 26 and 27.

In one embodiment, the UPR modulating sequences are identified by hybridization to other nucleic acids. Additionally, sequence homology determinations can be made using algorithms.

Thus in one embodiment, the UPR modulating nucleic acid hybridizes to a complement of a nucleic acid encoding HAC1, PTC2 or IRE1. In one embodiment, the HAC1, PTC2 or IRE1 encoding sequence is selected from the sequences provided in the respective figures. In one embodiment the stringency conditions are moderate. In another embodiment, the conditions used are high stringency conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

Homologous (similar or identical) sequences can also be determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm then performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protein such as a protease if the smallest sum probability in a comparison of the test amino acid sequence to a protein such as a protease amino acid sequence is less than about 0.1, more preferably less than about 0.01, and most preferably less than about 0.001.

In one embodiment, the HAC1 protein provided herein has less than 80% sequence similarity than the HAC1 yeast protein, see for example, GenBank accession number E15694, more preferably, less than 70%, more preferably, less than 60%, more preferably less than 50%, more preferably, less than 45% or 40% similarity. In another embodiment, identity is substituted for similarity.

In another embodiment, the HAC1 protein provided herein has at least 40% similarity to the amino acid sequence set forth in FIG. 7 or FIG. 8. More preferably, the similarity is at least 50%, more preferably, at least 60%, more preferably at least 70%, more preferably at least 80%, more preferably at least 90%, and more preferably at least 95% or 98%. In another embodiment, identity is substituted for similarity.

In another embodiment, the HAC1 protein provided herein comprises a DNA binding domain that has at least 70% similarity to the DNA binding domain set forth in FIG. 10. More preferably, the similarity is at least 70%, more preferably at least 80%, more preferably at least 90%, and more preferably at least 95% or 98%. In another embodiment, identity is substituted for similarity.

As used herein, DNA binding domain refers to the domain which binds to the conserved sequence called the UPR element in promoters of genes regulated by UPR. Embodiments of a DNA binding region are shown approximately at amino acids 84-147 of the *T. reesei* protein shown in FIG. 10, approximately at amino acids 53-116 of the *A. nidulans* protein shown in FIG. 10 and approximately amino acids 45-109 of the *A. niger* protein shown in FIG. 28. HAC1 homologs will have DNA binding domains which can be identified by activity or by alignment to the binding domains in FIG. 10.

In one embodiment, the PTC2 protein provided herein has less than 80% sequence similarity than the PTC2 yeast protein, see for example, GenBank accession number U472-498, more preferably, less than 70%, more preferably, less than 60%, more preferably less than 50%, more preferably, less than 45% or 40% similarity. In another embodiment, identity is substituted for similarity.

In another embodiment, the PTC2 protein provided herein has at least 40% similarity to the amino acid sequence set forth in FIG. 24 or FIG. 25. More preferably, the similarity is at least 50%, more preferably, at least 60%, more preferably at least 70%, more preferably at least 80%, more preferably at least 90%, and more preferably at least 95% or 98%. In another embodiment, identity is substituted for similarity.

In one embodiment, the IRE1 protein provided herein has less than 80% sequence similarity than the IRE1 yeast protein, see for example, GenBank accession number Z11701, more preferably, less than 70%, more preferably, less than 60%, more preferably less than 50%, more preferably, less than 45% or 40% similarity. In another embodiment, identity is substituted for similarity.

In another embodiment, the IRE1 protein provided herein has at least 40% similarity to the amino acid sequence set forth in FIG. 26 or FIG. 27. More preferably, the similarity is at least 50%, more preferably, at least 60%, more preferably at least 70%, more preferably at least 80%, more preferably at least 90%, and more preferably at least 95% or 98%. In another embodiment, identity is substituted for similarity.

Additionally, further homologs of the UPR modulating sequences can be identified for example by using PCR primers based on the sequences provided herein. In yet another embodiment, naturally occurring allelic variants of the sequences provided herein may be used.

A protein has UPR modulating activity if it is able to regulate the induction of UPR. Regulate means causing an increase or decrease in the induction of the UPR. A UPR modulating protein can increase or decrease UPR induction whether or not there is a change in the amount unfolded protein in the ER. In a preferred embodiment, a UPR modulating protein has one or more of the following activities: HAC1 activity, PTC2 activity, IRE1 activity, or binds to HAC1.

Modulating the amount of or activity of the UPR modulating protein can occur by a variety of methods. For example, to increase the presence or activity of a protein in a cell, one can over-express the nucleic acid encoding the UPR modulating protein. Over-expression as used herein means that the protein encoded by the said gene is produced in increased amounts in the cell. In one embodiment, over-expression can be used interchangeably with constitutive expression or upregulation. This can be achieved by increasing the copy number of the gene by introducing extra copies of the gene into the cell on a plasmid or integrated into the genome. Over-expression can also be achieved by placing the gene under a promoter stronger than its own promoter. The amount of the protein in the cell can be varied by varying the copy number of the gene and/or the strength of the promoter used for the expression. Thus, manipulation of genes to cause induction of UPR may involve insertion into the host of multiple copies of a gene with its native promoter either on a replicating autosomal plasmid or by integration into the chromosomal DNA. It may involve fusion of the gene with a promoter region and/or transcriptional control sequences from other genes to further increase expression or to allow controlled, inducible expression. Agonists and enhancers may also be used.

In the case where it is desired to reduce the activity of a UPR modulating protein to result in elevated UPR, a number of methods may be used such as deletion of a gene or the use of antisense nucleic acids to reduce the expression of a gene. It may involve alteration of a gene to provide a mutant form of the protein or include the use of an inhibitor of a UPR modulating protein.

In one embodiment, UPR is elevated by using a UPR inducing form of a recombinant nucleic acid encoding a UPR-modulating protein. In one embodiment, a UPR-inducing form of a recombinant nucleic acid encoding a UPR-modulating protein is a nucleic acid which has been modified to give rise to a translatable mRNA. The translatable form mimics the modified mRNA which appears in the cell on induction of UPR and which can be translated to an active UPR-modulating protein.

In one embodiment, a UPR-inducing form of a recombinant nucleic acid includes coding sequence. Coding sequence as used herein includes the nucleic acid sequence which leads to the amino acid sequence of the protein in its active form. As used herein, a nucleic acid consisting essentially of a coding sequence explicitly excludes, lacks or omits at least internal sequence which does not get translated when the active protein is encoded. Internal sequence as used herein refers to sequence which is internal to the carboxyl terminus and the amino terminus. Examples of excluded internal sequence are shown in small letters in FIGS. 7, 8, 24, 26, 27 and 28. The sequence may be excluded by deletion or truncation by methods known in the art.

In one embodiment a nucleic acid comprises a sequence consisting essentially of coding sequence. In this embodiment, the nucleic acid may comprise vector sequence on either side of the coding sequence but the coding sequence excludes internal sequence which does not get translated in the encoded protein's active form.

In another embodiment, a UPR modulating protein is a variant UPR modulating protein which has been varied to have increased activity. Thus in one embodiment, the activity of a UPR modulating protein is increased to elevate UPR. In one embodiment, the activity of a UPR modulating protein is increased by maintaining the protein in its active state. For example, IRE1 is phosphorylated when the UPR pathway is turned on. Therefore, in one embodiment herein, maintaining IRE1 in its phosphorylated induces an elevated UPR.

In a preferred embodiment, IRE1 is mutated so as to constitutively have the activity of phosphorylated IRE1. In one embodiment, serine and/or threonine residues are substituted with aspartic acid to form to form an IRE1 variant having constitutive UPR inducing activity. Other substitutions to mimic a protein in its phosphorylated state are known in the art. Preferably, the mutations are performed on the nucleic acid encoding the protein.

By the term "recombinant nucleic acid" herein is meant nucleic acid, originally formed in vitro, in general, by the manipulation of nucleic acid by polymerases and endonucleases, in a form not normally found in nature. Generally, a nucleic acid refers to DNA, RNA or mRNA and includes a gene or gene fragment. Thus, an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. Generally, the term protein and peptide can be used interchangeably herein. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. In one embodiment, the definition includes the production of a protein from other than its host cell, or produced by a recombinant nucleic acid. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

A recombinant cell generally refers to a cell which has been manipulated to contain a recombinant nucleic acid or protein therein.

The protein of interest to be secreted can be any protein. Wherein the protein is not naturally secreted, the nucleic acid encoding the protein may be modified to have a signal sequence in accordance with techniques known in the art. The proteins which are secreted may be endogenous proteins which are expressed naturally, but in a greater amount in accordance with the present invention, or the proteins may be heterologous. In a preferred embodiment, the proteins are heterologous. Heterologous as used herein means the protein is produced by recombinant means. Therefore, the protein may be native to the cell, but is produced, for example, by transformation with a self replicating vector containing the nucleic acid encoding the protein of interest. Alternatively, recombinant could be wherein one or more extra copies of the nucleic acid are integrated into the genome by recombinant techniques.

In another embodiment, the protein of interest is selected from the group consisting of lipase, cellulase, endo-glucosidase H, protease, carbohydrase, reductase, oxidase, isomerase, transferase, kinase, phosphatase, alpha-amylase, glucoamylase, lignocellulose hemicellulase, pectinase and ligninase. In another embodiment, the protein of interest is a therapeutic selected from the group consisting of vaccines, cytokines, receptors, antibodies, hormones, and factors including growth factors.

The cell in which the proteins are secreted is any cell having an upregulated protein response. Preferably, the host to be transformed with the genes of the invention can be any eukaryotic cell suitable for foreign or endogenous protein production, e.g., any *S. cerevisiae* yeast strain, (e.g., DBY746, BMA64-1A, AH22, S150-2B, GYPY55-15bA, vtt-a-63015) any *Trichoderma* spp. such as *T. longibrachiatum* and the *T. reesei* strains derived from the natural isolate QM6a, such as RUTC-30, RL-P37, QM9416 and VTT-D-79125, any *Kluyveromyces* spp/. *Sch. pombe, H. polymorpha, Pichia, Aspergillus, Neurospora, Yarrowia, Fusarium, Penicillium* spp. or higher eukaryotic cells.

Examples of mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/–DHFR(CHO, Urlaub and Chasin, *Proc. Natl. Acad. Sci. USA,* 77:4216 (1980)); mouse sertoli cells (TM4, Mather, *Biol. Reprod.,* 23:243-251 (1980)); human lung cells (W138, ATCC CCL 75); human liver cells (Hep G2, HB 8065); and mouse mammary tumor (MMT 060562, ATCC CCL51).

In an alternative embodiment, a plant cell can be utilized. In another embodiment, a baculovirus infected insect cell is utilized. The selection of the appropriate host cell is deemed to be within the skill in the art.

Transfer of the genes into these cells can be achieved, for instance, by using the conventional methods of transformation described for these organisms. General aspects of mammalian cell host system transfections have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci. (USA*), 76:3829 (1979). However, other methods for introducing DNA into cells, such as by nuclear microinjection, electroporation, etc. For various techniques for transforming mammalian cells, see Keown et al., *Methods in Enzymology,* 185:527-537 (1990) and Mansour et al., *Nature,* 336: 348-352 (1988).

The nucleic acid (e.g., cDNA, coding or genomic DNA) encoding the UPR modulating protein may be inserted into a replicable vector. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Req.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Transcription from vectors in mammalian host cells can be controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the protein in eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the protein. Still other methods, vectors, and host cells are described in Gething et al., *Nature*, 293:620-625 (1981); Mantei et al., *Nature*, 281:40-46 (1979); EP 117,060; and EP 117,058.

In one embodiment, the gene is cloned into a suitable expression vector, such as pKK1 or similar vectors comprising the appropriate regulatory regions depending on the selected host. For example, these regulatory regions can be obtained from yeast genes such as the ADH1, GAL1-GAL 10, PGK1, CUP1, GAP, CYC1, PHO5, or asparagine synthetase gene, for instance. Alternatively, also the regulatory regions of, for example, HAC1 can be used to express the gene in *S. cerevisiae*. The plasmid carrying the gene is capable of replicating autonomously when transformed into the recipient yeast strain and is maintained stably in a single copy due to the presence of a yeast centromeric sequence. Alternatively, a multicopy replicating plasmid could be used or integration of the plasmid into the yeast genomic DNA could be provided for using methods known in the art.

In one embodiment herein, to express HAC1 cDNA, preferably truncated in *Trichoderma* the coding region of the inducing form of the *Trichoderma* HAC1 gene is coupled for instance between the *A. nidulans* gpdA promoter and terminator and the expression cassette is transformed into a *Trichoderma* strain producing for instance bovine chymosin or another foreign protein. In the truncated form, the unconventional introns are removed, as well as any remaining terminal end adjacent to said intron. An unconventional intron is one which is present in the mRNA in the cell which is not undergoing UPR, but which is removed from the mRNA upon induction of the UPR. UPR would be thus induced constitutively. A higher level of expression which was inducible according to the carbon source used for growth of the fungus could be achieved by fusion of the inducing form of HAC1 with the promoter of the *T. reesei* cbh1 gene.

For filamentous fungi the HAC1 gene is preferably integrated into the genome using methods known in the art. Suitable promoters in addition to the gpdA or cbh1 promoters or promoter of the HAC1 gene itself are for instance the other cellulase promoters, cbh2, egl1, egl2, or tef1, pgk, pki, the glucoamylase, alpha-amylase or the alcohol dehydrogenase promoter. In filamentous fungi transformation usually results in strains with varying copies of expression vector integrated into the genome (Penttilä et al., 1987) and from these the strain with optimal level of truncated HAC1 expression for growth and enhanced secretion can be screened.

It is understood that the methods provided herein may further include cultivating said recombinant host cells under conditions permitting expression of said secreted protein. The proteins can be collected and purified as desired. In a preferred embodiment, hydrolytic enzymes are secreted. In another embodiment, the secreted proteins are used in improved alcohol production or in processes where efficient hydrolysis of raw material is desired.

The following preparations and examples are given to enable those skilled in the art to more clearly understand and practice the present invention. They should not be considered as limiting the scope and/or spirit of the invention, but merely as being illustrative and representative thereof.

Example 1

Effect of Expression of Truncated HAC1 in Yeast

In order to cause constitutive induction of the unfolded protein response in *Saccharomyces cerevisiae*, a truncated version of the yeast HAC1 gene was expressed from a centromeric plasmid. The truncated version does not include the intron of HAC1 that in normal conditions prevents the translation of the mRNA. Thus the mRNA expressed from the plasmid is translated to HAC1 protein constitutively and causes a constitutive induction of the unfolded protein response. The appropriate HAC1 gene fragment was first amplified from yeast chromosomal DNA by PCR. This fragment starts 24 by before the translation start codon of the HAC1 gene and ends with a translation stop codon inserted after the proline codon at amino acid position 220 of the deduced protein. The oligonucleotide primers used were: 5' ATC GCA GGA TTC CCA CCT ACG ACA ACA ACC GCC ACT 3 (forward primer) (SEQ ID No. 20) and 5' TAC AGC GGA TCC CTA TGG ATT ACG CCA ATT GTC AAG3' (reverse primer) (SEQ ID No. 21). BamHI restriction sites were included into both of the primers to facilitate cloning. The PCR reaction was carried out with the Vent DNA polymerase (New England Biolabs) in conditions recommended by the manufacturer. The PCR program used started with heating to 94° C. for three minutes followed by 30 cycles with denaturation at 94° C. for 45 seconds, annealing at 55° C. for 45 seconds and synthesis at 72° C. for one minute. The PCR product fragment of 690 by was run in a 0.8% agarose gel and purified from the gel by the Qiaquick gel extraction kit (Qiagen) according to manufacturer=s protocol. The fragment was digested with BamHI and cloned into the BamHI site of the pZERO vector (Invitrogen) with methods known in the art. The HAC1 fragment was released from pZERO by BamHI digestion and cloned into the BgIII site of the vector pKK1 between the promoter and terminator of the yeast PGK1 gene with methods known in the art. pKK1 contains the LEU2 selectable marker gene and the centromere (CEN6) and ARS sequences for maintenance in yeast as a single-copy plasmid. The final expression plasmid was named pMS109 (FIG. 1).

Figure 2:
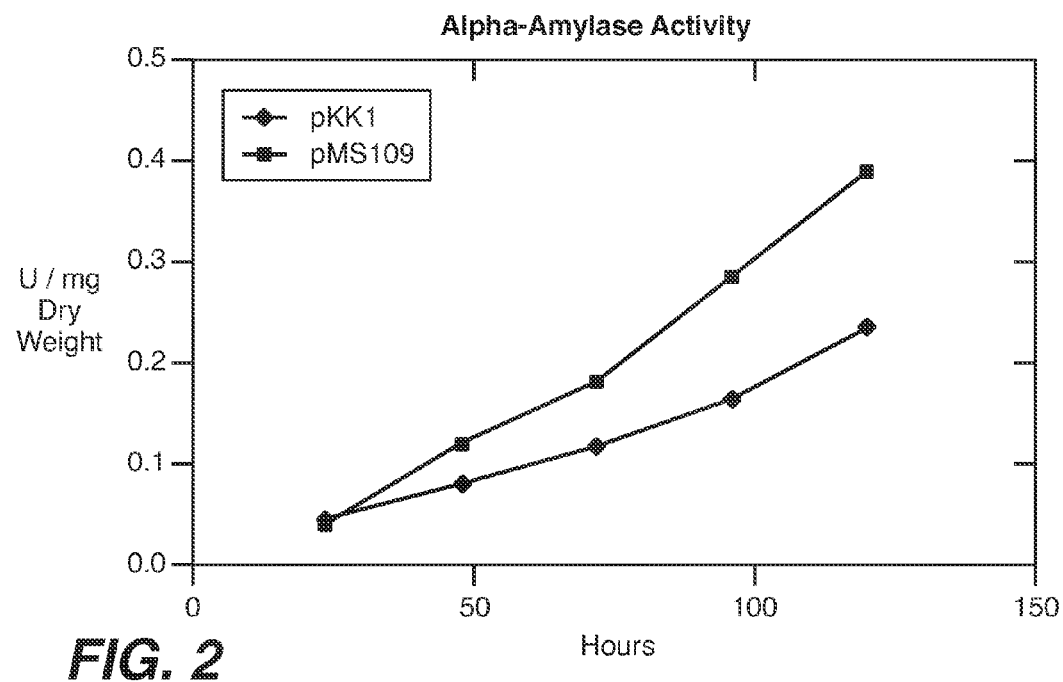
FIG. 2 depicts a graph showing activity of α-amylase produced from yeast containing pMS109 (squares) or an empty control vector pKK1 (diamonds) in the vertical bar, over time, horizontal bar, and further showing the activity is greater wherein pMS109 is present.

The plasmid pMS109 and the control plasmid pKK1 were transformed into a yeast strain producing *Bacillus amyloliquefaciens* α-amylase. In this strain, the expression cassette with the α-amylase coding region inserted between the yeast ADH1 promoter and terminator had been integrated into the TRP1 locus of the yeast strain DBY746 (α, his3 1, leu2-3, ura3-52, trp1-289, Cyh$^r$). Four pMS109 transformants and four strains transformed with the vector pKK1 were selected for cultivations. The cultivation medium was synthetic complete yeast medium without leucine (SC-Leu, described by Sherman 1991, *Meth. Enzymol.* 194, 3-21), buffered to pH 6.0 with 2% succinic acid and supplemented with 2% glucose as the carbon source. The 50 ml yeast shake flask cultures were inoculated to the initial OD600 (optical density at the wavelength of 600 nm) of 0.2 and growth was carried out for five days at 30° C. and 250 RPM. Samples were taken daily for monitoring yeast growth and α-amylase production. α-amylase activity was measured with the Phadebas Amylase Test (Pharmacia) according to the instructions of the manufacturer. Yeast cell density was determined by measuring OD600 (optical density at the wavelength of 600 nm) of the culture. The α-amylase amounts produced by each of the pMS109 transformants were higher than the amounts produced by any of the pKK1 transformants. The average production level of pMS109 transformants was 70% higher in the end of the cultivation than the average of pKK1 clones (FIG. 2). The growth of the pMS109 strains was slightly retarded when compared with the control.

Figure 3:
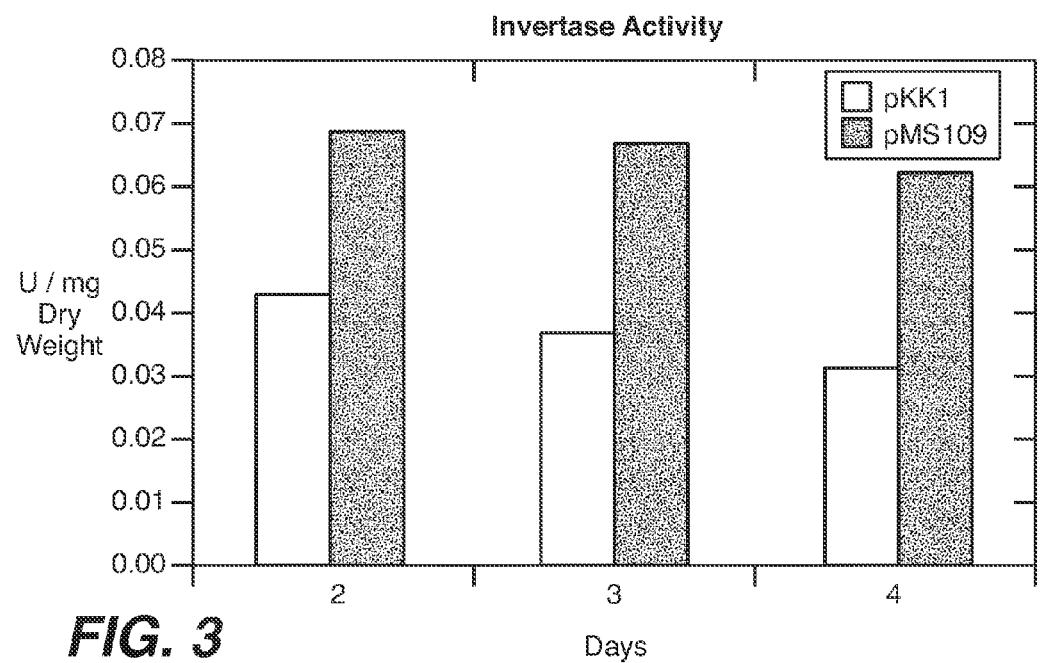
FIG. 3 depicts a bar graph showing activity of invertase produced from yeast containing pMS109 (black bars) or an empty control vector pKK1 (shaded bars) in the vertical bar, overtime, horizontal bar, and further showing the activity is greater wherein pMS109 is present.

To analyse the effect of the constitutive UPR induction to yeast invertase production, four clones transformed with pMS109 and four clones transformed with the pKK1 vector, derived from the α-amylase producing strain described above, were cultivated in the SC-Leu medium buffered to pH 6.0 with 2% succinic acid and containing 2% sucrose as the carbon source. The 50 ml shake flask cultures were inoculated to the initial OD600 of 0.2 and grown subsequently for five days at 30° C. and 250 RPM. Yeast growth was followed by measuring the OD600 and samples were taken for invertase assays on days three, four and five. For each assay, cells were harvested by centrifugation from 1 ml of the culture. The cells were washed with 5 ml of 10 mM $NaN_3$ and resuspended in 0.2 M NaAc buffer, pH5.0 with 10 mM $NaN_3$. The invertase activity of the cells was measured by incubating them with 0.166 M sucrose in 0.2 M NaAc buffer, pH 5.0 for 6 minutes. The reaction was stopped by adding one volume of 0.5 M $KPO_4$, pH 7.0 and by separating the cells rapidly from the reaction mixture by filtration. The glucose formed into the reaction mixture was measured by the GOD-Fend kit (Boehringer Mannheim) according to the manufacturers protocols. The invertase production of the pMS109 transformants was about 2 times higher than that of the pKK1 transformants in all the timepoints that were tested (FIG. 3).

Example 2

Effect of Disruption of HAC1 in Yeast

The yeast HAC1 gene was disrupted by replacing it in the genome with a DNA fragment containing the G418 antibiotic resistance cassette flanked by 48 by sequences from the 5' and 3' ends of the HAC1 open reading frame. The G418 resistance cassette consists of the *E. coli* kanamycin resistance gene cloned between the promoter and terminator of the *Ashbya gossypii* TEF gene encoding translation elongation factor 1. The DNA fragment used in the disruption of the yeast HAC1 was produced by PCR from the kanMX2 module (Wach et al., 1994, *Yeast* 10, 1793-1808) with the oligonucleotide primers 5' CCA CCT ACG ACA ACA ACC GCC ACT ATG GAA ATG ACT GAT TTT GAA CTA CTT GCC TCG TCC CCG CCG GGT CAC 3' (forward primer) (SEQ ID No. 22) and 5' AAT TAT ACC CTC TTG CGA TTG TCT TCA TGA AGT GAT GAA GAA ATC ATT GAC ACT GGA TGG CGG CGT TAG TAT CGA 3' (reverse primer) (SEQ ID No. 23). The PCR reaction was done with the Dynazyme DNA polymerase (Finnzymes) in conditions recommended by the manufacture. The PCR program started by denaturation at 94° C. for 3 minutes, followed by 30 cycles of denaturation at 94° C. for 45 seconds, annealing at 52° C. for 30 seconds and elongation at 72° C. for 1 minute. A final elongation step of 5 minutes was performed at 72° C. The PCR product of about 1.5 kb was run in an 0.8% agarose gel and purified from the gel with the Qiaquick kit (Qiagen). The fragment was transformed into the yeast strain BMA64-1A (a, ura3-1, trp1-Δ, leu2-3, 112, his3-11, ade2-1, can1-100) with a method described (Gietz et al., 1992, *Nucl. Acids Res.* 20, 1425). The transformants were first grown over night on YPD plates (Sherman, 1991, *Meth. Enzymol.* 194, 3-21) and then replicated onto YPD plates with 200 µg/ml of the antibiotic G418. The transformants resistant to G418 were tested on plates with yeast mineral medium (Verduyn et al, 1992, *Yeast* 8, 501-517) with and without inositol. Chromosomal DNA was isolated from strains that were dependent on inositol, and Southern hybridization with the HAC1 protein-coding region was performed with methods known in the art. The result of the hybridization showed that the HAC1 gene had been disrupted in the strains dependent on inositol.

Figure 4:
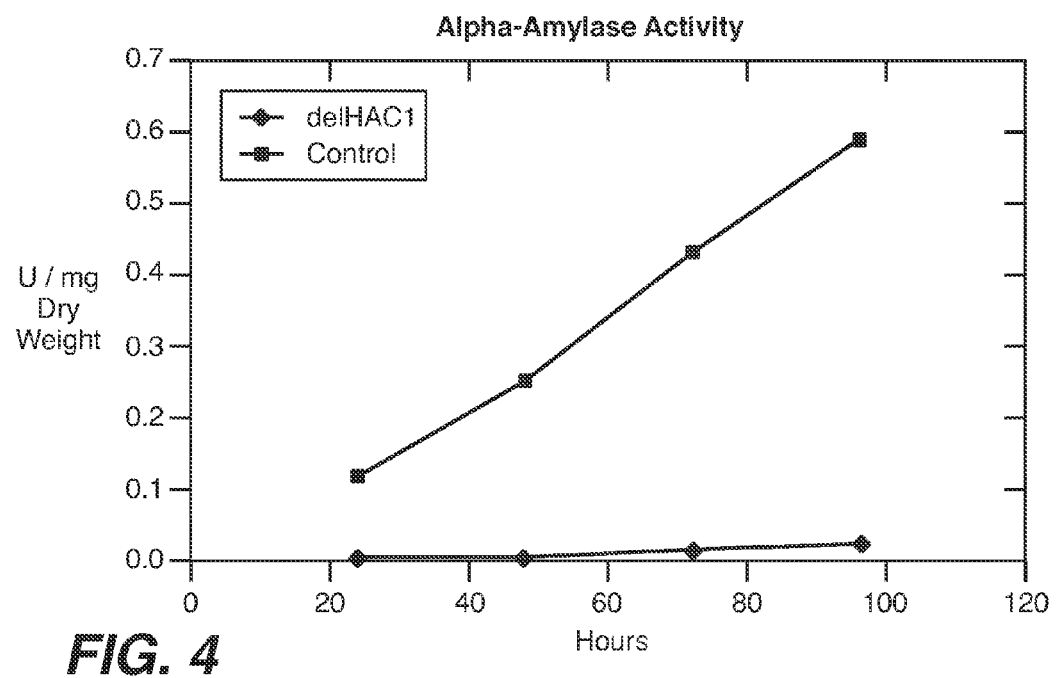
FIG. 4 depicts a graph showing activity of α-amylase produced from yeast wherein HAC1 has been disrupted (diamonds) or from its parental control strain (squares) in the vertical bar, over time, horizontal bar, and further showing that the activity is greater wherein HAC1 has not been disrupted.
Figure 5:
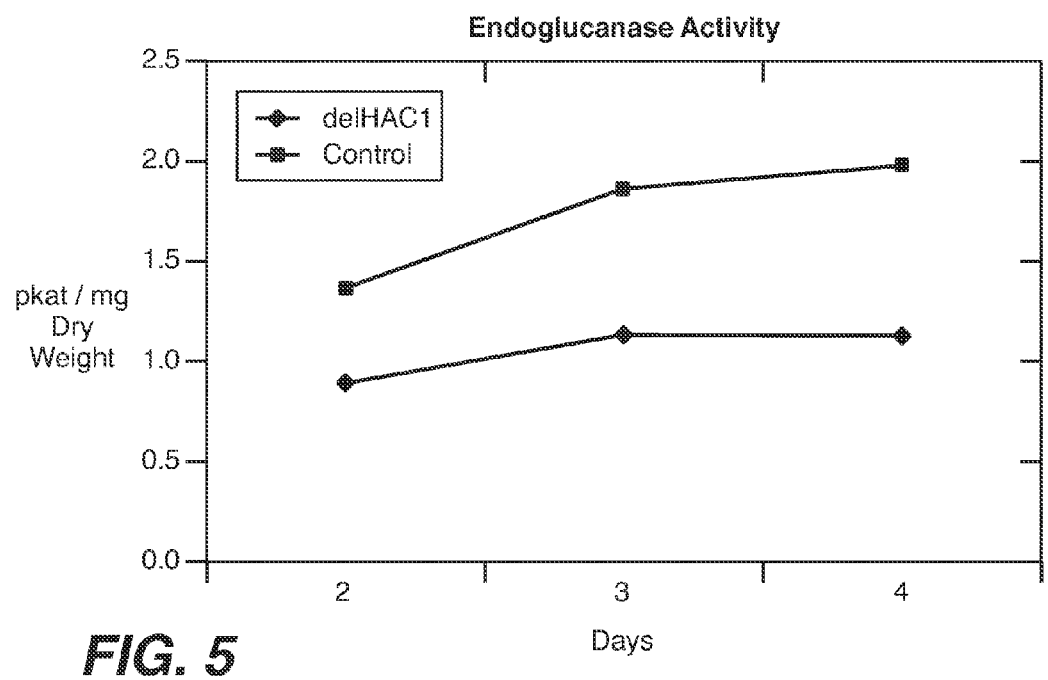
FIG. 5 depicts a graph showing activity of *Trichoderma reesei* (*T. Reesei*) endoglucanase EGI produced from yeast wherein HAC1 has been disrupted (diamonds) or from its parental control strain (squares) in the vertical bar, over time, horizontal bar, and further showing that the activity is greater wherein HAC1 has not been disrupted.

The effect of the HAC1 disruption on the production of two heterologous proteins, the *Bacillus amyloliquefaciens* α-amylase (Ruohonen et al., 1987, *Gene* 59, 161-170) and the *Trichoderma reesei* endoglucanase EGI (Penttilä et al., 1987, *Yeast* 3, 175-185), was tested. The α-amylase was expressed from a multicopy plasmid with the LEU2 marker gene, B485 (Ruohonen et al., 1991, *J. Biotechnol.* 39, 193-203, the plasmid is called YEpαα6 in this article), where the α-amylase gene has been cloned between the yeast ADH1 promoter and terminator. The EGI was expressed from the plasmid pMP311 (Penttilä et al., 1987, *Yeast* 3, 175-185), where the endoglucanase cDNA has been cloned between the yeast PGK1 promoter and terminator in a multicopy vector with the LEU2 marker gene. The B485 and pMP311 plasmids were transformed into the HAC1 disruptant and its parental strain with a described method (Gietz et al., 1992, *Nucl. Acids Res.* 20, 1425), and transformants were selected on SC-Leu plates (Sherman, 1991, *Meth. Enymol.* 194, 3-21). Three B485 transformants derived both from the HAC1 disruptant and its parental strain were grown in 50 ml shake flask cultures in SC-Leu buffered to pH 6.0 with 2% succinic acid and supplemented with 2% glucose. The cultures were inoculated to the initial OD600 of 0.2, and growth was continued for four days at 30° C. and 250 RPM. The α-amylase activity in the culture supernatants was assayed as described in Example 1. The HAC1 disruptant strain produced less than 10% of the α-amylase amount produced by the wild type control strain (FIG. 4). To test the effect on EGI production, three pMP311 transformants derived from the HAC1 disruptant and three transformants derived from the parental strain were grown in 50 ml of SC-Leu (Sherman, 1991, *Meth. Enzymol.* 194, 3-21) with 2% glucose in shaker flasks. The cultures were inoculated to the initial OD600 of 0.2, and grown at 30° C. and 250 RPM for four days. Endoglucanase activity of the cultures was measured with the substrate 4-methylumbelliferyl-β-D-lactoside (Sigma). Supernatant samples were incubated at 50° C. for 3 hours in a reaction mixture of 0.25 mg/ml of the substrate and 0.1 M glucose in 50 mM NaAc, pH 5.0. The reaction was stopped by adding two volumes of 1 M $Na_2CO_3$, and the absorbance of the mixture was measured at the wavelength of 370 nm. The production of the endoglucanase EGI of the HAC1 disruptant was about 50% of the level produced by the parental strain (FIG. 5).

Example 3

Cloning and Sequence of the *Aspergillus nidulans* hacA and *Trichoderma reesei* HAC1 Genes A homology search was performed against a public database (http://bioinfo.okstate.edu/pipeonline_db/anesquery.html) containing *Aspergillus nidulans* EST (expressed sequence tag) sequences with the yeast HAC1 protein sequence using the program BLAST (Altschul et al., 1990, *J. Mol. Biol.* 215, 403-410). The search identified one EST cDNA clone (c7a10a1.r1) which has homology to yeast HAC1p at the DNA binding domain. However, another region of the same cDNA clone, designated as EST c7a10a1.f1 in the database, had no obvious similarity with HAC1 and there was no annotation within the database to indicate similarity between the ESTs and HAC1. Therefore, it was unclear if the *A. nidulans* cDNA clone encoded a functional homolog of HAC1 or a different protein having a version of a DNA-binding motif. The region corresponding to the c7a10a1 EST cDNA was amplified by PCR from *A. nidulans* genomic DNA isolated with methods known in the art. The sequences of the ends of the EST cDNA clone found from the database were used to design the 5' end primer (5' GCC ATC CTT GGT GAC TGA GCC 3') (SEQ ID No. 24) and 3' end primer (5' CAA TTG CTC GCT CTT ACA TTG AAT 3') (SEQ ID No. 25). The PCR reaction was performed as described in Example 2. The PCR product of 1.6 kb in length was run in an 0.8% agarose gel, purified from the gel with the Qiaquick gel extraction kit (Qiagen) and cloned into the pGEM-AT vector (Promega) with methods known in the art. The whole fragment was sequenced from the resulting plasmid using internal oligonucleotide primers.

Figure 6:
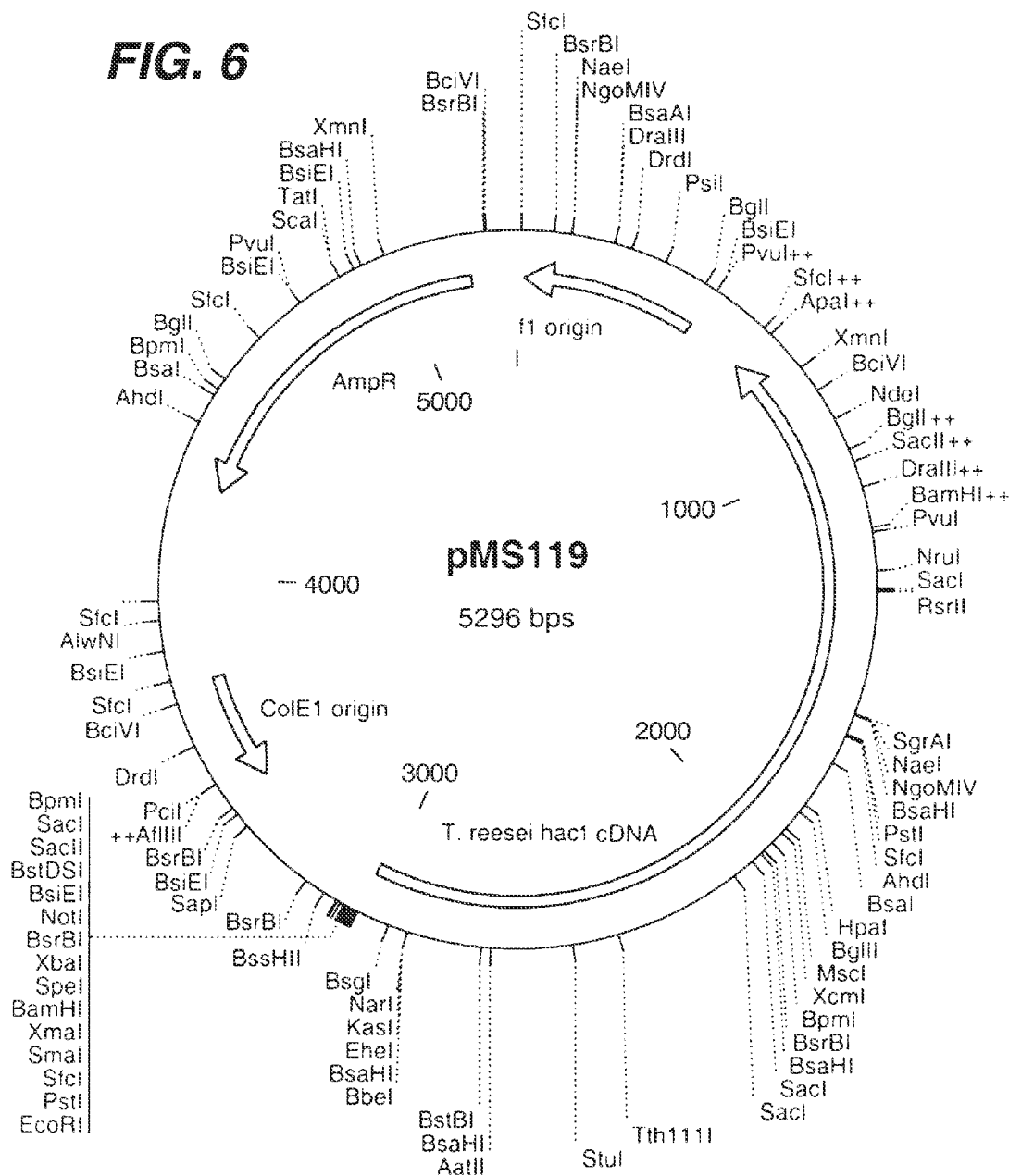
FIG. 6 depicts a map of the plasmid pMS119, where the full-length *T. reesei* HAC1 cDNA without the 20 by intron is in the pBluescript SK vector.

To isolate the HAC1 cDNA from *Trichoderma reesei*, the proper hybridisation temperature for cDNA library screening were determined by genomic Southern hybridization with the genomic hacA fragment cloned from *A. nidulans* as a probe. The probe fragment was labelled with $^{32}$P-dCTP using the Random primed DNA labelling kit (Boehringer Mannheim) as instructed by the manufacturer. The hybridization was performed as described (Sambrook et al., 1989, in *Molecular Cloning: a Laboratory Manual*, Cold Spring Harbor Laboratory, Cold Spring Harbor, N.Y.) at 48° C., 50° C., 55° C. and 60° C. in a hybridization mixture containing 6×SSC, 5×Denhardt's, 0.5% SDS, 100 µg/ml herring sperm DNA (SSC is 0.15 M NaCl, 0.015 M Na-citrate, pH 7.0, 50×Denhardt's is 1% Ficoll, 1% polyvinylpyrrolidone, 1% bovine serum albumin). The filters were washed for 10 minutes at room temperature with 2×SSC, 0.1% SDS and for 30 minutes at the hybridization temperature with the same solution. The *T. reesei* cDNA library constructed into the vector λZAP (Stratagene, Stalbrand et al., 1995, *Appl. Environ. Microbiol.* 61, 1090-1097) was plated with the appropriate *E. coli* host strain, and the λ-DNA was lifted onto nitrocellulose filters (Schleicher & Schull) as instructed by the manufacturer. Hybridization of the filters was done for 18 hours at 55° C. in the same hybridization mixture as the Southern hybridization. The filters with λ-DNA were washed for 10 minutes at room temperature with 2×SSC, 0.1% SDS and for 30 minutes at 55° C. with the same solution. The λ-clones hybridizing with the probe were excised into pBluescript plasmids containing the cDNA inserts as instructed (Stratagene). The cDNA clone carrying the largest insert (in the plasmid pMS119, FIG. 6) was chosen for sequencing, and the whole sequence of its insert was determined with the help of internal sequencing primers. The genomic copy of the *T. reesei* gene was isolated by hybridization of a genomic λ-library in the vector λEMBL3 (Kaiser and Murray, 1985, in *DNA Cloning: a Practical Approach*, pp. 1-47, ed. Glover, IRL Press, Oxford). The library was plated with the appropriate *E. coli* host strain and λ-DNA was lifted onto nitrocellulose filters (Schleicher & Schull) as instructed by the manufacturer. The filters were hybridized at 42° C. over night in a hybridization mixture containing 50% formamide, 5×Denhardt's, 5×SSPE, 0.1% SDS, 100 µg/ml herring sperm DNA and 1 µg/ml polyA-DNA (SSPE is 0.18 M NaCl, 1 mM EDTA, 10 mM $NaH_2PO_4$, pH 7.7). The filters were washed for 10 minutes at room temperature with 2×SSC, 0.1% SDS and 30 minutes at 65° C. in 0.1×SSC, 0.1% SDS. λ-DNA was isolated from clones hybridizing with the probe with a described method (Sambrook et al., 1989, in *Molecular Cloning: a Laboratory Manual*, Cold Spring Harbor Laboratory, Cold Spring Harbor, N.Y.), and the genomic region corresponding to the HAC1 cDNA was sequenced from this DNA with internal sequencing primers.

Figure 9:
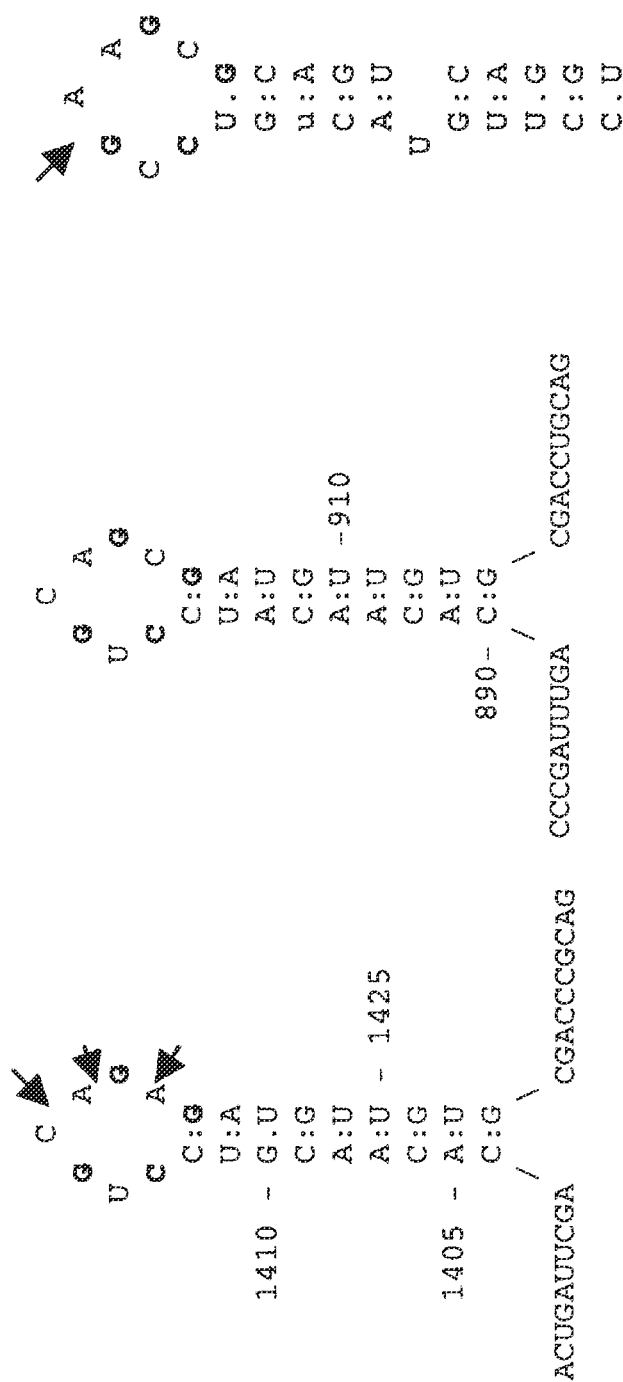
FIG. 9 depicts the hairpin loop structures forming at the 5' end of the 20 by introns in the *T. reesei* HAC1 and *A. nidulans* hacA mRNAs and at the 3' end of the intron of the *S. cerevisiae* HAC1 mRNA. The conserved nucleotides in the loop region are shown in bold. The cleavage site of the yeast intron and the three possible cleavage sites of the *T. reesei* HAC1 intron are shown by arrows. Alignment of the 20 by intron areas of the *T. reesei* HAC1 and *A. nidulans* hacA is shown below. The intron is in lower case.

The sequences of the *Trichoderma reesei* HAC1 and *Aspergillus nidulans* hacA genes are shown in FIGS. 7 and 8, respectively. Comparison of the genomic and cDNA sequences from both fungi (the cDNA sequence of hacA available in the EST database) reveals a conventional intron with consensus border sequences at a conserved position in both of the genes. A second intron of 20 by is found in the *T. reesei* HAC1 gene. This intron does not have the consensus 5' border sequence (GT). The sequence around the 5' end of this intron is predicted to have a strong tendency to form a RNA secondary structure called hairpin loop. The area between the stems of the loop has a sequence very similar to the consensus sequence found at both of the intron borders of the unconventional intron of 252 by found in yeast HAC1 (FIG. 9, Gonzalez et al., 1999, *EMBO. J.* 18, 3119-3132). When the UPR pathway is induced, the IRE1 protein cleaves the HAC1 mRNA at these intron borders, and thus initiates the splicing of the intron and formation of an active HAC1 protein. In the Aspergillus nidulans hacA gene there is a sequence almost identical to the hairpin-unconventional intron region of T. reesei HAC1.

It has been shown by RT-PCR studies that the 20 by intron is removed from the T. reesei HAC1 and A. nidulans hacA mRNAs upon UPR induction (Example 4). The 250 by intron in yeast HAC1 prevents translation of the mRNA probably by forming a specific secondary structure (Chapman and Walther, 1998, Curr. Biol. 7, 850-859). The 20 by intron in the HAC1/hacA genes of filamentous fungi can not form such secondary structures, and thus the activation mechanism of these genes is different from yeast HAC1. The T. reesei HAC1 cDNA encodes an open reading frame of 451 amino acids and the A. nidulans hacA a protein of 350 amino acids, when the 20 by introns have been removed from the both sequences. The putative T. reesei and A. nidulans HACl/A proteins have an identity of 37.4% with each other and both have a DNA binding domain conserved with yeast HAC1 protein (FIG. 10). The yeast HAC1 binding site has approximately 64% similarity and 53% identity to the binding site of T. reesei, and approximately 65% similarity and 56% identity to the binding site of A. nidulans. At other regions there is no detectable homology between yeast HAC1p and the HACI of T. reesei or the HACA of A. nidulans. The HAC1 cDNA clone sequenced from T. reesei has a 5' flanking region of 471 bp, containing two short open reading frames encoding 17 and 2 amino acids. The 5' flanking region sequenced from A. nidulans hacA is 187 by in length, containing one upstream open reading frame of 7 amino acids.

Example 4

Figure 11:
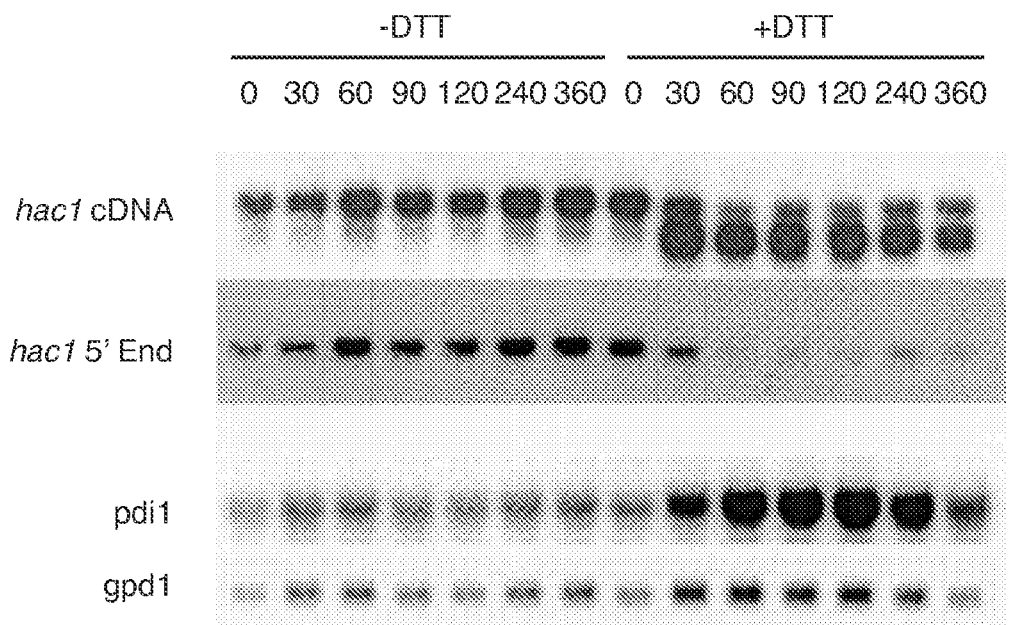
FIG. 11 depicts Northern hybridization of RNA samples derived from *T. reesei* mycelia treated with DTT (+DTT) and untreated control mycelia (−DTT). The timepoints (in minutes) after DTT addition are shown. The probes used for hybridization are shown on the left.

Demonstration of Truncation at the 5' End and Splicing of the 20 by Intron of T. reesei and A. nidulans HAC1/hacA mRNA Upon UPR Induction When the UPR pathway is induced in yeast, the unconventional intron of the HAC1 gene is spliced and thus the length of the HAC1 mRNA is reduced by 250 by (Cox and Walter, 1996, Cell 87, 391-404). It was studied if UPR induction affects the length of the HAC1/hacA mRNA in T. reesei and A. nidulans. The T. reesei strain RutC-30 (Montenecourt and Eveleigh, 1979, Adv. Chem. Ser. 181, 289-301) was grown in a shake flask in a Trichoderma minimal medium (Penttilä et al., 1987, Gene 61, 155-164) with 2% lactose as the carbon source. Growth was performed for 60 hours at 28° C. and 200 RPM, and the mycelium was diluted 1:10 into the same medium and grown for additional 21 hours. The culture was subsequently divided into two halves, and one half of it was treated with 10 mM dithiothreitol (DTT) to induce the UPR pathway (Saloheimo et al., 1999, Mol. Gen. Genet. 262, 35-45). Mycelial samples were collected from the culture treated with DTT and the untreated control culture before DTT addition and 30, 60, 90, 120 240 and 360 minutes after the addition of DTT. Total RNA was isolated from the samples with the TRIzol reagent (Gibco-BRL) according to manufacturer's protocols. RNA samples of 5 µg were treated with glyoxal and run in a 1% agarose gel in 10 mM Na-phosphate buffer, pH 7.0. Capillary blotting onto a Hybond-N nylon filter (Amersham) was done as instructed by the manufacturer. The full-length HAC1 cDNA that was used as a probe was labelled as described in Example 3. Hybridization was performed for 18 hours at 42° C. in 50% formamide, 10% dextran sulphate, 1% SDS, 1 M NaCl and 125 µg/ml of herring sperm DNA. The filter was washed in 5×SSPE for 15 minutes at 42° C., in 1×SSPE, 0.1% SDS for 30 minutes at 42° C. and in 0.1×SSPE, 0.1% SDS for 30 minutes at room temperature. The results (FIG. 11) show that the length of the HAC1 mRNA does not change in the control samples not treated with DTT. In the samples treated with DTT a shorter mRNA of about 2.2 kb appears in addition to the 2.5 kb mRNA observed in the control samples. The full-length HAC1 cDNA probe was removed from the Northern filter by incubating it in 0.1% SDS at 100° C. for 10 minutes. The filter was then hybridized with a probe containing a 160 by sequence from the 5' flanking region of the HAC1 gene. This probe was made by PCR from the plasmid pMS119 (FIG. 6) with the 13 primer (5' AAT TAA CCC TCA CTA AAG GG 3') (SEQ ID No. 26) binding to the pBluescript vector as the forward PCR primer and the oligonucleotide 5' TGG TTG ATG ACG ACG ATGCGA ACA GTC ATG ACA GGC AAC G 3' (SEQ ID No. 27) as the reverse primer. The PCR reaction was performed as described in Example 2. The probe preparation was done as in Example 3. The Northern hybridisation with the short fragment was done as described above for the full-length HAC1 cDNA probe. The short probe fragment derived from the 5' flanking region of the HAC1 cDNA hybridized with the full-length HAC1 mRNA of 2.5 kb but not with the 2.2 kb mRNA that appears when UPR is induced by DTT, indicating that the 5' end is the segment absent in the 2.2 kb mRNA. It has previously been shown that the T. reesei pdi1 gene is controlled by the UPR (Saloheimo et al., 1999, Mol. Gen. Genet. 262, 35-45). To show that the UPR is induced in this experiment with DTT, the filter was probed with the pdi1 and gpd1 probes. The pdi1 mRNA becomes more abundant in the mycelium treated with DTT, whereas the gpd1 mRNA remains at an almost constant level.

To analyse more closely the change that occurs in the T. reesei HAC1 mRNA upon UPR pathway induction, the mRNA populations in induced and uninduced conditions were studied by rapid amplification of cDNA ends by PCR (RACE-PCR). PolyA+ RNA was isolated from total RNA samples derived from a DTT-treated and an untreated control mycelia, using the OligoTex mRNA isolation kit (Qiagen) as instructed by the manufacturer. The Marathon cDNA amplification kit (Clontech) was used in the RACE-PCR procedure according to manufacturer's protocols. The HAC1-specific oligonucleotide used in the reaction was 5' GGG AGA CGA CTG CTG GAA CGC CAT 3' (SEQ ID No. 28). It binds 500 by downstream from the 5' end of the full-length HAC1 cDNA. The isolated mRNA was used in synthesis of double-stranded cDNA. An oligonucleotide adapter was ligated to the ends of the cDNA, and the 5' ends of the HAC1 cDNAs in each sample were amplified by PCR with the HAC1-specific primer and a primer supplied in the kit that binds to the ligated adapter. The PCR program consisted of 5 cycles with denaturation at 94° C. for 5 seconds and synthesis at 72° C. for 3 minutes followed by 5 cycles with denaturation at 94° C. for 5 seconds and synthesis at 70° C. for 3 minutes and 25 cycles with denaturation at 94° C. for 5 seconds and synthesis at 68° C. for 3 minutes. The PCR products were analysed in a 1% agarose gel. A fragment of the expected size (about 550 bp, including the 5' flanking region of the HAC1 gene and the adapter ligated to the end), corresponding to the 2.5 kb mRNA, was obtained from the control sample derived from mycelia not treated with DTT. A second fragment of about 250 bp, corresponding to the 2.2 kb mRNA size, was obtained in the PCR from the sample treated with DTT in addition to the one observed in the control sample. The 550 by fragment of the control sample and the 250 by fragment from the DTT-treated sample were isolated from the agarose gel with the Qiaquick gel extraction kit (Qiagen) as instructed by the manufacturer, and cloned into the pCR2.1-TOPO vector with the TOPO TA cloning kit (Invitrogen) as instructed by the manufacturer. Two independent clones derived from the control RNA and carrying the 550 by insert were sequenced. They had their 5' end 8 by and 16 by downstream from the 5' end of the full-length cDNA (nucleotides 8 and 16 in the sequence in FIG. 7) and the sequence continued until the end of the HAC1-specific primer as in FIG. 7. Seven independent clones derived from the DTT-treated mycelium and carrying 250 by inserts were sequenced. The 5' ends of these fragments were each at different positions between nucleotides 254 and 336 in the sequence in FIG. 7, and in each case the sequence continued until the end of the HAC1-specific primer as in FIG. 7. This further confirms that the 5' end of the *T. reesei* HAC1 mRNA is absent when the UPR pathway is induced by DTT. The upstream open reading frame (uORF) of 17 amino acids is in the region that is left out from the mRNA. Thus this uORF could be involved in the regulation, preventing translation initiation at the correct start codon and formation of the HACI protein.

The splicing of the 20 by intron from the *T. reesei* HAC1 mRNA upon UPR induction was studied by reverse transcriptase-PCR (RT-PCR). The mRNA samples used in RACE-PCR (previous paragraph), one treated with 10 mM DTT and the other not treated, were subjected to first strand cDNA synthesis with the Riboclone cDNA synthesis system (Promega) according to manufacturer's instructions. A fragment of about 500 by in length, covering the region with the 20 by intron in the HAC1 gene, was amplified by PCR from the synthesized cDNA using the forward primer 5' CCC CGA GCA GTC CTT GAT GG 3' (SEQ ID No. 29) and the reverse primer 5' GTC GTT GAT GTC GM GT 3' (SEQ ID No. 30). The PCR program consisted of denaturation at 94° C. for 2 minutes followed by 30 cycles with denaturation at 94° C. for 45 seconds, annealing at 50° C. for 30 seconds and synthesis at 72° C. for 1 minute. A final synthesis step of 5 minutes at 72° C. was performed. The DNA fragments obtained in the PCR were cloned into the pCR2.1 vector with the TOPO TA cloning kit (Invitrogen) as instructed by the manufacturer. Ten fragments derived from both the DTT-treated sample and the nontreated control sample were sequenced. Nine out of the ten fragments from control sample had the intron unspliced. Only two out of the ten fragments from the DTT-treated sample had the intron unspliced, showing that splicing of the intron occurs upon UPR induction by DTT.

Figure 12:
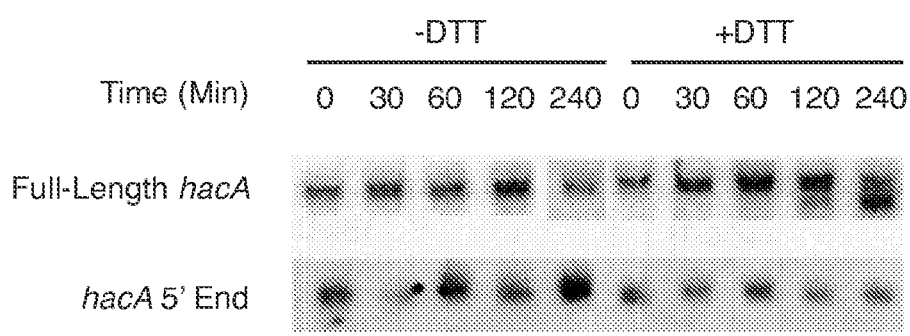
FIG. 12 depicts Northern hybridization of RNA samples derived from *A. nidulans* mycelia treated with DTT (+DTT) and untreated control mycelia (−DTT). The timepoints after DTT addition are shown. The probes are shown on the left.

To examine whether the 5' flanking region and the 20 by intron are removed from the *Aspergillus nidulans* hacA mRNA upon UPR induction similarly to the *T. reesei* HAC1 mRNA, Northern hybridisation and RT-PCR experiments were carried out. The *A. nidulans* strain FGSC A26 was grown for three days in shake flasks in a medium containing 3% glucose, 2.5% corn steep liquor, 15 g/l $KH_2PO_4$, 5 g/l $(NH_4)_2SO_4$, 5 mg/l FeSO, 1.6 mg/l $MnSO_4$, 1.4 mg/l $ZnSO_4$, 3.7 mg/l $CoCl_2$, pH 6.8. The culture was divided into two aliquots, and one aliquot was treated with 20 mM DTT and the other served as a control. Samples were withdrawn from both aliquots at 0, 30, 60, 120 and 240 minutes after the DTT addition. The mycelium was washed with 0.9% NaCl and stored frozen at −70° C. Total RNA was isolated from the mycelia with the Trizol reagent (Gibco-BRL) as instructed by the manufacturer. Agarose gel electrophoresis, Northern blotting and hybridization of the RNA samples was performed as described in the first paragraph of this example. The Northern was first probed with the full-length hacA genomic fragment shown in FIG. 8. The probe hybridizes with a single 1.7 kb mRNA band in samples not treated with DTT. In the samples treated with DTT for 120 and 240 minutes, an additional band of about 1.55 kb is detected, showing that the hacA mRNA is truncated upon UPR induction (FIG. 12). The Northern was then probed with a short probe derived from the 5' end of the hacA gene. The probe fragment was made by PCR from the pGEM-AT vector carrying the hacA gene (Example 3) with the T7 primer (5' GTA ATA CGA CTC ACT ATA GGG C 3') (SEQ ID No. 31) as the forward primer and hacA-specific oligonucleotide 5' TTA GGA CAG AGG CCA CGG TGT 3' (SEQ ID No. 32) as the reverse primer. The PCR reaction was performed as described in the previous paragraph. The 5' end probe has the first 90 by of the sequence in FIG. 8. The short 5' end probe hybridizes only with the 1.7 kb mRNA, showing that the hacA mRNA is truncated from the 5' end when the UPR pathway is induced.

To test if the 20 by intron is removed from the *A. nidulans* hacA gene when UPR is induced by DTT, RT-PCR was performed. The total RNA samples isolated from mycelia treated with 20 mM DTT for 240 minutes and from control mycelia were subjected to RT-PCR reactions with the Robust RT-PCR kit (Finnzymes, Finland) as instructed by the manufacturer, using the forward primer 5' CCC ATC CTT GGT GAC TGA GCC 3' (SEQ ID No. 33) and the reverse primer 5' AAG AGT CGG TGT CAG AGT TGG 3' (SEQ ID No. 34). The DNA fragment of about 400 by obtained in the PCR was cloned into the pCR2.1-TOPO vector with the TOPO TA cloning kit (Invitrogen) as instructed by the manufacturer. Twelve of the cloned fragments derived from DTT-treated and ten from control mycelia were sequenced. None of the fragments derived from the control mycelia had the intron spliced. Three of the fragments derived from the DTT-treated mycelia had the intron spliced.

Example 5

Complementation of Yeast HAC1 and IRE1 Disruptions by Different Forms of the *T. reesei* HAC1 cDNA The *S. cerevisiae* IRE1 gene was disrupted in the same way as the HAC1 gene (described in Example 2). A fragment where a G418 resistance cassette is flanked by sequences from the 5' and 3' ends of the IRE1 open reading frame was made by PCR. The forward primer 5' ATT AAT ATT TTA GCA CTT TGA AAA ATG CGT CTA CTT CGA AGA AAC ATG CTT GCC TCG TCC CCG CCG GGT CAC 3' (SEQ ID No. 35) and the reverse primer 5' AAG CAG AGG GGC ATG AAC ATG TTA TGA ATA CAA MA TTC ACG TAA MT GTC GAC ACT GGA TGG CGG CGT TAG TAT 3' (SEQ ID No. 36) were used in the PCR reaction. The PCR reaction, yeast transformation, and selection and analysis of the disruptants were performed as described in Example 2 for HAC1 disruption.

Figure 13:
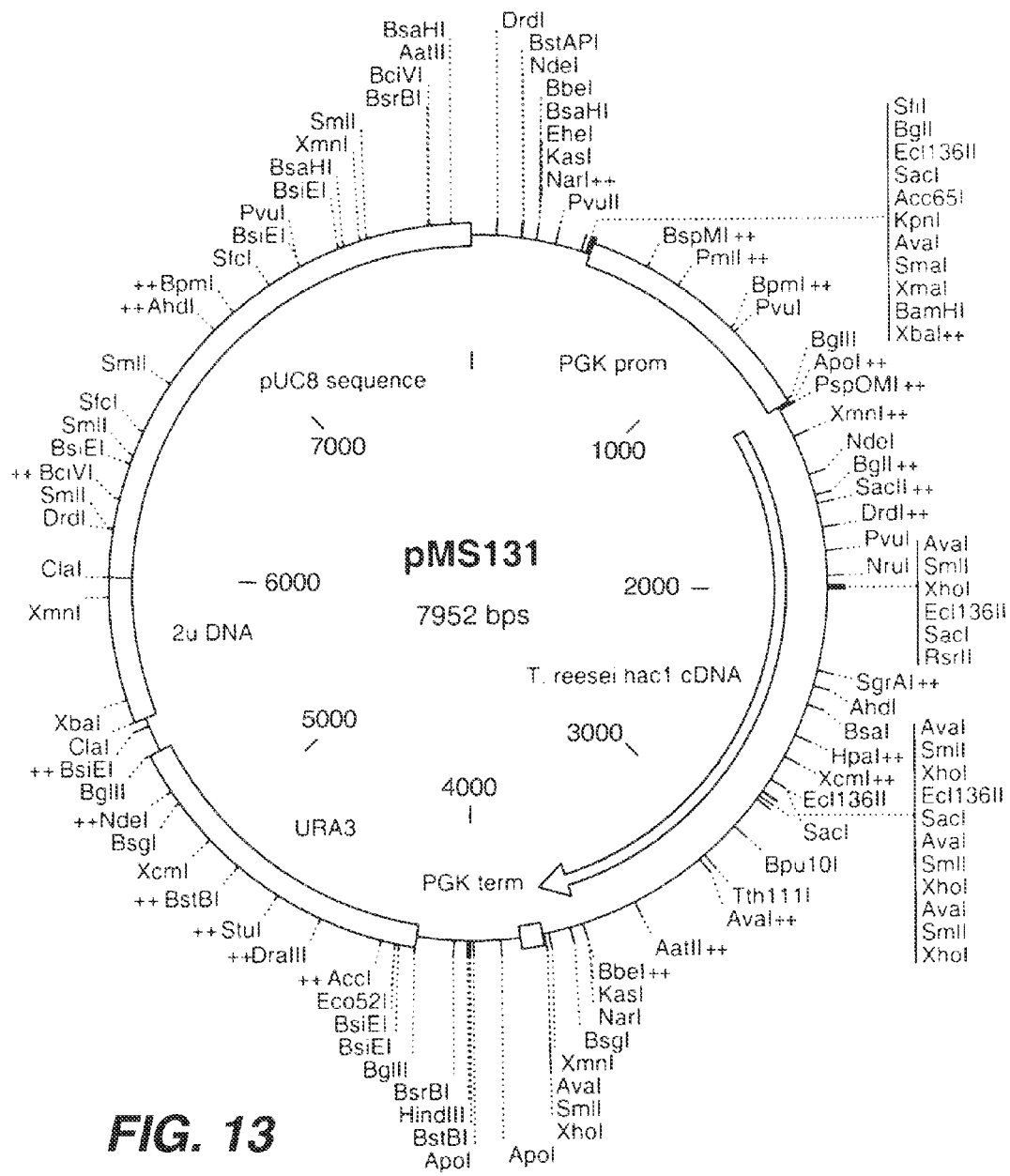
FIG. 13 depicts a map of the plasmid pMS131, where the full-length *T. reesei* HAC1 cDNA without the 20 by intron is under the yeast PGK1 promoter in the vector pAJ401.
Figure 14:
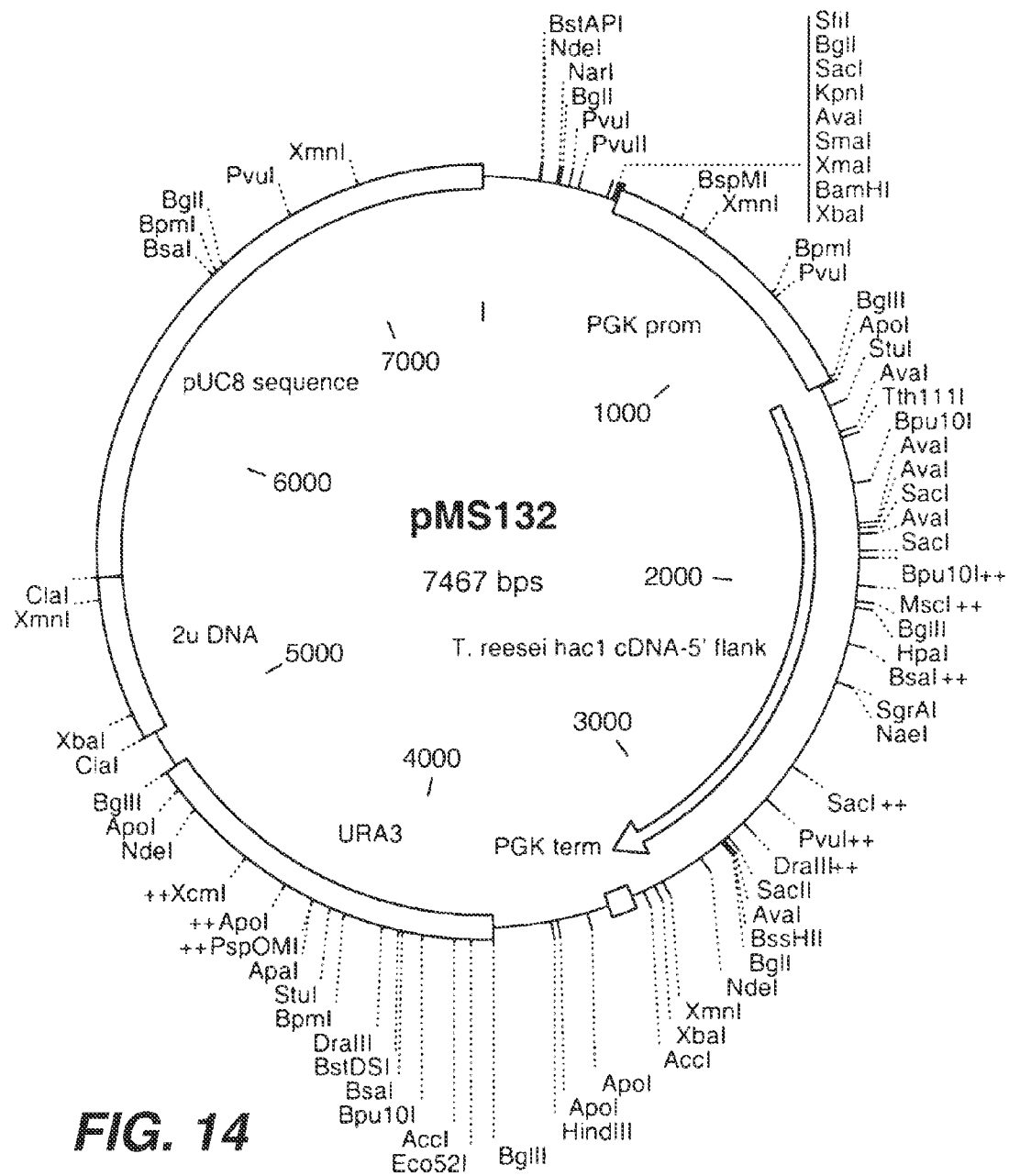
FIG. 14 depicts a map of the plasmid pMS132, where the *T. reesei* HAC1 cDNA without the 5' flanking region and without the 20 by intron is under the yeast PGK1 promoter in the vector pAJ401.

To express different forms of the *T. reesei* HAC1 gene in the yeast HAC1 and IRE1 disruptants, four expression constructs were made into the multicopy expression vector pAJ401 (Saloheimo et al., 1994, *Mol. Microbiol.* 13, 11-21) with the URA3 marker gene and yeast PGK1 promoter and terminator to drive the expression. One of them has the HAC1 cDNA with the intact 5' flanking region and does not have the 20 by intron. This plasmid, pMS131 (FIG. 13), was made by releasing the HAC1 cDNA from pMS119, which is the pBluescript vector (Stratagene) carrying the full-length cDNA, with EcoRI and Asp718 digestion, filling in the ends of the fragment with Klenow polymerase and ligating it to the EcoRI restriction site of pAJ401 with methods known in the art. The second construct has the *T. reesei* HAC1 cDNA truncated at the 5' end but does not have the 20 by intron. The truncated HAC1 cDNA fragment was made by PCR from the plasmid pMS119 (FIG. 6) with the forward primer 5' CCG CAA CAC GAC ACG GCA GGC AAC 3' (SEQ ID No. 37) and reverse primer 5' CTA GGT AGA CGT TGT ATT TTG 3' (SEQ ID No. 38). The PCR reaction was carried out as described in Example 2. The PCR product was run in a 0.8% agarose gel and purified from it with the Qiaquick gel extraction kit (Qiagen). The fragment was cloned into the EcoRV restriction site of the pZERO vector using the Zero Background Cloning kit (Invitrogen) according to manufacturer's protocols. The fragment was released from this vector with BamHI digestion and cloned between the EcoRI and XhoI restriction sites of the pAJ401 vector with methods known in the art. The resulting plasmid was named pMS132 (FIG. 14). The third and fourth expression plasmids have the 20 by intron added to the HAC1 cDNA forms either with or without the 5' flanking region. These plasmids were constructed by replacing a HpaI-KspI fragment of about 800 by in pMS131 and pMS132 with a corresponding HpaI-KspI fragment from a cDNA which has the 20 by intron, isolated from the cDNA library in λZAP together with the cDNA in the plasmid pMS119 (Example 3).

To test for complementation, the four expression plasmids and the vector pAJ401 alone were transformed into the yeast HAC1 and IRE1 disruptants as described (Gietz et al., 1992, *Nucl. Acids Res.* 20, 1425). Four transformants from each of the transformations were streaked on SC-Ura plates (Sherman, 1991, *Meth. Enzymol.* 194, 3-21) and grown at 30° C. for three days. The plates were then replicated onto mineral medium plates (Verduyn et al., 1992, *Yeast* 8, 501-517) with inositol and on plates without inositol. These plates were incubated at 30° C. for three days and the streaks growing on them were replicated again onto the same plates. After growth of five days the inositol dependence of the transformants was evaluated (FIG. 15). Both pMS131 (HAC1 cDNA with 5' flanking region and without intron) and pMS132 (without 5' flanking region, without intron) could restore the ability of both the HAC1 and IRE1 disruptants to grow without inositol. Thus the *T. reesei* HAC1 encodes the functional homolog of the yeast HAC1 gene. When the 20 by intron is added to pMS131, no complementation is obtained. When the intron is added to pMS132, the yeast disruptants grow very slowly without inositol. Thus the 20 by intron weakens the ability of the *T. reesei* HAC1 gene to complement the yeast HAC1 and IRE1 disruptions.

Example 6

Binding of the *T. Reesei* HACI Protein to UPR Elements of the pdi1 and bip1 Promoters A fragment of the *T. reesei* HACI protein containing the putative DNA binding domain and leucine zipper region was produced in *E. coli* as a fusion protein with the *E. coli* maltose-binding protein malE. A DNA fragment encoding this part of the HACI protein was prepared by PCR from the HAC1 cDNA with the oligonucleotide primers 5' TCG AAC GGA TCC GAA AAG AAG CCC GTC AAG AAG AGG 3' (forward primer) (SEQ ID No. 39) and 5' ATC GCA GGA TCC CTA GGT TTG GCC ATC CCG CGA GCC AAA 3' (reverse primer) (SEQ ID No. 40). The PCR reaction was performed as in Example 2. The PCR product of 360 by was run in an 0.8% agarose gel and purified from the gel with the Qiaquick gel extraction kit (Qiagen). The fragment was digested with BamHI at the restriction sites included in the PCR primers and cloned into the BamHI restriction site of the vector pMAL-p2X (New England Biolabs) with methods known in the art. The HACI-malE protein was produced in *E. coli* and purified by amylose affinity chromatography using the pMAL Protein Fusion and Purification System (New England Biolabs) as recommended by the manufacturer. The *E. coli* cells were grown up to OD600 0.5 at 37° C., IPTG was added to the concentration of 0.3 mM, and production was carried out for 3 hour at 24° C. The HACI-malE fusion protein with the expected apparent molecular weight was purified.

The oligonucleotides used in binding reactions were annealed in the concentration of 100 mg/ml in 50 mM Tris, pH 8.0, 10 mM MgCl$_2$, 1 mM spermidine and 5 mM DTT by heating them at 65° C. for 10 minutes and letting them cool down to room temperature during 2 hours. The oligonucleotides were labelled by incubating 100 ng of the annealed oligonucleotide in 10 mM Tris, pH 8.0, 5 mM MgCl$_2$ with 20 μCi of $^{32}$P-dCTP and 2.5 U Klenow polymerase (Boehringer Mannheim) at 37° C. for 30 minutes. The binding reactions between the oligonucleotides having the putative UPR elements and the proteins were carried out with 0.5-2 μg of the HACI-malE fusion protein or 2 μg of the malE protein and 1 ng of the annealed and labelled oligonucleotide in a mixture containing 20 mM HEPES, pH 6.9, 50 mM KCl, 10 mM MgCl$_2$, 0.25 mM EDTA, 0.5 mM DTT, 2% Ficoll, 5% glycerol and 100 μg/ml poly(dIdC) DNA. The competing oligonucleotides were used in 20-200 times excess of the labelled oligonucleotide. The binding reaction mixtures were incubated for 30 minutes at 25° C. and run in a 5% polyacrylamide gel with 10% glycerol in 12.5 mM Tris-borate, pH 8.3, 0.6 mM EDTA for three hours. The gel was dried on a filter paper and exposed onto an X-ray film.

The following oligonucleotides carrying the putative UPR elements of the pdi1 and bip1 promoters were used in the binding reactions (only the leading strand is given, the UPREs are given in bold): pdiUPREI+II, containing both of the putative UPR elements of the pdi1 promoter (Saloheimo et al. 1999, *Mol. Gen. Genet.* 262, 35-45).

```
                                            (SEQ ID No. 41)
5' CGG CTG AAC CAG CGC GGC AGC CAG ATG TGG CCA AAG

GG 3'
``` pdiUPREI, containing the UPREI of the pdi1 promoter in a random context

```
                                            (SEQ ID No. 42)
5' GGT ACC TGC TAA CCA GCG CGG CAT GAT TCA AC 3'
``` pdiUPREII, containing the UPREII of the pdi1 promoter in a random context

```
                                            (SEQ ID No. 43)
5' GGA TCT TGC ATA GCC AGA TGT GGC CTC GAT TGA

CT 3'
``` bipUPREI, containing the UPREI of the bip1 promoter (unpublished results)

```
                                            (SEQ ID No. 44)
5' GGA TTA GAA AAC GCC AAC GTG TCC ATA ACG GTC 3'
``` bipUPREII, containing the UPREII of the bip1 promoter, the element is in a reverse orientation in the promoter (unpublished results)

```
                                            (SEQ ID No. 45)
5' GGG CGT GGA GAA GCG AGA AGT GGC CTC TTC TTC

TCC 3'
```

Figure 16:
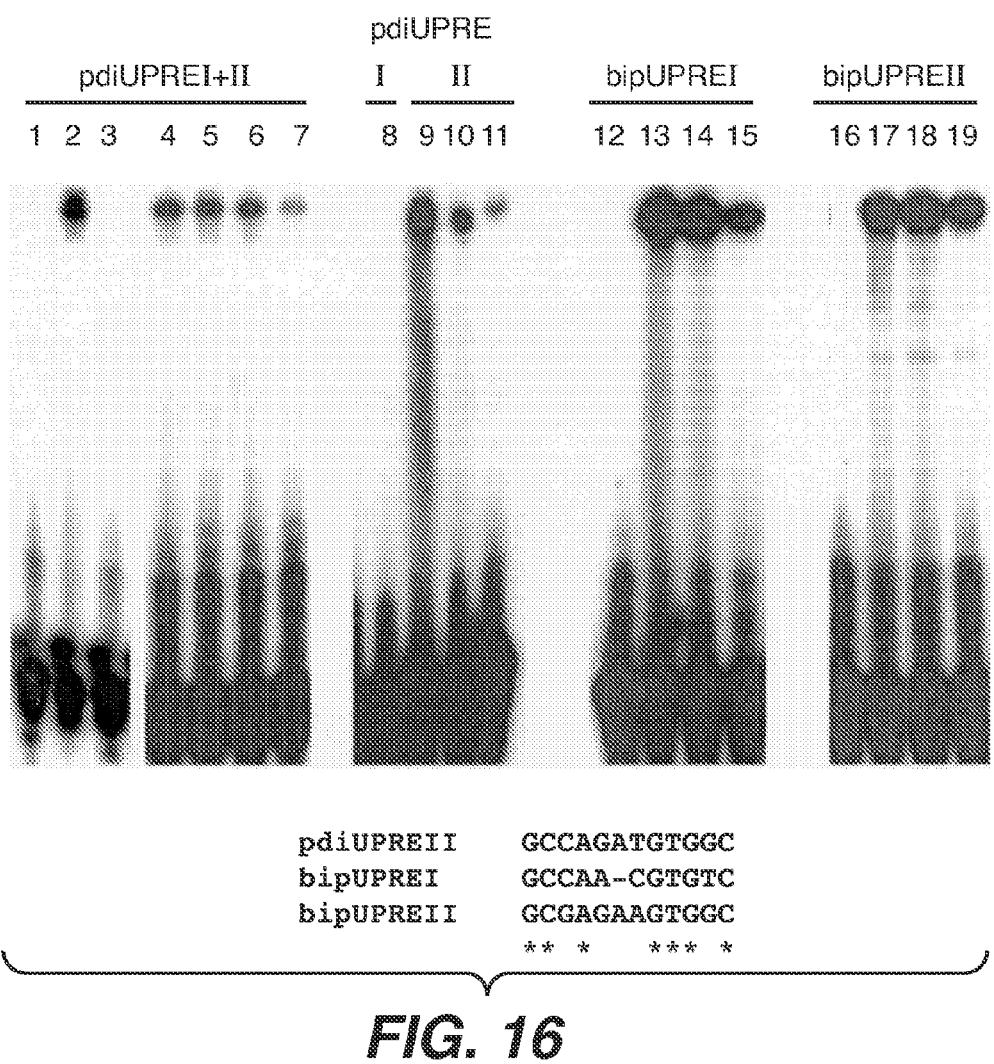
FIG. 16 depicts bandshift experiments, where the binding of the malE-HACI fusion protein to the putative UPR element sequences found in *T. reesei* pdil and bipl promoters was tested. The oligonucleotides used in the binding reactions are shown on the top. Lanes 1, 12 and 16, no protein; lanes 2, 4-7, 8-11, 13-15 and 17-19, malE-HACI fusion protein; lane 3, malE protein alone. The binding was competed with unlabelled oligonucleotides on lanes 5 (20× excess); lanes 6, 10, 14 and 18 (50× excess) and lanes 7, 11, 15, and 19 (200× excess). Alignment of the UPR element sequences that bind the HACI-malE protein is shown below wherein the sequence of pdiUPREII is set forth in SEQ ID No: 61, the sequence of bipUPREI is set forth in SEQ ID No: 62, and the sequence of bipUPREII is set forth in SEQ ID No. 63.

The results (FIG. 16) show that the HACI-malE fusion protein binds to the putative UPR element area found from the pdi1 promoter whereas the malE protein alone does not show any binding. The binding of the fusion protein is specific, since it is competed by an excess of unlabelled oligonucleotide. The fusion protein binds specifically also to the oligonucleotide pdiUPREII and not at all to pdiUPREI, and this indicates that the functional UPR element of the pdi1 promoter is UPREII. The HACI-malE fusion protein also binds specifically to both of the putative UPR elements found in the bip1 promoter. Alignment of the three T. reesei UPR element shows that the consensus sequence for binding is GC(C/G)A (G/A)N$_{1-2}$GTG(G/T)C (FIG. 16) (SEQ ID No. 46).

Example 7

Figure 17:
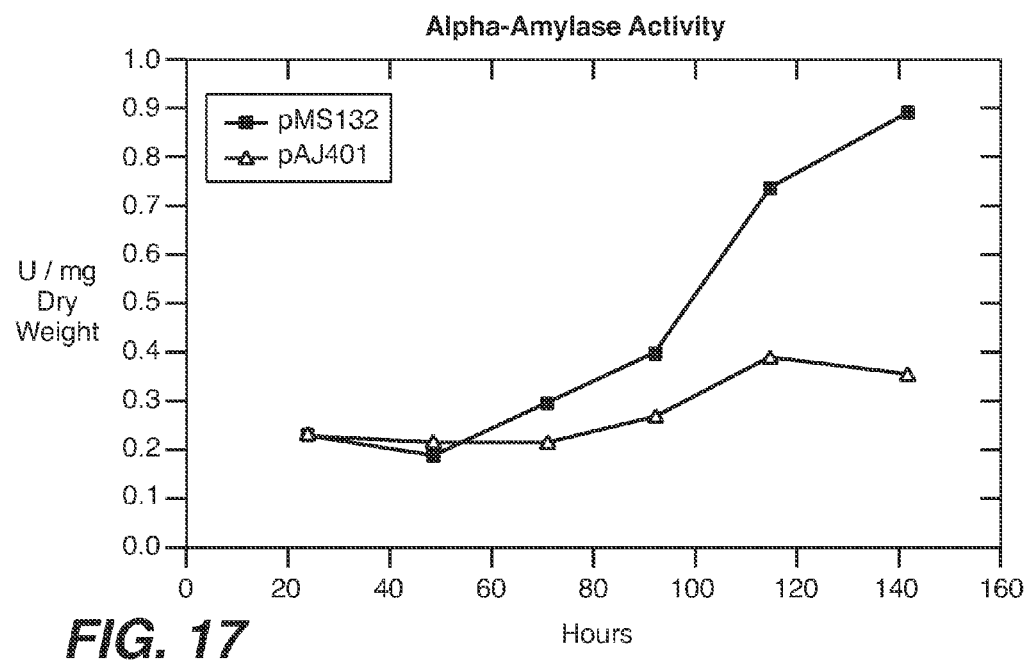
FIG. 17 depicts a graph which shows activity of α-amylase by yeast strains expressing the *T. reesei* HAC1 cDNA without the 5' flanking region and the 20 by intron (pMS132) (squares) and control strains with the expression vector alone (pAJ401) (diamonds) in the vertical bar over time, horizontal bar, and which further shows that activity is greater wherein pMS132 is present.
Figure 18:
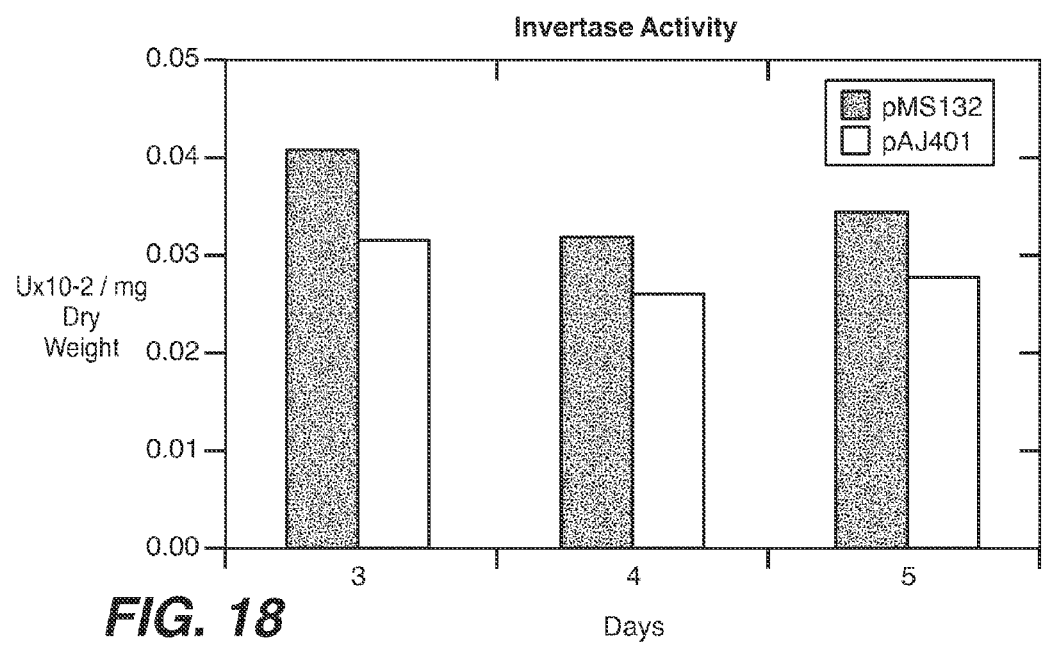
FIG. 18 depicts a bar graph which shows activity of invertase by yeast strains expressing the *T. reesei* HAC1 cDNA without the 5' flanking region and the 20 by intron (pMS132) and control strains with the expression vector alone (pAJ401) in the vertical bar, over time (horizontal bar) and which further shows that activity is greater is greater wherein pMS132 is present.

Expression in Yeast of the Trichoderma HAC1 cDNA without its 20 Bp Intron and Truncated at the 5' End The T. reesei HAC1 cDNA was expressed without its 5' flanking region and without the 20 by intron from the plasmid pMS132 (FIG. 14). This plasmid and the control plasmid pAJ401 were transformed with a described method (Gietz et al., 1992, Nucleic Acids Res. 20, 1425) into the yeast strain producing Bacillus amyloliquefaciens α-amylase described in Example 1. Two strains carrying pMS132 and two strains with pAJ401 were grown for six days in shake flasks (250 RPM, 30° C.) in SC-Ura medium (Sherman, 1991, Meth. Enzymol. 194, 3-21) buffered to pH 6.0 with 2% succinic acid and growth and amylase production were assayed as described in Example 1. Cell samples were withdrawn from the culture for Northern analysis. The α-amylase production of the pMS132 transformants calculated per biomass was higher than that of the pAJ401 transformants from day 3 until the end of the cultivation (FIG. 17). Growth of the pMS132 strains was slower than the growth of the control plasmid strains. Four pMS132 transformants and four pAJ401 transformants were grown in shake flasks (250 RPM, 30° C.) in SC-Ura with 2% sucrose as the carbon source, and invertase activity produced by the cells was assayed as described in Example 1. More invertase was produced by the pMS132 transformants than by the pAJ401 transformants (FIG. 18).

Figure 19A:
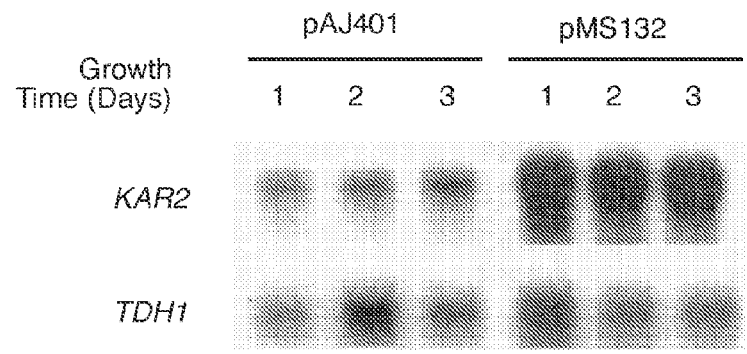
FIG. 19 depicts Northern hybridization of RNA samples from a yeast strain expressing the *T. reesei* HAC1 cDNA without the 5' flanking region and the by intron (pMS132) and a control strain with the expression vector alone (pAJ401). The probes used for hybridization are shown. The signals were quantified with a phosphoimager and the KAR2 signal intensities were normalised with respect to the TDH1 signal intensities. The normalised KAR2 signals are shown on the bottom wherein it is shown that pMS132 has greater signal.
Figure 19B:
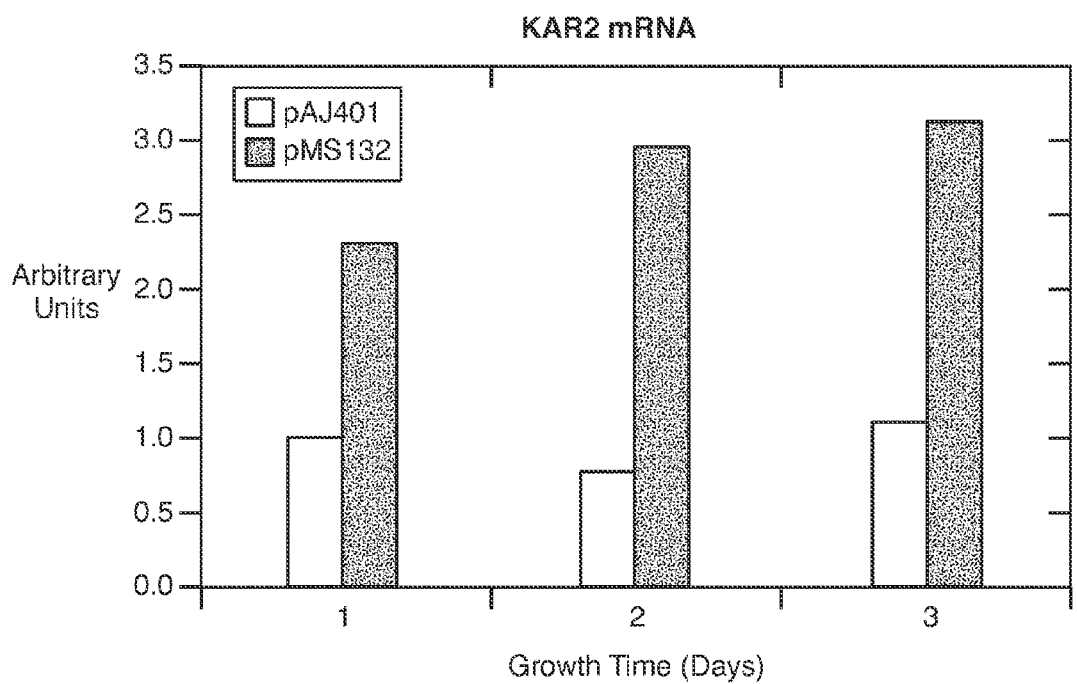

To show that the truncated T. reesei HAC1 cDNA is beneficial for α-amylase and invertase production by inducing the UPR pathway of yeast, Northern analysis was performed on the cell samples withdrawn from the cultures of pMS132 and pAJ401 transformants. Total RNA was isolated from the cells collected after 1, 2 and 3 days of growth with the RNeasy RNA extraction kit (Qiagen) as instructed by the manufacturer. The yeast KAR2 gene is under the UPR pathway control (Cox and Walter, 1996, Cell 87, 391-404), and therefore the Northern filter was probed with a fragment derived from KAR2. This fragment was produced by PCR from yeast chromosomal DNA with the oligonucleotide primers 5' GTG GTA ATA TTA CCT TTA CAG 3' (SEQ ID No. 47) (forward primer) and 5' CAA ITT CAA TAC GGG TGG AC 3' (reverse primer) (SEQ ID No. 48). A fragment from the yeast TDH1 gene encoding glyceraldehyde phosphate dehydrogenase was used as a control probe, since this gene is expressed constitutively and is not expected to be affected by UPR. The TDH1 probe fragment was made from yeast chromosomal DNA by PCR with the oligonucleotide primers 5' TGT CAT CAC TGC TCC ATC TT 3' (forward primer) (SEQ ID No. 49) and 5' TTA AGC CTT GGC AAC ATA TT 3' (reverse primer) (SEQ ID No. 50). The PCR reaction was done as in Example 2 and the probes were prepared as described in Example 3. Northern blotting and hybridization were performed from the RNA samples as described in Example 4. The filter was exposed to the screen of the phosphoimager SI (Molecular Dynamics), and the signal intensities were quantified with the phosphoimager. The KAR2 signal intensities were normalized with reference to the TDH1 signal intensities. The results (FIG. 19) show that the KAR2 mRNA abundance is 2-4-fold higher in the pMS132 transformants than in the pAJ401 transformants in all the timepoints.

Example 8

Figure 20:
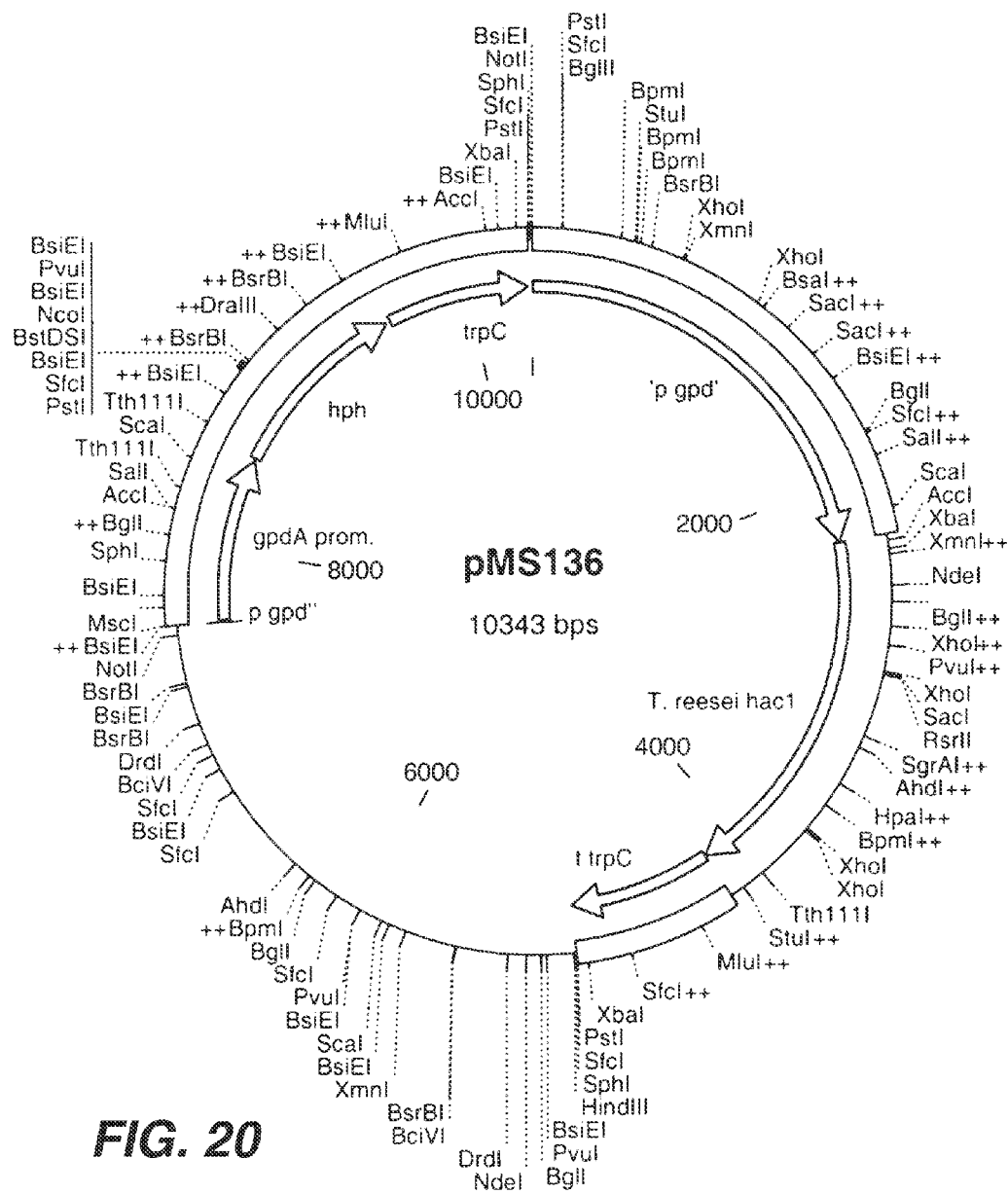
FIG. 20 depicts a map of the plasmid pMS136, where the *T. reesei* HAC1 cDNA without the 5' flanking region and the 20 bp intron is under the *A. nidulans* gpdA promoter in the vector pAN52-NotI.
Figure 21A:
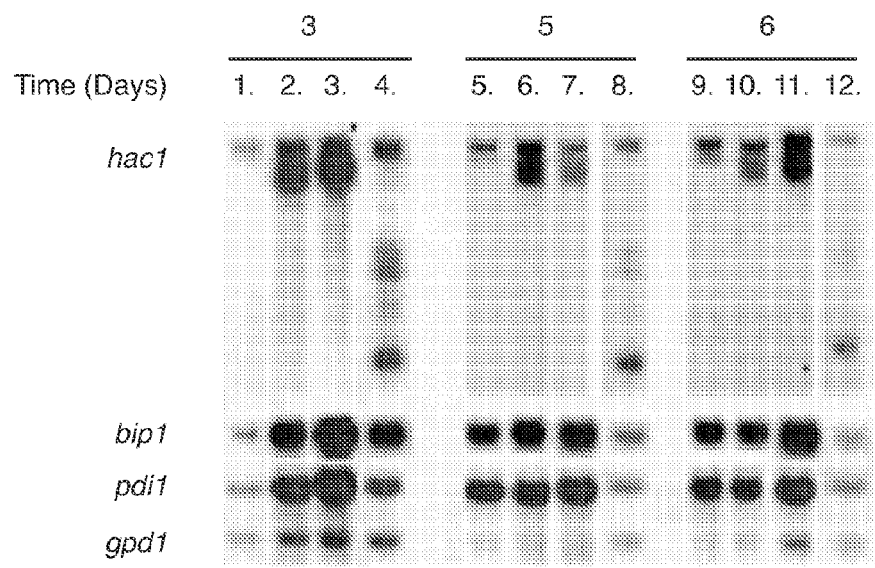
FIG. 21 depicts Northern hybridization of RNA samples derived from transformation of the plasmid pMS136 into a *T. reesei* strain producing CBHI-chymosin fusion protein. Samples from the parental strain (lanes 1, 5 and 9), two positive transformants (lanes 2, 3, 6, 7, 10 and 11) and a HAC1 mutant strain designated number 31 generated in the transformation (lanes 4, 8 and 12) are shown. The growth times are shown on the top and the probes used for the hybridization on the left. Quantifications of the pdi1 and bip1 signals normalised with respect to gpd1 signals are shown on the bottom.
Figure 21B:
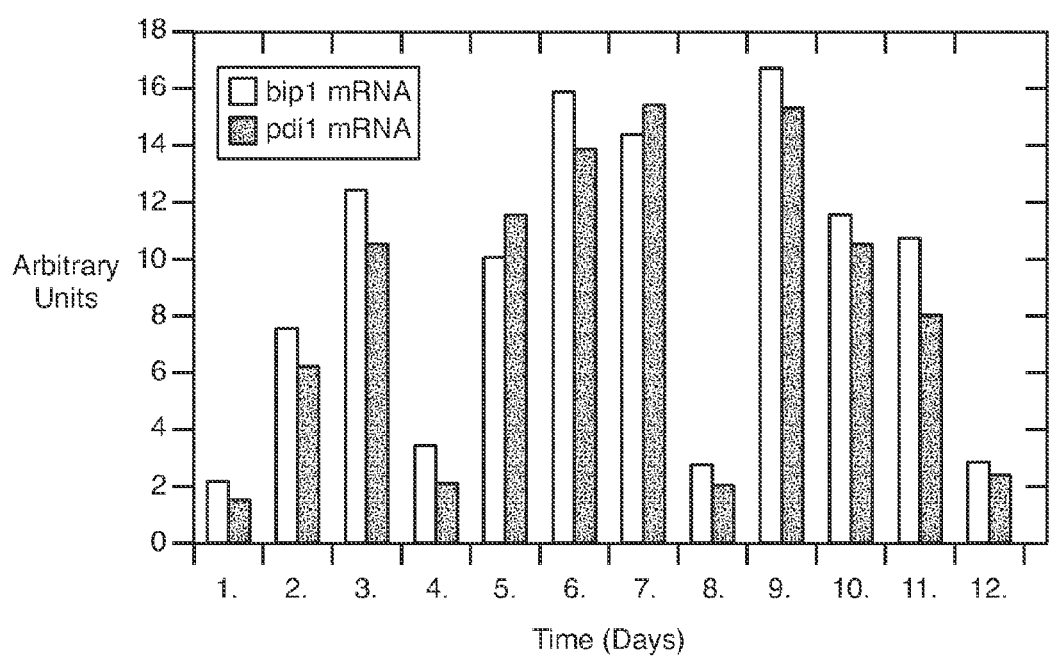

Expression in Trichoderma reesei of the HAC1 Gene without its 20 by Intron and Truncated at the 5' End To induce the UPR pathway constitutively, a form of the T. reesei HAC1 cDNA that is truncated at its 5' flanking region and does not have the 20 by intron was expressed in T. reesei. The form of the HAC1 cDNA that was present in pMS132 was expressed in yeast as described in Example 5 was cloned with methods known in the art into the NcoI restriction site of the vector pAN52-NotI, between the gpdA promoter and trpC terminator of Aspergillus nidulans. The hygromycin resistance cassette consisting of the A. nidulans gpdA promoter and trpC terminator and the E. coli hygromycin resistance gene was subsequently cloned into the NotI restriction site of the pAN52-NotI carrying the HAC1 cDNA fragment. The resulting plasmid, named pMS136 (FIG. 20), was transformed into T. reesei strain P37PΔCBHIpTEX-CHY22 as described (Penttilä et al., 1987, Gene 61, 155-164). Strain P37PΔCBHIpTEX-CHY22 was constructed by transformation of strain P37PΔCBHIPyr-26 (U.S. Pat. No. 5,874,276) with a version of the expression vector of pTEX-CHY. Vector pTEX-CHY is a derivative of pTEX in which the coding region for the T. reesei cellobiohydrolase I (CBHI) signal sequence, catalytic core and linker region (amino acids 1-476 of CBHI, Shoemaker, et al., 1983, Bio/Technology, 1:691-696) fused to the coding region of bovine prochymosin B (Harris et al., Nucleic Acids Research, 10:2177-2187. was inserted between the cbh1 promoter and terminator region by methods known in the art. Selection of the P37PΔCBHIpTEX-CHY22 transformants with pMS136 was performed on media with 100 µg/ml hygromycin. To obtain uninuclear transformant clones, the transformants were sporulated and single spores were plated on the selective medium with hygromycin. Purified transformants and the parental strain used in the transformation were grown in shake flasks (28° C., 200 RPM) in Trichoderma minimal medium (Penttilä at al., 1987, Gene 61, 155-164) supplemented with 3% whey and 0.2% peptone. Mycelial samples were collected from the cultures on the third, fifth and sixth cultivation days. Total RNA was isolated from the mycelia with the TRIzol reagent (Gibco-BRL) as instructed by the manufacturer. Northern blotting and hybridization were performed to the RNA samples as described in Example 4. The Northern filter was first probed with the full-length HAC1 cDNA, and an mRNA derived from the expression construct which is about 2.0 kb in length can be observed in two of the transformants in addition to the 2.5 kb band that is derived from the native HAC1 gene (FIG. 21). The HAC1 probe was removed from the Northern filter by incubating it in 0.1% SDS at 100° C. for 10 minutes. The filter was subsequently probed with the T. reesei pdi1, bip1 and gpd1 probes. Pdi1 encodes the protein disulphide isomerase and has been shown to be regulated by the UPR pathway (Saloheimo et al., 1999, Mol. Gen. Genet. 262, 35-45). Bip1 (unpublished) encodes the T. reesei homologue of the ER-specific chaperone protein Bip. The gpd1 gene encodes glyceraldehyde phosphate dehydrogenase and was used as the constitutive control probe.

After hybridization the filter was exposed to the screen of the Phosphoimager SI (Molecular Dynamics) and the signals were quanified with the phosphoimager. The pdi1 and bip1 signals were normalized with respect to the gpd1 signals. The results show that in the two transformants which express the truncated HAC1 mRNA the pdi1 mRNA level is 4- and 7-fold higher than in the parental strain on the third culture day (FIG. 21). This indicates that the UPR pathway can be induced constitutively in *Trichoderma reesei* by the expression of HAC1 gene without its 20 by intron and 5' flanking region Example 9

The Effect of a *T. Reesei* HAC1 Mutation on Heterologous Protein Production

Figure 22A:
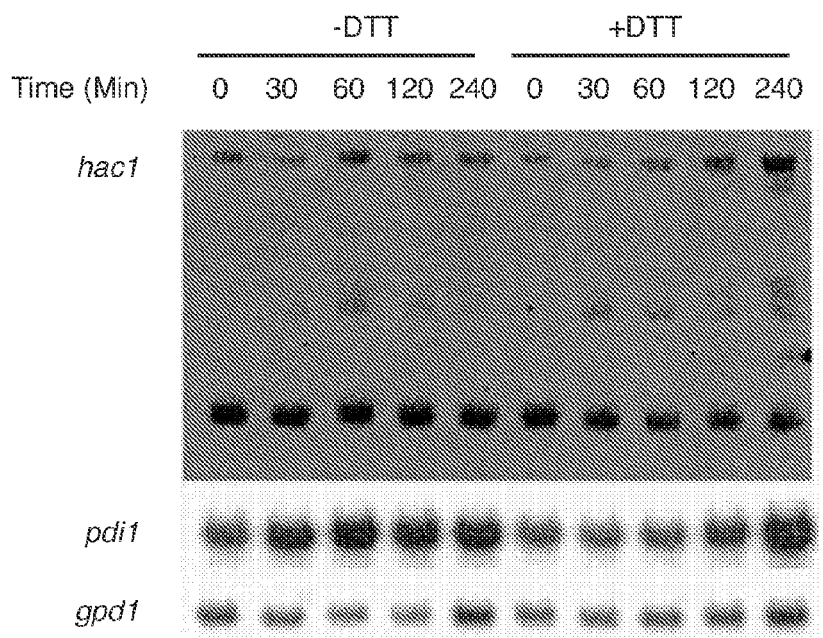
FIG. 22 depicts Northern hybridization of RNA samples derived from mycelia of the HAC1 mutant strain number 31 treated with DTT (+DTT) and untreated control mycelia (−DTT). The timepoints after DTT addition are shown on the top and the probes used for hybridization on the left. Quantifications of the pdi1 signals normalised with respect to gpd1 signals are shown on the bottom.
Figure 22B:
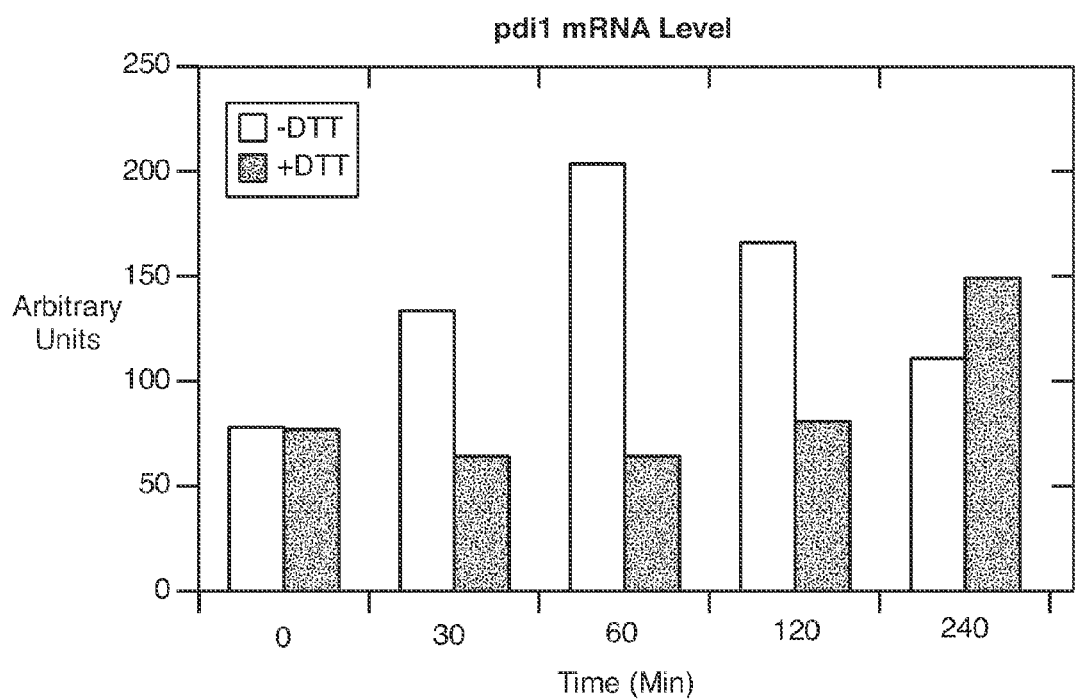

A *Trichoderma reesei* strain where the HAC1 gene is mutated was unexpectedly generated during the transformation of the plasmid pMS136 into the strain producing CBHI-chymosin fusion protein (Example 7). When analysing the transformants by Northern hybridization it was noticed that one of the transformants (number 31) produced several forms of the HAC1 mRNA that are considerably shorter than 2 kb (FIG. 21 lanes 4, 8 and 12). On the fifth and sixth day of the culture as described in Example 7 the unfolded protein response is induced in the parental strain of the transformation, presumably by the production of the heterologous protein chymosin. This is seen in the Northern analysis as appearance of a HAC1 mRNA of about 2.2 kb (truncated at the 5' flanking region) and as the induction of the pdi1 mRNA on days 5 and 6 (FIG. 21). It has previously been shown that the production of antibody Fab fragments induces the pdi1 gene (Saloheimo et al., 1999, *Mol. Gen. Genet.* 262, 35-45). In the transformant number 31 the 2.2 kb HAC1 mRNA and the induction of the pdi1 and bip1 mRNAs are not detected, suggesting that the HAC1 gene of this strain is functionally impaired. To further verify this, a DTT treatment experiment of the transformant number 31 was carried out. It was grown in shake flasks (28° C., 200 RPM) in the *Trichoderma* minimal medium (Penttilä at al., 1987, *Gene* 61, 155-164) with 3% whey and 0.2% peptone for three days. The culture was divided into two aliquots and one of them was treated with 10 mM dithiothreitol (DTT) and the other served as the control. Samples were taken from both aliquots at 0, 30, 60, 120 and 240 minutes after DTT addition. Total RNA was isolated from the mycelia and Northern hybridization was performed as described in Example 7. Hybridization of the Northern with the HAC1 probe reveals that the UPR induction by DTT is severely delayed in the transformant number 31. The HAC1 mRNA of 2.2 kb is detected only 4 hours after DTT addition (FIG. 22) and a 2-fold induction of the pdi1 gene is also apparent in this timepoint. In a wild type strain the 2.2 kb HAC1 mRNA appears and the pdi1 induction takes place after 30 minutes of DTT treatment (Example 4, FIG. 11).

Figure 23:
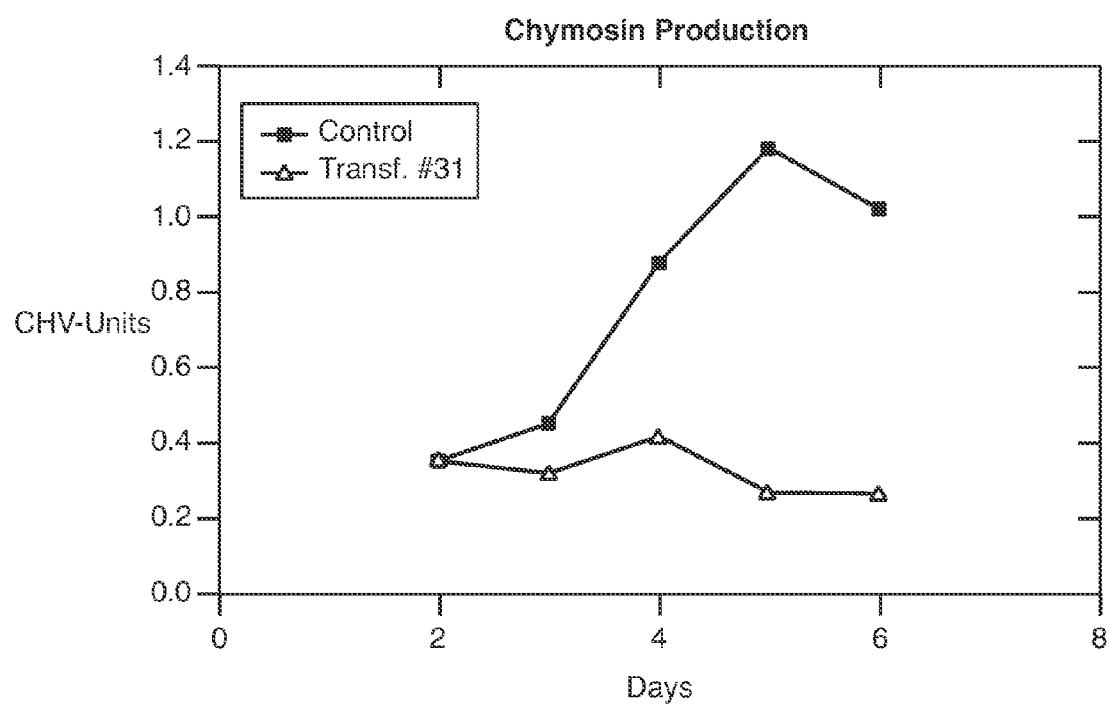
FIG. 23 is a graph depicting production of calf chymosin by the HAC1 mutant transformant number 31 (diamonds) and its parental strain (squares) during a shake flask culture. The chymosin (CHV) units per ml of culture are shown (vertical bar) over time (horizontal bar), and it is shown that the control has more units than the mutant.

The chymosin levels produced by the control strain and the transformant number 31 were measured daily from the media of the whey-peptone cultures described in example 7. The measurements were done from two parallel cultures with a milk clotting assay (Cunn-Coleman, et al., 1991, Bio/Technology, 9:976-981. Transformant number 31 produced roughly the same amount of chymosin as the parental strain on days 2 and 3 of the culture. On the later days the chymosin levels in the culture of the mutant strain started declining, whereas the control strain could still increase significantly the chymosin amount in its culture medium (FIG. 23). The difference between the two strains is evident in the late stages of the culture, where the UPR pathway is induced in the parental strain but not in the strain number 31. This suggests that a functional HAC1 gene and induction of the UPR pathway in the late culture stages is needed for efficient production of CBHI-chymosin fusion protein in *T. reesei*.

Example 10

Cloning and Sequences of the *Aspergillus nidulans* ptcB and *Trichoderma reesei* ptc2 Genes The yeast protein phosphatase encoded by the PTC2 gene has been shown to be involved in the regulation of the UPR pathway (Welihinda et al., 1998, *Mol. Cell. Biol.* 18, 1967-1977). The IRE1 protein is phosphorylated when the UPR pathway is turned on (Shamu and Walter, 1996, *EMBO J.* 15:3928-3039), and Ptc2 dephosphorylates IRE1p and regulates the UPR negatively. A BLAST search (Altschul et al., 1990, *J. Mol. Biol.* 215, 403-410) was made with the yeast Ptc2 sequence against the public database containing *Aspergillus nidulans* EST cDNA sequences, and the cDNA clone i2c04a1 was found to be homologous to it within the database. The region corresponding to this cDNA was amplified by PCR from *Aspergillus nidulans* genomic DNA with the oligonucleotides 5' TTG AAC AGC AGA TCG TTA CTG 3' (forward primer) (SEQ ID No. 51) and 5' TAT AAA GTT CGT CAA TAG TGG 3' (reverse primer) (SEQ ID No. 52). The PCR reaction was carried out as described in Example 2. The resulting PCR fragment was cloned into the pCR2.1 vector with the TOPO TA cloning kit (Invitrogen) as instructed by the manufacturer. It was sequenced with internal oligonucleotide primers (FIG. 24). The optimal hybridization conditions for isolation of the *T. reesei* ptc2 cDNA were determined by Southern hybridization of *T. reesei* genomic DNA with the *A. nidulans* ptcB fragment as described in Example 3. A *T. reesei* cDNA library constructed in λZAP (Stratagene, Stalbrandt et al., 1995, *Appl. Environ. Microbiol.* 61, 1090-1097) was screened by hybridization with the *A. nidulans* ptcB fragment as described in Example 3. The λ-clones hybridizing with the probe were excised into pBluescript plasmids with the cDNA inserts as instructed (Stratagene), and the clone having the longest insert based on restriction enzyme digestion was chosen for sequencing. The insert of this cDNA clone is 1830 by in length, encoding an open reading frame of 438 amino acids (FIG. 25). The putative *Trichoderma* PTCII protein (used interchangeably with PTC2) shows the highest identity among yeast proteins to Ptc2, 48%. It also shares 60% identity with the putative PTC2 protein from *Schizosaccharomyces pombe*. The ptcB fragment cloned from *Aspergillus nidulans* is 1264 in length (FIG. 24). Based on homology with other Ptc2 sequences, an intron has been identified in the fragment. The deduced amino acid sequence is 89% identical to *T. reesei* PTCII protein over an area of 117 amino acids.

Example 11

Cloning and Sequences of the *Aspergillus nidulans* ireA and *Trichoderma reesei* IRE1 Genes A search with the program BLAST (Altschul et al., 1990, *J. Mol. Biol.* 215, 403-410) was made with the yeast IRE1 protein sequences against the public database containing *Aspergillus nidulans* EST cDNA sequences. The EST clone v1h01a1 was homologous to yeast IRE1 protein and include such annotation. The region corresponding to this EST cDNA was amplified by PCR from *Aspergillus nidulans* genomic DNA with the oligonucleotides 5' CGG AGG CAA GAG TCA TAG ACG 3 (forward primer) (SEQ ID No. 53) and 5' CAA TAT ATT TCT GAA CCA GTA CG 3' (reverse primer) (SEQ ID No. 54). The PCR reaction was carried out as described in Example 2. The resulting PCR fragment was cloned into the pCR2.1 vector with the TOPO TA cloning kit (Invitrogen) as instructed by the manufacturer. It was sequenced with internal oligonucleotide primers. The fragment was used as a probe in isolation of the *T. reesei* IRE1 gene. Optimal hybridization conditions were first determined with Southern hybridization of genomic *T. reesei* DNA as described in Example 3. A *T. reesei* genomic library constructed in λEMBL3 (Kaiser and Murray, 1985, in *DNA Cloning: a Practical Approach*, pp. 1-47, ed. Glover, IRL Press, Oxford) was then plated with the appropriate *E. coli* host strain and λ-DNA was lifted onto nitrocellulose filters (Schleicher & Schull) as instructed by the manufacturer. The filters were hybridized over night at 50° C. in a mix containing 6×SSC, 5×Denhardt's, 0.5% SDS, 100 µg/ml herring sperm DNA (SSC is 0.15 M NaCl, 0.015 M Na.citrate, pH 7.0, 50×Denhardt's is 1% Ficoll, 1% polyvinylpyrrolidone, 1% bovine serum albumin). The filters were washed for 10 minutes at room temperature with 2×SSC, 0.1% SDS and for 30 minutes at 50° C. with the same solution. λ-DNA was isolated from clones hybridizing with the probe with a described method (Sambrook et al., 1989).

Most of the protein-coding region of the genomic IRE1 gene was subcloned into pBluescript SK− as 2.1 kb and 2.4 kb BamHI fragments with methods known in the art. These fragments were sequenced with synthetic oligonucleotide primers. The two subclone fragments do not cover the whole open reading frame, and thus the 5' end of the chromosomal gene was sequenced from DNA isolated from the λ-clone isolated from the genomic library. An IRE1 cDNA was isolated from a *T. reesei* library constructed in λZAP (Stratagene). The cDNA library was plated with the appropriate *E. coli* host and lifted onto nitrocellulose filters (Schleicher & Schüll) as instructed by the manufacturer. The probe fragment used in the screening was obtained by digesting the 2.4 kb genomic subclone plasmid with BamHI and SmaI. The fragment of about 600 bp was run in a 0.8% agarose gel and isolated from the gel with the Qiaguick gel extraction kit (Qiagen) with manufacturer's instructions. The probe was labelled with $^{32}$P-dCTP with the Random Primed DNA labelling kit (Boehringer Mannheim). The filters were hybridized at 42° C. over night in a hybridization mixture containing 50% formamid, 5×Denhardt's, 5×SSPE, 0.1% SDS, 100 µg/ml herring sperm DNA and 1 µg/ml polyA-DNA (SSPE is 0.18 M NaCl, 1 mM EDTA, 10 mM NaH$_2$PO$_4$, pH 7.7). The filters were washed for 10 minutes at room temperature with 2×SSC, 0.1% SDS and for 30 minutes at 65° C. in 0.1×SSC, 0.1% SDS. λ-clones giving a hybridization signal were converted into pBluescript plasmids by in vivo-excision as instructed (Stratagene). The *T. reesei* IRE1 cDNA was sequenced from one of the plasmids with internal oligonucleotide primers.

The area sequenced from the *T. reesei* IRE1 gene is about 4.5 kb, and the open reading frame encodes a protein of 1233 amino acids (FIG. 27). Comparison of the genomic and cDNA sequences revealed one intron. The *T. reesei* IREI protein starts with a predicted signal sequence of 25 amino acids. There is a putative transmembrane segment at positions 574-596 of the open reading frame. The N-terminal domain (before the transmembrane segment) presumably facing the lumen of the endoplasmic reticulum has 24% identity and 39% similarity over an area of 377 amino acids with yeast IRE1p. The C-terminal part with the kinase and RNAse domains is 42% identical and 59% similar over an area of 490 amino acids to yeast IRE1p. The cloned *A. nidulans* ireA fragment is 1570 bp in length (FIG. 26). It encodes the kinase and RNAse domains of the IREA protein. Based in comparison with the yeast and *T. reesei* IRE1 sequences, an intron is identified in the sequence of the ireA fragment. The deduced *A. nidulans* IREA amino acid sequence has 52% identity over an area of 507 amino acids to the *T. reesei* IREI protein.

Example 12

Cloning and Constitutive Expression of the *Aspergillus niger* Var. *awamori* hacA cDNA The *A. niger* var. *awamori* hacA cDNA was isolated by heterologous hybridisation with the cloned *Aspergillus nidulans* hacA fragment described in Example 3. A cDNA library constructed from *A. niger* var. *awamori* RNA in the plasmid pYES2 (Invitrogen) was plated as *E. coli* colonies, lifted onto nitrocellulose filters and screened by colony hybridisation as described for the isolation of the *T. reesei* hac1 cDNA in Example 3. The hybridisation and the final washes were performed at 57° C. Positive colonies were found and examined by restriction analysis and sequencing of the cDNA ends. The longest cDNA was sequenced throughout its length from both strands. It is 1.68 kb long and encodes a protein of 342 amino acids (FIG. 28). The encoded protein has 76% identity with *A. nidulans* HACA protein and 38% identity with *T. reesei* HACI protein. The *A. niger* var. *awamori* hacA cDNA has an upstream open reading frame encoding 44 amino acids. The region of the cDNA that, according to homology with the *T. reesei* and *A. nidulans* hac1/A genes, had a 20 bp intron was sequenced from five of the *A. niger* var. *awamori* hacA cDNA clones isolated. One of these clones did not have the 20 bp intron present, showing that the intron can be spliced out as is shown in Example 4 for the 20 bp introns of *T. reesei* hac1 and *A. nidulans* hacA genes.

The UPR-induced form of the *A. niger* var. *awamori* hacA cDNA was expressed in *A. niger* var. *awamori* strains producing *Trametes versicolor* laccase or bovine preprochymosin which were constructed in the following manner. Strains ΔAP3 and ΔAP4 (described in Berka, R. M. et al., 1990, Gene 86:153-162) are equivalent strains which are deleted for the pepA gene (encoding the major extracellular aspartic proteinase) and which have a pyrG null mutation.

Strain ΔAP3 was transformed with pUCpyrGRG3 to create strain ΔAP3pUCpyrGRG3#11 which produces bovine preprochymosin. This strain secretes and accumulates active chymosin (an aspartic proteinase) in the culture medium. The plasmid, pUCpyrGRG3, consists of the GRG3 expression cassette (encoding the *Aspergillus niger* glaA promoter, preprochymosin open reading frame and glaA terminator) obtained from pGRG3 (Cullen, D. et al., 1987, Bio/Technology 5:369-376) and the *Neurospora crassa* pyr4 gene inserted into pUC19. Transformants of strain ΔAP3 with this plasmid were selected on the basis of uridine auxotrophy. Transformants were screened in liquid culture for chymosin production and strain ΔAP3pUCpyrGRG3#11 was chosen as the best producer.

Strain ΔAP4 was transformed with pGPT-LCC1 to create strain ΔAP4:pGPTlaccase which secretes *Trametes versicolor* laccase 1. The plasmid, pGPT-LCC1, is a derivative of plasmid pGPTpyrG1 (described in Berka, R. M. and Barnett, C. C., 1989, Biotechnol. Adv. 7:127-154) which contains the *N. crassa* pyr4 gene as fungal selectable marker and the *A. niger* glaA promoter and *A. niger* var. *awamori* glaA terminator region separated by cloning sites. To create pGPT-LCC1 the open reading frame for the *Trametes versicolor*

Icc1 cDNA (Ong, E. et al., 1997, Gene 196:113-119) was inserted between the glaA promoter and terminator regions in pGPTpyrG1. Transformants of strain ΔAP4 with this plasmid were selected on the basis of uridine auxotrophy. Transformants were screened in liquid culture for laccase production and strain ΔAP4:pGPTlaccase was chosen as the best producer.

Figure 29:
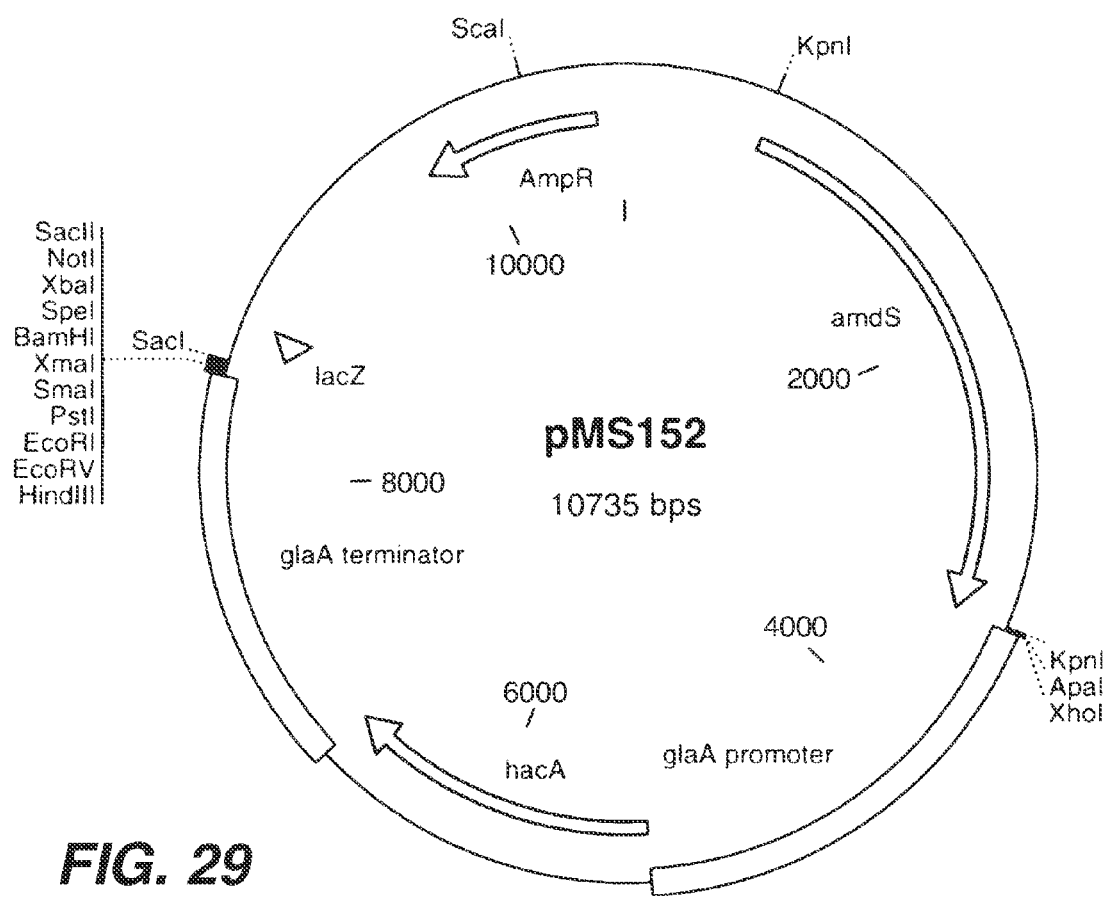
FIG. 29. Map of the plasmid pMS152 where the *Aspergillus niger* var. *awamori* hacA without the 5' flanking region and the 20 bp intron is under control of the *Aspergillus niger* var. *awamori* glaA promoter.

For the over expression of hacA, the induced form of the *A. niger* var. *awamori* hacA cDNA was first created by deleting the 20 by intron and truncating the 5' flanking region by about 150 bp, which omitted the upstream open reading frame. This was done by methods known in the art. The resulting hacA gene fragment was then cloned into an *A. niger* var. *awamori* expression vector with methods known in the art. In the final expression construct, pMS152 (FIG. 29), the hacA gene fragment is between the *A. niger* var. *awamori* glaA (glucoamylase gene) promoter and terminator. The *A. nidulans* amdS gene endoding acetamidase was in the plasmid as a selection marker for fungal transformation.

The hacA overexpression construct (pMS152) was transformed into either *A. niger* var. *awamori* strain ΔAP3pUCpyrGRG3#11 or strain ΔAP4:pGPTlaccase. The transformations were performed as described in Penttila et. al., 1987, Gene 61, 155-164. The transformants were selected for the ability to grow on acetamide as the sole nitrogen source. Transformants were passaged three times on selective medium before they were sporulated and single spores were plated on the selective medium.

For Southern analysis the purified transformants and the parental strains were grown in shake flasks (28° C., 200 rpm) in Clofine special medium (described in WO 98/31821). Mycelial samples for total-DNA isolations were collected on the third cultivation day. The isolations were done with the DNA EASY kit (Invitrogen) according to the manufacturer's instructions. 5 μg of the total DNA was cut with restriction enzyme HindIII and XhoI to obtain a 5.2 kb-fragment from the integrated pMS152 to indicate which transformants have the hacA overexpression cassette and samples were run in 1% agarose gel in 1×TBE-buffer. The treatment of the gels and capillary blotting onto a Hybond-N nylon filter (Amersham) were done as instructed by the manufacturer. A fragment of the *A. niger* var. *awamori* hacA cDNA labeled as described in Example 3 was used as a probe in the Southern hybridisation. The filters were hybridised at 42° C. over night in a hybridisation mixture containing 50% formamide, 5×Denhardt's, 5×SSPE, 0.1% SDS, 100 μg/ml herring sperm DNA and 1 μg/ml poly (A)-DNA. Filters were washed as described in Example 4. A band of the expected size was obtained from all the transformants that were analysed, but not from the parental strains. This indicated that the obtained transformants were stable and that they contained intact hacA overexpression cassette.

Eight transformants from the laccase-producing strain and four transformants from the chymosin-producing strain shown to contain the hacA overexpression cassette were cultivated again for Northern analysis and measurement of the enzymatic activities. The pMS152 transformants of the strain producing preprochymosin and the untransformed parental strain (ΔAP3pUCpyrGRG3#11) were cultivated in Clofine special medium in shake flasks (28° C., 200 rpm) in two parallel cultures for six days. Mycelial samples for RNA isolations were taken on the third day of the cultivation. The pMS152 transformants of the strain producing *Trametes* laccase and the untransformed parental strain (ΔAP4:pGPTlaccase) were cultivated in 8 g/liter Bacto Soytone (Difco), 12 g/liter Tryptone peptone (Difco), 15 g/liter $(NH_4)_2SO_4$, 12.1 g/liter $NaH_2PO_4.H_2O$ and 3.3 g/liter $Na_2HPO_4.7H_2O$. After autoclaving 5 ml/liter of 20% $MgSO_4$ solution, 2 ml/liter of Cu/citrate solution (110 g/liter citrate*$H_2O$, 125 g/liter $CuSO_4.5H_2O$), 1 ml/liter Tween 80, 300 ml/liter 50% maltose solution and 200 ml/liter of 100 mg/liter arginine was added to the medium. The cultivations were done in shake flasks (28° C., 200 rpm) in two parallel cultures for ten days. The mycelial samples for RNA isolations were taken on the second day of the cultivation. Total RNA's were isolated from all the mycelial samples using the TRIZOL reagent (Gibco-BRL) as instructed by the manufacturer. RNA samples of 5 μg were treated with glyoxal and run in 1% agarose gel in 10 mM Na-phosphate buffer, pH 7.0. Northern blottings and hybridizations were done as described in Example 4. A fragment of the *A. niger* var. *awamori* hacA cDNA labeled as described in Example 3 was used as a probe. An mRNA of the expected size from the hacA overexpression cassette of about 1.6 kb was observed in all the transformants studied in addition to the band of about 1.7 kb that is derived from the native hacA gene and that is also seen in the controls. This indicates that the 5'-truncated and intronless hacA coming from the overexpression cassette is expressed in the transformants.

Example 13

Figure 30:
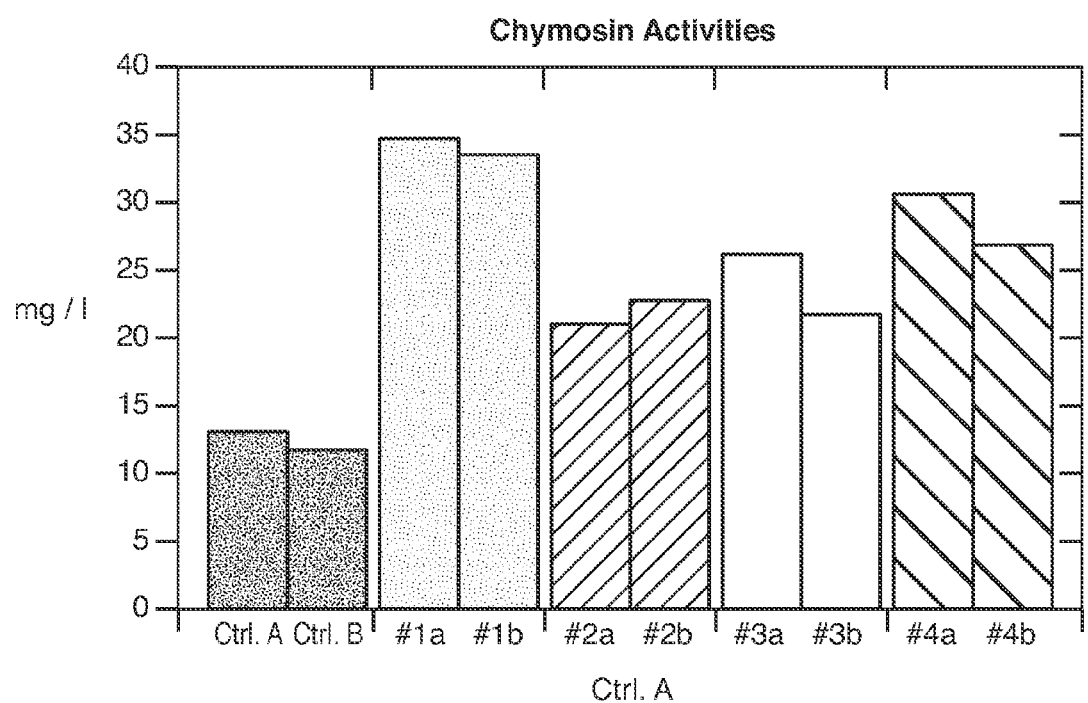
FIG. 30. The levels of chymosin activity measured in supernatants from duplicate cultures of strain ΔAP3pUCpyrGRG3#11 (ctrl) and transformants (#1, #2, #3 and #4) of this strain with pMS152.

The Effect of *A. Niger* Var. *awamori* hacA Overexpression on Heterologous Protein Production Samples from the culture supernatants of the pMS152 transformants of the strain producing preprochymosin and the untransformed parental strain (ΔAP3pUCpyrGRG3#11) were taken on the fifth day of cultivation. The chymosin production levels were measured with a milk-clotting assay. The samples were diluted into buffer containing 10 g/liter sodium acetate and 5 ml/liter 1M acetic acid. 200 μl of the diluted sample was added to 5 ml of buffer containing 55 g/500 ml skim milk (Difco) at 30° C. The clotting of the milk was observed visually and the time that the clotting of the milk took was recorded and correlated to a known standard. All the four transformants produced 1.3-2.8 fold more chymosin than the parental strain (FIG. 30).

Figure 31:
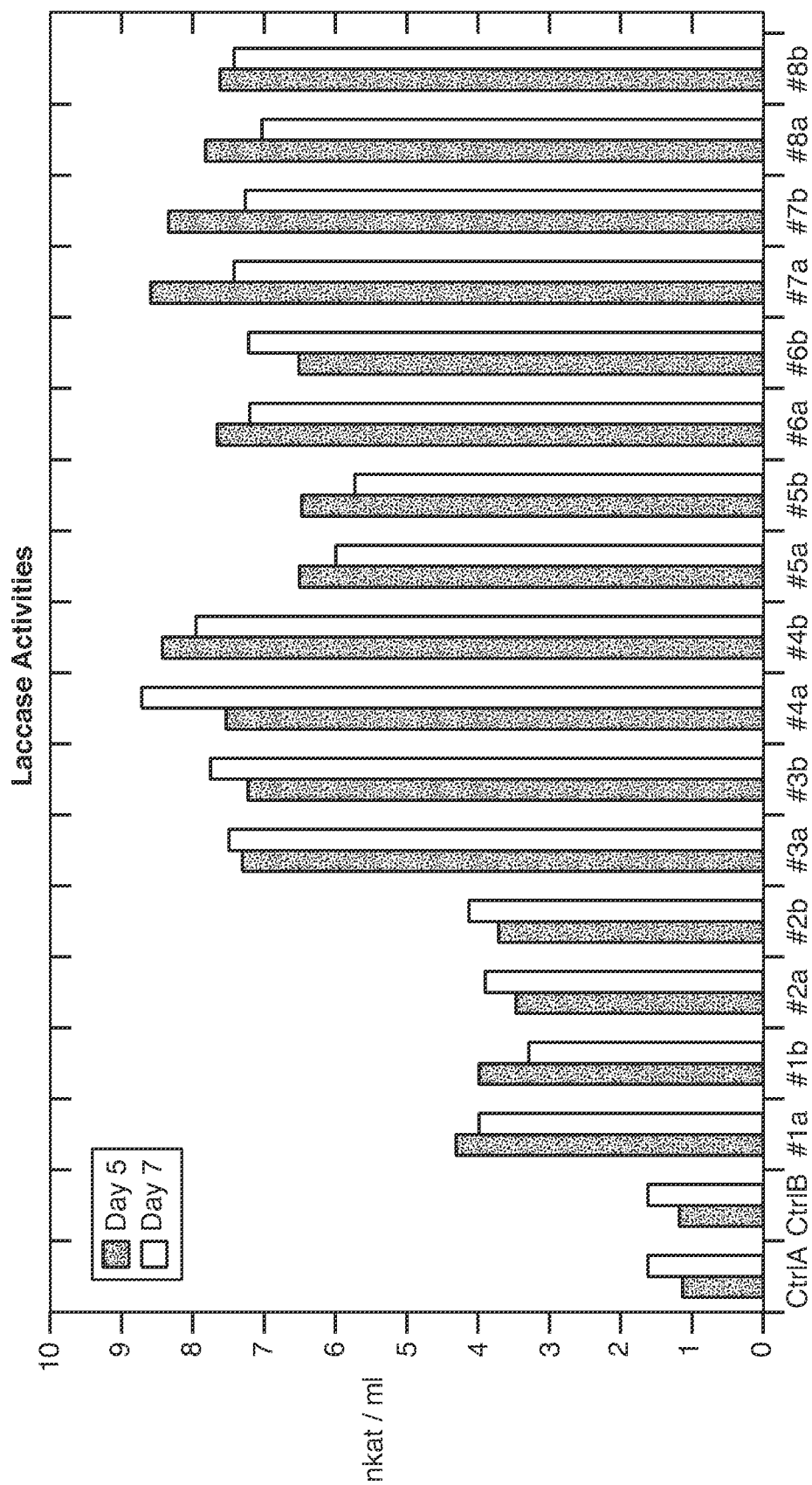
FIG. 31. The levels of laccase activity measured in supernatants from duplicate cultures of strain ΔAP4:pGPTlaccase (ctrl) and transformants (#1, #2, #3, #4, #5, #6, #7 and #8) of this strain with pMS152.

Samples from the culture supernatants of the pMS152 transformants of the strain producing *Trametes* laccase and the untransformed parental strain (ΔAP4:pGPTlaccase) were taken on the fifth and seventh day of the cultivation. The laccase activity measurements were made from the supernatants and the results showed that all the transformants produce more laccase than the parental strain. Laccase activity was measured according to Niku-Paavola et al. (Niku-Paavola M-L, Karhunen E, Salola P, Raunio V (1988) Ligninolytic enzymes of the white-rot fungus *Phlebia radiata*. Biochem. J. 254: 877-884) using ABTS (Boehringer Mannheim; Mannheim, Germany) as a substrate. The production levels of the transformants in the fifth day samples were 3 to 7.6 fold higher than in the parental strain. On the seventh day of cultivation the transformants produced 2 to 5.4 fold more laccase than the parental strain (FIG. 31).

These results demonstrate that overexpression of an inducing form of hacA enables production of higher levels of secreted heterologous proteins in *A. niger*.

Although the foregoing invention has been described in some detail by way of illustration and example for purposes of clarity and understanding, it will be obvious that certain changes and modifications may be practiced within the scope of the appended claims.

What is claimed is:

1. A cell containing a heterologous yeast or filamentous fungal nucleic acid encoding a protein comprising a DNA binding domain consisting of:
   a) at least 95% sequence identity to the DNA binding domain of amino acid sequence of SEQ ID NO: 5; or
   b) at least 95% sequence identity to the DNA binding domain of amino acid sequence of SEQ ID NO:19, and
a heterologous nucleic acid encoding a protein of interest to be secreted.

2. The cell of claim 1 wherein said protein of interest is selected from the group consisting of lipase, cellulase, endoglucosidase H, protease, carbohydrase, reductase, oxidase, isomerase, transferase, kinase, phosphatase, alpha-amylase, glucoamylase, lignocellulose hemicellulase, pectinase and ligninase.

3. The cell of claim 1, wherein the protein comprising a DNA binding domain is constitutively produced.

4. The cell of claim 1, wherein the protein comprising a DNA binding domain is encoded by a nucleic acid isolated from a cell selected from the group consisting of *Aspergillus, Trichoderma, Saccharomyces, Schizosaccharomyces, Kluyveromyces, Pichia, Hansenula, Fusarium, Neurospora*, and *Penicillium*.

5. The cell of claim 1, wherein the protein comprising a DNA binding domain is encoded by a nucleic acid isolated from filamentous fungi.

6. The cell of claim 5, wherein said fungi is *Trichoderma reesei*.

7. The cell of claim 1 wherein the DNA binding domain of SEQ ID NO:5 comprises amino acid residues 84-147 of SEQ ID NO: 5.

8. The cell of claim 1, where in the DNA binding domain of SEQ ID NO:19 comprises amino acid residues 45-109 of SEQ ID No:19.

* * * * *

SEQUENCE LISTING

<160> NUMBER OF SEQ ID NOS: 63

<210> SEQ ID NO 1
<211> LENGTH: 2417
<212> TYPE: DNA
<213> ORGANISM: Trichoderma reesei

<400> SEQUENCE: 1

| | | | | | |
|---|---|---|---|---|---|
| cgagaggcca | ctctgtcctc | ttctgcctga | ctcatcactc | ctcgacagca | tcaccaaggg | 60 |
| gaacgcactg | cacttggaca | cagccacgcc | gcttcccact | gactcatttg | ggactggcgc | 120 |
| cgttgcctgt | catgactgtt | cgcatcgtcg | tcatcaacca | tcgactgaca | cgcttcgctt | 180 |
| tgatttgatt | gcttctctct | ccactctctc | tcttcctgtc | tctctactac | tactactact | 240 |
| ctctcttctg | catctccacc | ggcctgtgac | cgaaaaaacc | aactccgtct | cctttcgaag | 300 |
| aagaaacagt | tggtccgacg | tcacaagcac | attcacaaaa | atcaaacaac | atatccccat | 360 |
| ctttcatata | caccacacgc | ttatgcagtg | agagagcacg | agagaagcat | cgtcataatc | 420 |
| aacacatcag | tcaaagcgaa | ctgcgctcgg | caacacgaca | cggcaggcaa | catggcgttc | 480 |
| cagcagtcgt | ctcccctcgt | caagtttgag | gcctctcccg | ccgaatcctt | cctctccgcc | 540 |
| cccggcgaca | acttcacatc | cctcttcgcc | gactcaacac | cctcaacact | taaccctcgg | 600 |
| gacatgatga | cccctgacag | cgtcgccgac | atcgactctc | gcctgtccgt | catccccgaa | 660 |
| tcacaggacg | cggaagatga | cgaatcacac | tccacatccg | ctaccgcacc | ctctacctca | 720 |
| gaaaagaagc | ccgtcaagaa | gaggaaatca | tggggccagg | ttcttcctga | gcccaagacc | 780 |
| aacctccctc | tcggtatgt | cactgcaaca | cggctcactt | gatacaactt | gcatcctaac | 840 |
| caaacgttac | tgtagaaaac | gtgcaaagac | ggaagatgaa | aaggagcagc | gccgcgtcga | 900 |
| gcgtgttctc | cgcaaccgcc | gcgccgcgca | gtcctcgcgc | gagcgcaaga | ggctcgaggt | 960 |
| cgaggctctc | gagaagcgca | acaaggagct | cgagacgctc | ctcatcaacg | tccagaagac | 1020 |
| caacctgatc | ctcgtcgagg | actcaaccgc | ttccgacgca | gctcaggcgt | cgtcacccgc | 1080 |
| tcgtcctccc | ccctcgactc | tctccaggac | agcatcactc | tctcccagca | actctttggc | 1140 |
| tcgcgggatg | ccaaaccat | gtccaacccc | gagcagtcct | tgatggacca | gatcatgaga | 1200 |
| tctgccgcta | accctaccgt | taacccggcc | tctctttccc | cctccctccc | cccatctcg | 1260 |
| gacaaggagt | tccagaccaa | ggaggaggac | gaggaacagg | ccgacgaaga | tgaagagatg | 1320 |
| gagcagacat | ggcacgagac | caaagaagcc | gccgccgcca | aggagaagaa | cagcaagcag | 1380 |
| tcccgcgtct | ccactgattc | gacacaacgt | cctgcagaga | tgttgtgcga | cccgcagtgt | 1440 |
| caatcggtgg | agatgccgct | gtccctgtct | tctcagacga | cgccggcgca | aactgccttg | 1500 |
| gcctggaccc | tgttcatcag | gatgatggtc | ctttcagcat | cggccattct | ttcggcctgt | 1560 |
| cagcggccct | tgatgcagat | cgctatctcc | tcgaaagcca | acttctcgct | tcgcccaacg | 1620 |
| cctcaactgt | tgacgacgat | tatctggctg | gtgactctgc | cgcctgcttc | acgaatcctc | 1680 |
| tccctccga | ctacgacttc | gacatcaacg | acttcctcac | agacgacgca | aaccacgccg | 1740 |
| cctatgacat | tgtggcagcg | agcaactatg | ccgctgcgga | ccgcgagctc | gacctcgaga | 1800 |
| tccacgaccc | tgagaatcag | atcccttcgc | gacattctat | ccagcagccc | cagtctggcg | 1860 |
| cgtcctctca | tggatgcgac | gatggcggca | ttgcggttgg | tgtctgaggg | acgcgacgat | 1920 |
| cggggcggga | tccggcctc | cgagtcttgt | gcgacgcgcg | gcgactgcga | gctggaacgg | 1980 |
| tgcctacgca | gcgtgacctt | gccgtctcga | gaagtcctca | tcaccctgtg | gtgggccgtg | 2040 |

-continued

```
aaggtggagg agaggaggat tcgcctgagg cagcacaaga agcaggccgc ggctctcgac    2100
cccgagaagc gcgcctcctt ggcagacaag aagaaccgac aacaacaaca acaacaacac    2160
cagtatcaga ttccttcgtt ttcaaaatag ttagcatatg tggtttttta atgggcaatg    2220
gggcggatgg caaacacggta gaggcaacaa gggttgacta cacctcccaa agggatacgg    2280
cgcacagcga ggttaatgac aaggctaaga tgggcctttt tttttatga tatgagaacc    2340 tcttcatctc cctttacact tctctctaga tggtagtgat gatatactgt accaaaatac    2400
aacgtctacc tagtgct                                                   2417

<210> SEQ ID NO 2
<211> LENGTH: 451
<212> TYPE: PRT
<213> ORGANISM: Trichoderma reesei

<400> SEQUENCE: 2

Met Ala Phe Gln Gln Ser Ser Pro Leu Val Lys Phe Glu Ala Ser Pro
 1               5                  10                  15

Ala Glu Ser Phe Leu Ser Ala Pro Gly Asp Asn Phe Thr Ser Leu Phe
            20                  25                  30

Ala Asp Ser Thr Pro Ser Thr Leu Asn Pro Arg Asp Met Met Thr Pro
        35                  40                  45

Asp Ser Val Ala Asp Ile Asp Ser Arg Leu Ser Val Ile Pro Glu Ser
    50                  55                  60

Gln Asp Ala Glu Asp Asp Glu Ser His Ser Thr Ser Ala Thr Ala Pro
65                  70                  75                  80

Ser Thr Ser Glu Lys Lys Pro Val Lys Lys Arg Lys Ser Trp Gly Gln
                85                  90                  95

Val Leu Pro Glu Pro Lys Thr Asn Leu Pro Pro Arg Lys Arg Ala Lys
            100                 105                 110

Thr Glu Asp Glu Lys Glu Gln Arg Arg Val Glu Arg Val Leu Arg Asn
        115                 120                 125

Arg Arg Ala Ala Gln Ser Ser Arg Glu Arg Lys Arg Leu Glu Val Glu
    130                 135                 140

Ala Leu Glu Lys Arg Asn Lys Glu Leu Glu Thr Leu Leu Ile Asn Val
145                 150                 155                 160

Gln Lys Thr Asn Leu Ile Leu Val Glu Glu Leu Asn Arg Phe Arg Arg
                165                 170                 175

Ser Ser Gly Val Val Thr Arg Ser Ser Pro Leu Asp Ser Leu Gln
            180                 185                 190

Asp Ser Ile Thr Leu Ser Gln Gln Leu Phe Gly Ser Arg Asp Gly Gln
        195                 200                 205

Thr Met Ser Asn Pro Glu Gln Ser Leu Met Asp Gln Ile Met Arg Ser
    210                 215                 220

Ala Ala Asn Pro Thr Val Asn Pro Ala Ser Leu Ser Pro Ser Leu Pro
225                 230                 235                 240

Pro Ile Ser Asp Lys Glu Phe Gln Thr Lys Glu Glu Asp Glu Glu Gln
                245                 250                 255

Ala Asp Glu Asp Glu Glu Met Glu Gln Thr Trp His Glu Thr Lys Glu
            260                 265                 270

Ala Ala Ala Ala Lys Glu Lys Asn Ser Lys Gln Ser Arg Val Ser Thr
        275                 280                 285

Asp Ser Thr Gln Arg Pro Ala Val Ser Ile Gly Gly Asp Ala Ala Val
    290                 295                 300

Pro Val Phe Ser Asp Asp Ala Gly Ala Asn Cys Leu Gly Leu Asp Pro
```

```
                305                 310                 315                 320
Val His Gln Asp Asp Gly Pro Phe Ser Ile Gly His Ser Phe Gly Leu
                    325                 330                 335

Ser Ala Ala Leu Asp Ala Asp Arg Tyr Leu Leu Glu Ser Gln Leu Leu
                340                 345                 350

Ala Ser Pro Asn Ala Ser Thr Val Asp Asp Tyr Leu Ala Gly Asp
        355                 360                 365

Ser Ala Ala Cys Phe Thr Asn Pro Leu Pro Ser Asp Tyr Asp Phe Asp
        370                 375                 380

Ile Asn Asp Phe Leu Thr Asp Asp Ala Asn His Ala Ala Tyr Asp Ile
385                 390                 395                 400

Val Ala Ala Ser Asn Tyr Ala Ala Ala Asp Arg Glu Leu Asp Leu Glu
                405                 410                 415

Ile His Asp Pro Glu Asn Gln Ile Pro Ser Arg His Ser Ile Gln Gln
                420                 425                 430

Pro Gln Ser Gly Ala Ser Ser His Gly Cys Asp Asp Gly Gly Ile Ala
            435                 440                 445

Val Gly Val
    450

<210> SEQ ID NO 3
<211> LENGTH: 1615
<212> TYPE: DNA
<213> ORGANISM: Aspergillus nidulans

<400> SEQUENCE: 3
gccatccttg gtgactgagc cccaacactt tcactggtcg ggatagtagc ctctggcttc     60
gattcgctat gacaccgtgg cctctgtcct aagtgactca ggcaaggcaa tcccagttcc    120
aactcccaac ttcgcaacct catcaaccac ctgcttccgt ctagttgcag ttatcagact    180
tgagttgtat gaaatcagca gaccggtttt cgccagtgaa aatggaggac gctttcgcaa    240
actctttgcc tactaccccg tcattggagg ttcctgtgct cactgtctcc ccggctgaca    300
catctcttcg gacgaagaat gtggtggctc agacaaagcc tgaggagaag aagccagcga    360
agaaaagaaa gtcctggggc caggaattac cagttcccaa gacaaactta cctccaaggt    420
gtgtgatacc tcaagagtca actccttact cctgctaata actaccacag aaaacgcgct    480
aagacagaag atgagaaaga gcagcgccgg attgagcgag ttcttcgcaa ccgcgcagcc    540
gcacaaacct ctcgcgagcg caagagactt gaaatggaga agttagaaag cgagaagatt    600
gatatggaac aacaaaacca gttccttctt cagcgtctcg cccagatgga ggctgagaac    660
aaccgtttaa gtcagcaagt tgctcagcta ccgcgcgagg ttcggggatc ccgccacagc    720
actccaactt ccagttcccc cgcgtcagtt tcgccaactc tcacaccgac tcttttttaag    780 caggaagggg atgaggttcc tctgaccgc atccctttc caactccctc cgtgaccgac    840
tactccccaa ctcttaagcc ttcatctctg gctgagtccc ccgatttgac acaacatcct    900
gcagcgatgt tgtgcgacct gcagtgtcag tcggcgggct cgaaggagat gaaagtgccc    960
tcacgctttt cgacctcgga gccagcatta agcatgagcc tacacatgac cttacagctc   1020
ctctttctga cgatgacttc cgccgcctat tcaacggtga ttcatccctt gagtcagatt   1080
cttcactcct tgaagacggg ttcgccttg acgttctcga ctcaggagat ttatcagcat   1140
ttccatttga ttctatggtt gattttgaca ccgagcctgt caccctcgaa gatctcgagc   1200
aaaccaacgg cctttcggat tcagcttctt gcaaggctgc tagcttgcaa cccagccatg   1260
gcgcgtccac ttcgcgatgc gacgggcagg gcattgcagc tggcagtgcg tgagaggttt   1320
```

-continued

```
tcgacggaag accgtctggt tcccgatgtt gtagagggtc gatggagctg ggaatccttg    1380
ttaacgctag cgtcggcgat aaatcttctt gagaaaccgg agcgacgaag aagaaccttg    1440
aggggtcttg attcgttaaa gcggggtcgg cgtattgatt cggggaagcg gtacagggtc    1500
atacggagtt cacggagttc aactagccca agagaggcgt tgacgtctcg gagaaagggc    1560
ttatgataat ttgtatatta gcgtgtccac tattcaatgt aagagcgagc aattg         1615
```

<210> SEQ ID NO 4
<211> LENGTH: 349
<212> TYPE: PRT
<213> ORGANISM: Aspergillus nidulans

<400> SEQUENCE: 4

```
Met Lys Ser Ala Asp Arg Phe Ser Pro Val Lys Met Glu Asp Ala Phe
  1               5                  10                  15

Ala Asn Ser Pro Thr Thr Pro Ser Leu Glu Val Pro Val Leu Thr Val
             20                  25                  30

Ser Pro Ala Asp Thr Ser Leu Arg Thr Lys Asn Val Val Ala Gln Thr
         35                  40                  45

Lys Pro Glu Glu Lys Lys Pro Ala Lys Lys Arg Lys Ser Trp Gly Gln
     50                  55                  60

Glu Leu Pro Val Pro Lys Thr Asn Leu Pro Pro Arg Lys Arg Ala Lys
 65                  70                  75                  80

Thr Glu Asp Glu Lys Glu Gln Arg Arg Ile Glu Arg Val Leu Arg Asn
                 85                  90                  95

Arg Ala Ala Ala Gln Thr Ser Arg Glu Arg Lys Arg Leu Glu Met Glu
            100                 105                 110

Lys Leu Glu Ser Glu Lys Ile Asp Met Glu Gln Gln Asn Gln Phe Leu
        115                 120                 125

Leu Gln Arg Leu Ala Gln Met Glu Ala Glu Asn Asn Arg Leu Ser Gln
    130                 135                 140

Gln Val Ala Gln Leu Ser Ala Glu Val Arg Gly Ser Arg His Ser Thr
145                 150                 155                 160

Pro Thr Ser Ser Ser Pro Ala Ser Val Ser Pro Thr Leu Thr Pro Thr
                165                 170                 175

Leu Phe Lys Gln Glu Gly Asp Glu Val Pro Leu Asp Arg Ile Pro Phe
            180                 185                 190

Pro Thr Pro Ser Val Thr Asp Tyr Ser Pro Thr Leu Lys Pro Ser Ser
        195                 200                 205

Leu Ala Glu Ser Pro Asp Leu Thr Gln His Pro Ala Val Ser Val Gly
    210                 215                 220

Gly Leu Glu Gly Asp Glu Ser Ala Leu Thr Leu Phe Asp Leu Gly Ala
225                 230                 235                 240

Ser Ile Lys His Glu Pro Thr His Asp Leu Thr Ala Pro Leu Ser Asp
                245                 250                 255

Asp Asp Phe Arg Arg Leu Phe Asn Gly Asp Ser Ser Leu Glu Ser Asp
            260                 265                 270

Ser Ser Leu Leu Glu Asp Gly Phe Ala Phe Asp Val Leu Asp Ser Gly
        275                 280                 285

Asp Leu Ser Ala Phe Pro Phe Asp Ser Met Val Asp Phe Asp Thr Glu
    290                 295                 300

Pro Val Thr Leu Glu Asp Leu Glu Gln Thr Asn Gly Leu Ser Asp Ser
305                 310                 315                 320

Ala Ser Cys Lys Ala Ala Ser Leu Gln Pro Ser His Gly Ala Ser Thr
```

```
                    325                 330                 335
Ser Arg Cys Asp Gly Gln Gly Ile Ala Ala Gly Ser Ala
                340                 345

<210> SEQ ID NO 5
<211> LENGTH: 451
<212> TYPE: PRT
<213> ORGANISM: Trichoderma reesei

<400> SEQUENCE: 5

Met Ala Phe Gln Gln Ser Ser Pro Leu Val Lys Phe Glu Ala Ser Pro
 1               5                  10                  15

Ala Glu Ser Phe Leu Ser Ala Pro Gly Asp Asn Phe Thr Ser Leu Phe
                20                  25                  30

Ala Asp Ser Thr Pro Ser Thr Leu Asn Pro Arg Asp Met Met Thr Pro
            35                  40                  45

Asp Ser Val Ala Asp Ile Asp Ser Arg Leu Ser Val Ile Pro Glu Ser
 50                  55                  60

Gln Asp Ala Glu Asp Glu Ser His Ser Thr Ser Ala Thr Ala Pro
65                   70                  75                  80

Ser Thr Ser Glu Lys Lys Pro Val Lys Lys Arg Lys Ser Trp Gly Gln
                85                  90                  95

Val Leu Pro Glu Pro Lys Thr Asn Leu Pro Pro Arg Lys Arg Ala Lys
            100                 105                 110

Thr Glu Asp Glu Lys Glu Gln Arg Arg Val Glu Arg Val Leu Arg Asn
        115                 120                 125

Arg Arg Ala Ala Gln Ser Ser Arg Glu Arg Lys Arg Leu Glu Val Glu
130                 135                 140

Ala Leu Glu Lys Arg Asn Lys Glu Leu Glu Thr Leu Leu Ile Asn Val
145                 150                 155                 160

Gln Lys Thr Asn Leu Ile Leu Val Glu Glu Leu Asn Arg Phe Arg Arg
                165                 170                 175

Ser Ser Gly Val Val Thr Arg Ser Ser Pro Leu Asp Ser Leu Gln
            180                 185                 190

Asp Ser Ile Thr Leu Ser Gln Gln Leu Phe Gly Ser Arg Asp Gly Gln
        195                 200                 205

Thr Met Ser Asn Pro Glu Gln Ser Leu Met Asp Gln Ile Met Arg Ser
210                 215                 220

Ala Ala Asn Pro Thr Val Asn Pro Ala Ser Leu Ser Pro Ser Leu Pro
225                 230                 235                 240

Pro Ile Ser Asp Lys Glu Phe Gln Thr Lys Glu Glu Asp Glu Glu Gln
                245                 250                 255

Ala Asp Glu Asp Glu Glu Met Glu Gln Thr Trp His Glu Thr Lys Glu
            260                 265                 270

Ala Ala Ala Ala Lys Glu Lys Asn Ser Lys Gln Ser Arg Val Ser Thr
        275                 280                 285

Asp Ser Thr Gln Arg Pro Ala Val Ser Ile Gly Gly Asp Ala Ala Val
290                 295                 300

Pro Val Phe Ser Asp Asp Ala Gly Ala Asn Cys Leu Gly Leu Asp Pro
305                 310                 315                 320

Val His Gln Asp Gly Pro Phe Ser Ile Gly His Ser Phe Gly Leu
                325                 330                 335

Ser Ala Ala Leu Asp Ala Asp Arg Tyr Leu Leu Glu Ser Gln Leu Leu
            340                 345                 350

Ala Ser Pro Asn Ala Ser Thr Val Asp Asp Tyr Leu Ala Gly Asp
```

-continued

```
                355                 360                 365
Ser Ala Ala Cys Phe Thr Asn Pro Leu Pro Ser Asp Tyr Asp Phe Asp
    370                 375                 380

Ile Asn Asp Phe Leu Thr Asp Asp Ala Asn His Ala Ala Tyr Asp Ile
385                 390                 395                 400

Val Ala Ala Ser Asn Tyr Ala Ala Asp Arg Glu Leu Asp Leu Glu
                405                 410                 415

Ile His Asp Pro Glu Asn Gln Ile Pro Ser Arg His Ser Ile Gln Gln
                420                 425                 430

Pro Gln Ser Gly Ala Ser Ser His Gly Cys Asp Asp Gly Gly Ile Ala
                435                 440                 445

Val Gly Val
    450

<210> SEQ ID NO 6
<211> LENGTH: 349
<212> TYPE: PRT
<213> ORGANISM: Aspergillus nidulans

<400> SEQUENCE: 6

Met Lys Ser Ala Asp Arg Phe Ser Pro Val Lys Met Glu Asp Ala Phe
1               5                   10                  15

Ala Asn Ser Pro Thr Thr Pro Ser Leu Glu Val Pro Val Leu Thr Val
                20                  25                  30

Ser Pro Ala Asp Thr Ser Leu Arg Thr Lys Asn Val Val Ala Gln Thr
            35                  40                  45

Lys Pro Glu Glu Lys Pro Ala Lys Arg Lys Ser Trp Gly Gln
50                  55                  60

Glu Leu Pro Val Pro Lys Thr Asn Leu Pro Pro Arg Lys Arg Ala Lys
65                  70                  75                  80

Thr Glu Asp Glu Lys Glu Gln Arg Arg Ile Glu Arg Val Leu Arg Asn
                85                  90                  95

Arg Ala Ala Ala Gln Thr Ser Arg Glu Arg Lys Arg Leu Glu Met Glu
                100                 105                 110

Lys Leu Glu Ser Glu Lys Ile Asp Met Glu Gln Gln Asn Gln Phe Leu
            115                 120                 125

Leu Gln Arg Leu Ala Gln Met Glu Ala Glu Asn Asn Arg Leu Ser Gln
130                 135                 140

Gln Val Ala Gln Leu Ser Ala Glu Val Arg Gly Ser Arg His Ser Thr
145                 150                 155                 160

Pro Thr Ser Ser Ser Pro Ala Ser Val Ser Pro Thr Leu Thr Pro Thr
                165                 170                 175

Leu Phe Lys Gln Glu Gly Asp Glu Val Pro Leu Asp Arg Ile Pro Phe
            180                 185                 190

Pro Thr Pro Ser Val Thr Asp Tyr Ser Pro Thr Leu Lys Pro Ser Ser
            195                 200                 205

Leu Ala Glu Ser Pro Asp Leu Thr Gln His Pro Ala Val Ser Val Gly
210                 215                 220

Gly Leu Glu Gly Asp Glu Ser Ala Leu Thr Leu Phe Asp Leu Gly Ala
225                 230                 235                 240

Ser Ile Lys His Glu Pro Thr His Asp Leu Thr Ala Pro Leu Ser Asp
                245                 250                 255

Asp Asp Phe Arg Arg Leu Phe Asn Gly Asp Ser Ser Leu Glu Ser Asp
            260                 265                 270

Ser Ser Leu Leu Glu Asp Gly Phe Ala Phe Asp Val Leu Asp Ser Gly
```

```
                275                 280                 285
Asp Leu Ser Ala Phe Pro Phe Asp Ser Met Val Asp Phe Asp Thr Glu
        290                 295                 300

Pro Val Thr Leu Glu Asp Leu Glu Gln Thr Asn Gly Leu Ser Asp Ser
305                 310                 315                 320

Ala Ser Cys Lys Ala Ala Ser Leu Gln Pro Ser His Gly Ala Ser Thr
                325                 330                 335

Ser Arg Cys Asp Gly Gln Gly Ile Ala Ala Gly Ser Ala
            340                 345

<210> SEQ ID NO 7
<211> LENGTH: 1265
<212> TYPE: DNA
<213> ORGANISM: Aspergillus nidulans

<400> SEQUENCE: 7
tttgaacagc agatcgttac tgcctaccca gacgttacag tccacgagct cacggaggac      60
gatgaattct tagtaatcgc ttgcgatggt gggtttcccc tcaactttgc cgctctgttc     120
cacaatctga tatactacag gaatctggga ttgccagtct tcccaagccg tggtcgaatt     180
cgttcgccgc ggtatcgcgg ccaagcagga tctctatcgg atttgtgaaa acatgatgga     240
caactgtctc gcttccaaca gtgagactgg tggagttggc tgtgacaaca tgacaatggt     300
cattataggt ctcctcaatg aaaaactaa ggaagagtgg tacaaccaga tcgcggagcg      360
ggttgctaac ggcgacggcc cttgtgctcc gcccgaatac ggcaagtctc tcgaggaacc     420
cacggcctcc aatccctact gactgaaccg tgggggttgc agctgaattc cgaggacctg     480
gaatccataa ccattttgaa gagaacccgg acgagtacga gatcgaccac gatcgctccc     540
gcccattcaa cgtgcgttct ggtagaataa ttcttttggg agatggcagc acgttaattc     600
caggaaaaca gaatgacgag gaactctttg accaaaccgg ggaggagaat cacccagacc     660
aagtgcaacg ccagaatacc gacacagaaa gaaatgaccg tgaagggacg cctgggcctc     720
aatccgcggc tccccagacg aacacgtccg cttcggatgg ctcagagcct tctaacacac     780
cgcagaaacc cgcctcttcg tagcttcgtc atgagattta cgcctgattc ccttcatttt     840
ggttcctgaa acgactcgtg atttcacgat ccacacccgc cgccccatct ccacgcccgg     900
tgccgaagcc tcacaattct gcccccatac ggtcgctcat tgattttctg tttctcacga     960
tttgaaggcg cattggtgct tgtgaccgcg aagatgcgaa agagacggac catatcatcc    1020
ccttctatct cttgttttaa tcccatcttc ttacttttta cgagctcatc cagatcaaat    1080
caccttcgtg ttactccagg atggatatct ttgagaattc gccgaatggg tggaggcatc    1140 ttcttccct gtcatctttc ttctctatgt ttgcacatgc cgcaagcggc aggcctcacg     1200
agagtacgtt tgtttcatgt ctcgacataa gataccgcaa caaccactat tgacgaactt    1260
tataa                                                                 1265

<210> SEQ ID NO 8
<211> LENGTH: 130
<212> TYPE: PRT
<213> ORGANISM: Aspergillus nidulans

<400> SEQUENCE: 8

Phe Glu Gln Gln Ile Val Thr Ala Tyr Pro Asp Val Thr Val His Glu
1               5                   10                  15

Leu Thr Glu Asp Asp Glu Phe Leu Val Ile Ala Cys Asp Gly Gly Ile
            20                  25                  30
```

```
Trp Asp Cys Gln Ser Ser Gln Ala Val Val Glu Phe Val Arg Arg Gly
            35                  40                  45

Ile Ala Ala Lys Gln Asp Leu Tyr Arg Ile Cys Glu Asn Met Met Asp
 50                  55                  60

Asn Cys Leu Ala Ser Asn Ser Glu Thr Gly Gly Val Gly Cys Asp Asn
 65                  70                  75                  80

Met Thr Met Val Ile Ile Gly Leu Leu Asn Gly Lys Thr Lys Glu Glu
                 85                  90                  95

Trp Tyr Asn Gln Ile Ala Glu Arg Val Ala Asn Gly Asp Gly Pro Cys
                100                 105                 110

Ala Pro Pro Glu Tyr Gly Lys Ser Leu Glu Glu Pro Thr Ala Ser Asn
            115                 120                 125

Pro Tyr
    130

<210> SEQ ID NO 9
<211> LENGTH: 1824
<212> TYPE: DNA
<213> ORGANISM: Trichoderma reesei

<400> SEQUENCE: 9
gacgagcctc gatccgcctc gacgccgctg gtttccccct tctttctccc cccttcagcc      60
acgtcctcgt gtcctataac cttcgcagc ctacggtccc gcctccagag gtctcgcgtc     120
cctgagtacc aaacgataga acaagactg ctatctttgt cgtgctgcct cctcccctcc     180
tcgacgcttt tcctccccct cgatcgcttt cccggccctc gtgagacgtc gcagccatgg     240
gccaaaccct ctcggagccc gttgtcgaaa agacttccga aaagggcgag atgacagac      300 tcatctacgg cgtgtccgcc atgcagggct ggcgcatcag catggaggac gctcacacgg     360
ctgagctgaa tctccccca cctgacaacg acaccaagac gcaccccgac aggctgtcct     420
ttttcggagt cttcgacgga cacggaggag acaaagtagc gttattcgca ggcgagaaca     480
ttcacaacat tgtttttcaag caggagagct tcaaatccgg tgattacgct cagggtctca     540
aggacggctt tctcgctacg gatcgggcta ttctcaacga ccccaaatac gaagaggaag     600
tctctggctg cactgcctgc gtcaccctga ttgccggaaa caaactatat gtcgccaacg     660
ccggtgattc tcgaagcgtg ctgggcatca agggacgggc caaacccta tccaacgacc     720 acaagcctca gcttgaaacg gagaagaacc gaatcacagc cgctggcggt ttcgtcgact     780
ttggccgagt caacggcaat ctggctctgt cgcgtgccat tggcgacttt gaattcaaga     840
agagcgccga gctgtccccc gaaaaccaga tcgttaccgc ctttcccgat gtcgaggtgc     900
acgagcttac agaggaggac gagttcctgg tgattgcctg tgacggtatc tgggattgcc     960
aatcttccca ggctgttgtt gagtttgtgc gacgaggcat cgccgccaag caggaccttg    1020
acaagatctg cgagaacatg atggacaact gccttgcgtc caactcagaa acgggtggcg    1080
tcggctgcga caacatgacc atggtcatca tcggcttcct gcacggcaag accaaggagg    1140
agtggtatga cgaaattgcc aagagagtgg ccaacggaga cggcccctgt gccccccgg     1200 aatatgccga gttccgcggt cccggcgttc accacaacta cgaagacagc gacagcggct    1260
acgacgtcga cgccgacagc ggcggcaagt ttagccttgc cggatccgg ggtcgcatca     1320 tcttcctggg cgacggcacc gaagtcctga cgggctccga cgacacggag atgtttgaca    1380
atgctgacga ggacaaggac cttgcgagcc aggtgcccaa gagctccggc aagaccgatg    1440
caaaggagga gacagaggcc aagccggcac agaggcggga gtcgtccaaa cccgcgatg     1500 ggtcggagaa gaagcaagac gaaaagagac accgaggagag taagaaggat taggtggtcc    1560
```

```
tcttgaattc tttgggctcg tctccttgaa gccccgcgct ggtgttgttg atggcgtgtg    1620
tttgtgtgta cgtgtggcat aattctttt tcttcccatc accgctactc aaaaaacccc    1680
aggcgtgagg gcatttttaa atcgcatagg gagtggggga gagacgggag aggctctgga    1740
acgaaacatt ctgggagaca aggcagagag cgtaggggcg gtttagacat tgagtgttgc    1800
tcgttaaaaa aaaaaaaaaa aaaa                                           1824
```

<210> SEQ ID NO 10
<211> LENGTH: 438
<212> TYPE: PRT
<213> ORGANISM: Trichoderma reesei

<400> SEQUENCE: 10

```
Met Gly Gln Thr Leu Ser Glu Pro Val Val Glu Lys Thr Ser Glu Lys
 1               5                  10                  15

Gly Glu Asp Asp Arg Leu Ile Tyr Gly Val Ser Ala Met Gln Gly Trp
                20                  25                  30

Arg Ile Ser Met Glu Asp Ala His Thr Ala Glu Leu Asn Leu Pro Pro
            35                  40                  45

Pro Asp Asn Asp Thr Lys Thr His Pro Asp Arg Leu Ser Phe Phe Gly
        50                  55                  60

Val Phe Asp Gly His Gly Gly Asp Lys Val Ala Leu Phe Ala Gly Glu
 65                  70                  75                  80

Asn Ile His Asn Ile Val Phe Lys Gln Glu Ser Phe Lys Ser Gly Asp
                85                  90                  95

Tyr Ala Gln Gly Leu Lys Asp Gly Phe Leu Ala Thr Asp Arg Ala Ile
               100                 105                 110

Leu Asn Asp Pro Lys Tyr Glu Glu Val Ser Gly Cys Thr Ala Cys
            115                 120                 125

Val Thr Leu Ile Ala Gly Asn Lys Leu Tyr Val Ala Asn Ala Gly Asp
        130                 135                 140

Ser Arg Ser Val Leu Gly Ile Lys Gly Arg Ala Lys Pro Leu Ser Asn
145                 150                 155                 160

Asp His Lys Pro Gln Leu Glu Thr Glu Lys Asn Arg Ile Thr Ala Ala
                165                 170                 175

Gly Gly Phe Val Asp Phe Gly Arg Val Asn Gly Asn Leu Ala Leu Ser
            180                 185                 190

Arg Ala Ile Gly Asp Phe Glu Phe Lys Lys Ser Ala Glu Leu Ser Pro
        195                 200                 205

Glu Asn Gln Ile Val Thr Ala Phe Pro Asp Val Glu Val His Glu Leu
    210                 215                 220

Thr Glu Glu Asp Glu Phe Leu Val Ile Ala Cys Asp Gly Ile Trp Asp
225                 230                 235                 240

Cys Gln Ser Ser Gln Ala Val Val Glu Phe Val Arg Arg Gly Ile Ala
                245                 250                 255

Ala Lys Gln Asp Leu Asp Lys Ile Cys Glu Asn Met Met Asp Asn Cys
            260                 265                 270

Leu Ala Ser Asn Ser Glu Thr Gly Gly Val Gly Cys Asp Asn Met Thr
        275                 280                 285

Met Val Ile Ile Gly Phe Leu His Gly Lys Thr Lys Glu Glu Trp Tyr
    290                 295                 300

Asp Glu Ile Ala Lys Arg Val Ala Asn Gly Asp Gly Pro Cys Ala Pro
305                 310                 315                 320

Pro Glu Tyr Ala Glu Phe Arg Gly Pro Gly Val His His Asn Tyr Glu
```

```
                      325                 330                 335
Asp Ser Asp Ser Gly Tyr Asp Val Asp Ala Asp Ser Gly Gly Lys Phe
            340                 345                 350
Ser Leu Ala Gly Ser Arg Gly Arg Ile Ile Phe Leu Gly Asp Gly Thr
            355                 360                 365
Glu Val Leu Thr Gly Ser Asp Thr Glu Met Phe Asp Asn Ala Asp
    370                 375                 380
Glu Asp Lys Asp Leu Ala Ser Gln Val Pro Lys Ser Ser Gly Lys Thr
385                 390                 395                 400
Asp Ala Lys Glu Glu Thr Glu Ala Lys Pro Ala Pro Glu Ala Glu Ser
                405                 410                 415
Ser Lys Pro Ala Asp Gly Ser Glu Lys Lys Gln Asp Glu Lys Thr Pro
            420                 425                 430
Glu Glu Ser Lys Lys Asp
        435

<210> SEQ ID NO 11
<211> LENGTH: 1570
<212> TYPE: DNA
<213> ORGANISM: Aspergillus nidulans

<400> SEQUENCE: 11
```

| | | | | | |
|---|---|---|---|---|---|
| cggaggcaag | agtcatagac | gcgggaagaa | gaaaattgag | agtgagaaag | aggaatctga | 60 |
| tcacgcccct | ggcaccttgc | aaccccggc | tgggcccgat | gccgggttag | ctctcacccg | 120 |
| cactgcatct | aatgaggtgt | ttgaagcgga | cggtgtcatc | cagattggcc | gtttgaaggt | 180 |
| ctttacggct | gacgttctgg | gtcatggaag | ccacgggaca | gttgtttacc | gcgggtcgtt | 240 |
| tgacggccga | gacgtcgcgg | tcaaacgtat | gctggtggag | ttctatgata | ttgcatcgca | 300 |
| cgaagtggga | ttgttgcagg | aaagcgatga | tcataacaac | gttatccgat | gttattgccg | 360 |
| tgagcaagcc | aagggtttct | tctacatcgc | ccttgaactg | tgtccggctt | ctttgcagga | 420 |
| tgtggtagaa | cgaccagacg | cgttcccgca | gctagtcaat | ggtggcttgg | atatgccgga | 480 |
| cgtcttgcgt | caaattgtcg | ccggtgtccg | gtacctacac | tctctcaaaa | tcgtacaccg | 540 |
| tgacttgaag | cctcaaaata | tcctggtcgc | cgctcctcga | ggccgtatcg | gttctcgggc | 600 |
| catccggctt | ctgatttcgg | actttggctt | gtgcaagaaa | cttgaggata | ccagagttc | 660 |
| attcagggca | accacggccc | atgctgctgg | tactccgggt | ggagggctcc | cgaactgctt | 720 |
| gtggatgacg | acaagagccg | gtaatcaggg | ttcagagtct | caaaatacgg | agtcatctga | 780 |
| gccggcggtc | gtcgatcccc | agacgaatcg | acgagccacc | cgagccattg | atatcttctc | 840 |
| cctgggatgt | gtcttctact | acgtcctaac | tcgaggatgt | catccttttg | acaagaatgg | 900 |
| caagttcatg | cgcgaagcaa | atatcgtcaa | ggggaatttc | aatctcgatg | agttacagcg | 960 |
| tctaggagag | tatgcgtttg | aagcagacga | tcttatccga | tcaatgttgg | cacttgatcc | 1020 |
| acgtcaacgg | tatgtcccaa | caacatcttc | ctttgccttg | tggcgtagcg | tactaatctc | 1080 |
| cacagccccg | acgcaagcgc | tgtgttaacc | catcctttct | tctggaatcc | gtccgaccgc | 1140 |
| cttagcttcc | tctgtgacgt | ttcggaccac | ttcgagttcg | aaccgagaga | tcctccatct | 1200 |
| gacgctcttc | tgtgtctaga | gtctgtagcc | tctgatgtca | ttggccctga | aatgaatcct | 1260 |
| caaactcctg | ccaaaggact | tcaaagacag | tctcggaagc | agcgaaaata | caccggctcc | 1320 |
| aaaatgctgg | acttgatgcg | agccctgcgg | aacaagcgca | accactacaa | tgatatgccg | 1380 |
| gagcatttga | aagctcatat | tggtgggctg | ccggagggtt | acttgaattt | ctggaccgtg | 1440 |
| cgtttcccga | gtttgctgat | gagttgtcat | tgggtgattg | ttgaactggg | attgacgaag | 1500 | acggatcggt tccaagagat attttacgcc attggagtag gttgttgcgt actggttcag    1560 aaatatattg                                                           1570

<210> SEQ ID NO 12
<211> LENGTH: 504
<212> TYPE: PRT
<213> ORGANISM: Aspergillus nidulans

<400> SEQUENCE: 12

Gly Gly Lys Ser His Arg Arg Gly Lys Lys Ile Glu Ser Glu Lys
 1               5                  10                  15

Glu Glu Ser Asp His Ala Pro Gly Thr Leu Gln Pro Ala Gly Pro
                20                  25                  30

Asp Ala Gly Leu Ala Leu Thr Arg Thr Ala Ser Asn Glu Val Phe Glu
            35                  40                  45

Ala Asp Gly Val Ile Gln Ile Gly Arg Leu Lys Val Phe Thr Ala Asp
 50                  55                  60

Val Leu Gly His Gly Ser His Gly Thr Val Val Tyr Arg Gly Ser Phe
 65                  70                  75                  80

Asp Gly Arg Asp Val Ala Val Lys Arg Met Leu Val Glu Phe Tyr Asp
                85                  90                  95

Ile Ala Ser His Glu Val Gly Leu Leu Gln Glu Ser Asp Asp His Asn
            100                 105                 110

Asn Val Ile Arg Cys Tyr Cys Arg Glu Gln Ala Lys Gly Phe Phe Tyr
        115                 120                 125

Ile Ala Leu Glu Leu Cys Pro Ala Ser Leu Gln Asp Val Val Glu Arg
    130                 135                 140

Pro Asp Ala Phe Pro Gln Leu Val Asn Gly Gly Leu Asp Met Pro Asp
145                 150                 155                 160

Val Leu Arg Gln Ile Val Ala Gly Val Arg Tyr Leu His Ser Leu Lys
                165                 170                 175

Ile Val His Arg Asp Leu Lys Pro Gln Asn Ile Leu Val Ala Ala Pro
            180                 185                 190

Arg Gly Arg Ile Gly Ser Arg Ala Ile Arg Leu Leu Ile Ser Asp Phe
        195                 200                 205

Gly Leu Cys Lys Lys Leu Glu Asp Asn Gln Ser Ser Phe Arg Ala Thr
    210                 215                 220

Thr Ala His Ala Ala Gly Thr Pro Gly Gly Gly Leu Pro Asn Cys Leu
225                 230                 235                 240

Trp Met Thr Thr Arg Ala Gly Asn Gln Gly Ser Glu Ser Gln Asn Thr
                245                 250                 255

Glu Ser Ser Glu Pro Ala Val Val Asp Pro Gln Thr Asn Arg Arg Ala
            260                 265                 270

Thr Arg Ala Ile Asp Ile Phe Ser Leu Gly Cys Val Phe Tyr Tyr Val
        275                 280                 285

Leu Thr Arg Gly Cys His Pro Phe Asp Lys Asn Gly Lys Phe Met Arg
    290                 295                 300

Glu Ala Asn Ile Val Lys Gly Asn Phe Asn Leu Asp Glu Leu Gln Arg
305                 310                 315                 320

Leu Gly Glu Tyr Ala Phe Glu Ala Asp Asp Leu Ile Arg Ser Met Leu
                325                 330                 335

Ala Leu Asp Pro Arg Gln Arg Pro Asp Ala Ser Ala Val Leu Thr His
            340                 345                 350

Pro Phe Phe Trp Asn Pro Ser Asp Arg Leu Ser Phe Leu Cys Asp Val

-continued

```
                355                 360                 365
Ser Asp His Phe Glu Phe Glu Pro Arg Asp Pro Ser Asp Ala Leu
    370                 375                 380
Leu Cys Leu Glu Ser Val Ala Ser Asp Val Ile Gly Pro Glu Met Asn
385                 390                 395                 400
Pro Gln Thr Pro Ala Lys Gly Leu Gln Arg Gln Ser Arg Lys Gln Arg
                405                 410                 415
Lys Tyr Thr Gly Ser Lys Met Leu Asp Leu Met Arg Ala Leu Arg Asn
                420                 425                 430
Lys Arg Asn His Tyr Asn Asp Met Pro Glu His Leu Lys Ala His Ile
                435                 440                 445
Gly Gly Leu Pro Glu Gly Tyr Leu Asn Phe Trp Thr Val Arg Phe Pro
    450                 455                 460
Ser Leu Leu Met Ser Cys His Trp Val Ile Val Glu Leu Gly Leu Thr
465                 470                 475                 480
Lys Thr Asp Arg Phe Gln Glu Ile Phe Tyr Ala Ile Gly Val Gly Cys
                485                 490                 495
Cys Val Leu Val Gln Lys Tyr Ile
            500

<210> SEQ ID NO 13
<211> LENGTH: 4528
<212> TYPE: DNA
<213> ORGANISM: Trichoderma reesei

<400> SEQUENCE: 13
gcacgagcaa gatacggcct ctcgcaccaa ggagacacgc atattcgtgg taccatcggc      60
tgagggtgaa gggggggttca acacagcaca actcagcgac cactggactg gtggagccga    120
agcccacgat cgaatccaca gcctgcacca ctttctcctc gtcatattcg cggggactca    180
caagcggttt ccgttgcctt cgaattcgac agagctgcga ctgcgagtca tttcagcgac    240
tctaaaccta ctcctttggc tgctgcgcgg gactggttct gcccagcctc tcctactcga    300
ccaaccgacg tcctctttct gcttcctcat ccctttctcc tttgacgtcc gagcgtcaga    360
gcgaattttt ccttgcttct tcgtttgggc cgggaatggc ttctctggca tcgcaacagc    420
ctctaccgct ccgttggtag agccatagcc tgcagctccc catgtgatcc gctctccgtc    480
tctccggcac cccgactttc gtctcgatca tgatgcggcg accccgagc caaggacgat     540
ggtccgcgtc gcatcagaag ctctcctggc ttttgccttt attctcatac catggctcca    600
acttgccgat gctcagcagc agcctcagca gccccagatt cgaattcact acaaagagg     660
cgacgcgccc cttgacaaag tcgccgacga tgccaacacc cgttggtacg caacacatgc    720
tgcaccagac gtgcaccccg aagcgaagtt cgacaccgtc aacaggaagc aaaagcagca    780
gtcgaccgct tcgccccagc aacaccagaa atatcgacga gccccctatg actacgccag    840
caaggacaag gcccagaacc gatatgcgca gcaccctatc cgcgaatccg agaaaccaaa    900
ctacgtaaaa gtccccaacg atgcgagcgc cctcgcaact ttagctccgg ctcagcccgt    960
ccgagcacca cacacctcac gacatcactg gcccagcagc agcgccgctt ctgggctggc   1020
ctcgccgcac aatgcgcgga gtctggagga ctgggaagtt gaagactttg ttcttctggc   1080
gaccgtcgat ggagacctct atgccagcga ccgaaagacc ggtcggcacc tctggcacct   1140
cgaggtcgac cagccagtgg ttgaaaccaa acactaccga acaaacaact ccgtcctcga   1200
cgacgactat cgccccgtcg accactacat ctggccgtc gagccgagcc gcgatggagg    1260
gctctatgta tggatccccg actccggagc gggcctcgtc aggaccggct tcaccatgaa   1320
```

```
gcacctcgtt gaagaacttg ctccatacgc cggcgacgag cccccgttg tctataccgg    1380 agacaagaag acgaccatgg tcaccctgga cgccgctacc gggcgcgttc tcaaatggtt    1440
tggctctagc ggctcccaag tcaacgaagc cgagagctgc cttcggccca atgcctttga    1500
cgacagggat accacagagt gcagctccat gggcacaatc acgctgggaa ggaccgagta    1560
cacggtgggc atccgaggc gagacggtcg ccctatcgca accttgaagt acgcagaatg    1620
gggacccaac acctttgaca gcgacctcta ccagcaatac cacgcctcgt tggacaacca    1680
ttacatcacc agtcagcacg acgggagaat ttacgcgttt gacaagtcac aggcagaaaa    1740
cgacctgccc ctctacaccc acaagttttc gtctcccgtc gcccgggtct tcgatgtctg    1800
tcgaccgtgg gatgcgaatg cgggaagcaa cccggagctg gtggttctcc cccaacctcc    1860
aattccagcg cttgatgaga gcactgtcaa gatgcgaagc aacagcatct tcctcaacca    1920
gactgaaagc ggcgactggt atgcgctctc cggccgtgcg tatccgctta tactcgatgc    1980
ccccgtggcc cagatctcgc gggacgactt gtgggatatg gccatgcct ttgattccat    2040 taacccaaat aagctgtcca aggccctggt gggaacccac tttctgaatc ccgtcaagag    2100
caccggttac catcagccgc cgacgctccc tgccggcgcc ctcgacgagt attacgagga    2160
cttggagaac gcctcaaaca atgctcacgc cgtgacaaac actgttccgg aggagcccac    2220
catcatcacc aaagtcaagg ctcttccgca gagtgctgcg aacagcgtca ttgactttgt    2280
cagcaacccc attctcatca tttttcttgat aggctccttg atctacaacg aaaagaagct    2340
gcgacggtcg tatcatcggt tccggactca tggcacaatc aaggacgtct atcccttctt    2400
cgttatcgaa tctgaggccg agatgaatc aggtgatgac aaggacggtg tgttcccatc    2460
ttcgccgtct ccgcgcagtc aaccccagga ccaaaatgcg gaagaccacc tgtccagaca    2520
caaggtggag aggaatgccg gcgaccagga caaggtcaag gacaacagga gcctgcatga    2580
cgtttctgac accttggaac cgagcaacaa gactgttgag aaaacggccg atgtggtcaa    2640
gcaagtggat gtagctggcc ctgacgcacc ctcgacggac tccaatggtg ctgcaccgga    2700
gaagaagaag aaggctcacc gaggccgtcg tggcggtgtc aagcacagaa agggtcggcc    2760
caccgacggc tcgcagtctc atgaaaacga cccagctctc actacagtgg acgaggctgt    2820
aagcaatgcg aagaagctgg gtgaccggcc aagcctggaa cccgacgtca tgaccatcta    2880
caacgacatg caagccgtca cgggctctgt tatcagcatg ggaaacatcg aggtcgatac    2940
ggatgtcgag cttggcatgg gcagcaacgg tactgtcgta tttgctggcc gattcgatgg    3000
cagggacgtc gccgtcaaga gaatgacgat tcagttctac gacattgcca cgcgagaaac    3060
taagttgctg cgcgagagtg acgaccaccc caatgtaaat cagccctcat cgtttcaccc    3120
attttccctt cgctaacgta accactgtct gcacgtcatt cggtattact cacaagtgca    3180
gcgaggcgac ttcctgtata ttgccttgga acgctgcgct gcttcattgg cagatgtcat    3240
tgaaaagccg tatgcctttg gtgaattggc caaggctgga caaaaggacc taccgggcgt    3300
cttgtaccaa atcaccaacg gcatcagcca cttgcactct ctgcggattg ttcatcgaga    3360
cttgaagcct caaaacatct tggtcaactt ggacaaggac ggcagaccaa ggctcttggt    3420
gtcggacttt ggcctgtgta agaaactgga ggatagacag tcttcgttcg gagcaacgac    3480
aggccgagcc gctggaacgt cgggatggcg tgccccgaa ctgcttctcg atgacgacgg    3540
acagaatccc gcagccatcg atagcagtac gcacagcggc tctcacacca tcctcgtggg    3600
agaccccaac tcgctttcca atggagggcg agccacgagg gccattgaca tcttctccct    3660
tggccttgtc ttcttctacg tgctcaccaa tggatcccac ccgtttgact gtggcgacag    3720
```

-continued

```
atatatgcgg gaggtgaaca ttcgaaaggg caactacaat ctcgatccat tggacgctct   3780
gggcgacttt gcctacgaag ccaaggatct gattgcgtcc atgctccagg cctctcccaa   3840
ggcacgaccc gactcgcgag aggtcatggc ccacccttc ttctggtctc cgaagaagcg    3900
tctggccttt tgtgcgacg tgtcggattc tctggagaag gaggtgcgag atcctccgtc    3960
gcctgccttg gtcgagctgg agcgacatgc gccggaggtc attaagggag acttcttgaa   4020
ggtgctcacg cgcgactttg tcgagtcgct gggcaagcag cgcaagtaca ccgggaacaa   4080
gctgctcgac ctgttgcgcg ctcttcgcaa caagcggaat cactacgaag acatgtcgga   4140
ctcgctgaag cgcagcgtgg gatcactgcc tgatgggtat cttgcttatt ggacggtcaa   4200
gttcccgatg ctgttgctga cgtgctggaa cgtggtgtat aatctcgagt gggagaagac   4260
ggatcggttc agggagtact atgagcctgc cggattgtag aagaaagaaa aggaagagaa   4320
aagaaaggcc tcttgcttgt ttggttgctg tatatctttt tgctcgaaga tggaaacgga   4380
aaatattggg gaagttgcat gggaagtgaa caaaagaggg gaaaaatggt gaatgtgaaa   4440
gcaaagtcgg ttagcgggtg ggcatggtcg tcatccatgt aattgtttca gcttctgttg   4500
catcaaaagc gttgtgtttt cgttctttt                                    4528
```

<210> SEQ ID NO 14
<211> LENGTH: 1232
<212> TYPE: PRT
<213> ORGANISM: Trichoderma reesei

<400> SEQUENCE: 14

```
Met Val Arg Val Ala Ser Glu Ala Leu Leu Ala Phe Ala Phe Ile Leu
  1               5                  10                  15

Ile Pro Trp Leu Gln Leu Ala Asp Ala Gln Gln Pro Gln Gln Pro
             20                  25                  30

Gln Ile Arg Ile His Ser Gln Arg Gly Asp Ala Pro Leu Asp Lys Val
         35                  40                  45

Ala Asp Asp Ala Asn Thr Arg Trp Tyr Ala Thr His Ala Ala Pro Asp
     50                  55                  60

Val His Pro Glu Ala Lys Phe Asp Thr Val Asn Arg Lys Gln Lys Gln
 65                  70                  75                  80

Gln Ser Thr Ala Ser Pro Gln Gln His Gln Lys Tyr Arg Arg Ala Pro
                 85                  90                  95

Tyr Asp Tyr Ala Ser Lys Asp Lys Ala Gln Asn Arg Tyr Ala Gln His
            100                 105                 110

Pro Ile Arg Glu Ser Glu Lys Pro Asn Tyr Val Lys Val Pro Asn Asp
        115                 120                 125

Ala Ser Ala Leu Ala Thr Leu Ala Pro Ala Gln Pro Val Arg Ala Pro
    130                 135                 140

His Thr Ser Arg His His Trp Pro Ser Ser Ala Ala Ser Gly Leu
145                 150                 155                 160

Ala Ser Pro His Asn Ala Arg Ser Leu Glu Asp Trp Glu Val Glu Asp
                165                 170                 175

Phe Val Leu Leu Ala Thr Val Asp Gly Asp Leu Tyr Ala Ser Asp Arg
            180                 185                 190

Lys Thr Gly Arg His Leu Trp His Leu Glu Val Asp Gln Pro Val Val
        195                 200                 205

Glu Thr Lys His Tyr Arg Thr Asn Asn Ser Val Leu Asp Asp Tyr
    210                 215                 220

Arg Pro Val Asp His Tyr Ile Trp Ala Val Glu Pro Ser Arg Asp Gly
```

```
            225                 230                 235                 240
Gly Leu Tyr Val Trp Ile Pro Asp Ser Gly Ala Gly Leu Val Arg Thr
                    245                 250                 255
Gly Phe Thr Met Lys His Leu Val Glu Glu Leu Ala Pro Tyr Ala Gly
                    260                 265                 270
Asp Glu Pro Pro Val Val Tyr Thr Gly Asp Lys Lys Thr Thr Met Val
                    275                 280                 285
Thr Leu Asp Ala Ala Thr Gly Arg Val Leu Lys Trp Phe Gly Ser Ser
            290                 295                 300
Gly Ser Gln Val Asn Glu Ala Glu Ser Cys Leu Arg Pro Asn Ala Phe
305                 310                 315                 320
Asp Asp Arg Asp Thr Thr Glu Cys Ser Ser Met Gly Thr Ile Thr Leu
                    325                 330                 335
Gly Arg Thr Glu Tyr Thr Val Gly Ile Gln Arg Arg Asp Gly Arg Pro
                    340                 345                 350
Ile Ala Thr Leu Lys Tyr Ala Glu Trp Gly Pro Asn Thr Phe Asp Ser
                    355                 360                 365
Asp Leu Tyr Gln Gln Tyr His Ala Ser Leu Asp Asn His Tyr Ile Thr
            370                 375                 380
Ser Gln His Asp Gly Arg Ile Tyr Ala Phe Asp Lys Ser Gln Ala Glu
385                 390                 395                 400
Asn Asp Leu Pro Leu Tyr Thr His Lys Phe Ser Pro Val Ala Arg
                    405                 410                 415
Val Phe Asp Val Cys Arg Pro Trp Asp Ala Asn Ala Gly Ser Asn Pro
                    420                 425                 430
Glu Leu Val Val Leu Pro Gln Pro Ile Pro Ala Leu Asp Glu Ser
                    435                 440                 445
Thr Val Lys Met Arg Ser Asn Ser Ile Phe Leu Asn Gln Thr Glu Ser
            450                 455                 460
Gly Asp Trp Tyr Ala Leu Ser Gly Arg Ala Tyr Pro Leu Ile Leu Asp
465                 470                 475                 480
Ala Pro Val Ala Gln Ile Ser Arg Asp Asp Leu Trp Asp Met Ala His
                    485                 490                 495
Ala Phe Asp Ser Ile Asn Pro Asn Lys Leu Ser Lys Ala Leu Val Gly
                    500                 505                 510
Thr His Phe Leu Asn Pro Val Lys Ser Thr Gly Tyr His Gln Pro Pro
                    515                 520                 525
Thr Leu Pro Ala Gly Ala Leu Asp Glu Tyr Tyr Glu Asp Leu Glu Asn
            530                 535                 540
Ala Ser Asn Asn Ala His Ala Val Thr Asn Thr Val Pro Glu Glu Pro
545                 550                 555                 560
Thr Ile Ile Thr Lys Val Lys Ala Leu Pro Gln Ser Ala Ala Asn Ser
                    565                 570                 575
Val Ile Asp Phe Val Ser Asn Pro Ile Leu Ile Phe Leu Ile Gly
                    580                 585                 590
Ser Leu Ile Tyr Asn Glu Lys Lys Leu Arg Arg Ser Tyr His Arg Phe
            595                 600                 605
Arg Thr His Gly Thr Ile Lys Asp Val Tyr Pro Phe Phe Val Ile Glu
            610                 615                 620
Ser Glu Ala Gly Asp Glu Ser Gly Asp Asp Lys Asp Gly Val Phe Pro
625                 630                 635                 640
Ser Ser Pro Ser Pro Arg Ser Gln Pro Gln Asp Gln Asn Ala Glu Asp
                    645                 650                 655
```

-continued

His Leu Ser Arg His Lys Val Glu Arg Asn Ala Gly Asp Gln Asp Lys
                660                 665                 670

Val Lys Asp Asn Arg Ser Leu His Asp Val Ser Asp Thr Leu Glu Pro
            675                 680                 685

Ser Asn Lys Thr Val Glu Lys Thr Ala Asp Val Lys Gln Val Asp
        690                 695                 700

Val Ala Gly Pro Asp Ala Pro Ser Thr Asp Ser Asn Gly Ala Ala Pro
705                 710                 715                 720

Glu Lys Lys Lys Lys Ala His Arg Gly Arg Arg Gly Val Lys His
                725                 730                 735

Arg Lys Gly Arg Pro Thr Asp Gly Ser Gln Ser His Gly Asn Asp Pro
            740                 745                 750

Ala Leu Thr Thr Val Asp Glu Ala Val Ser Asn Ala Lys Lys Leu Gly
        755                 760                 765

Asp Arg Pro Ser Leu Glu Pro Asp Val Met Thr Ile Tyr Asn Asp Met
    770                 775                 780

Gln Ala Val Thr Gly Ser Val Ile Ser Met Gly Asn Ile Glu Val Asp
785                 790                 795                 800

Thr Asp Val Glu Leu Gly Met Gly Ser Asn Gly Thr Val Phe Ala
                805                 810                 815

Gly Arg Phe Asp Gly Arg Asp Val Ala Val Lys Arg Met Thr Ile Gln
            820                 825                 830

Phe Tyr Asp Ile Ala Thr Arg Glu Thr Lys Leu Leu Arg Glu Ser Asp
        835                 840                 845

Asp His Pro Asn Val Ile Arg Tyr Tyr Ser Gln Val Gln Arg Gly Asp
    850                 855                 860

Phe Leu Tyr Ile Ala Leu Glu Arg Cys Ala Ala Ser Leu Ala Asp Val
865                 870                 875                 880

Ile Glu Lys Pro Tyr Ala Phe Gly Glu Leu Ala Lys Ala Gly Gln Lys
                885                 890                 895

Asp Leu Pro Gly Val Leu Tyr Gln Ile Thr Asn Gly Ile Ser His Leu
            900                 905                 910

His Ser Leu Arg Ile Val His Arg Asp Leu Lys Pro Gln Asn Ile Leu
        915                 920                 925

Val Asn Leu Asp Lys Asp Gly Arg Pro Arg Leu Leu Val Ser Asp Phe
    930                 935                 940

Gly Leu Cys Lys Lys Leu Glu Asp Arg Gln Ser Ser Phe Gly Ala Thr
945                 950                 955                 960

Thr Gly Arg Ala Ala Gly Thr Ser Gly Trp Arg Ala Pro Glu Leu Leu
                965                 970                 975

Leu Asp Asp Asp Gly Gln Asn Pro Ala Ala Ile Asp Ser Ser Thr His
            980                 985                 990

Ser Gly Ser His Thr Ile Leu Val Gly Asp Pro Asn Ser Leu Ser Asn
        995                1000                1005

Gly Gly Arg Ala Thr Arg Ala Ile Asp Ile Phe Ser Leu Gly Leu Val
    1010                1015                1020

Phe Phe Tyr Val Leu Thr Asn Gly Ser His Pro Phe Asp Cys Gly Asp
1025                1030                1035                1040

Arg Tyr Met Arg Glu Val Asn Ile Arg Lys Gly Asn Tyr Asn Leu Asp
                1045                1050                1055

Pro Leu Asp Ala Leu Gly Asp Phe Ala Tyr Glu Ala Lys Asp Leu Ile
            1060                1065                1070

Ala Ser Met Leu Gln Ala Ser Pro Lys Ala Arg Pro Asp Ser Arg Glu
        1075                1080                1085

```
Val Met Ala His Pro Phe Phe Trp Ser Pro Lys Lys Arg Leu Ala Phe
    1090                1095                1100

Leu Cys Asp Val Ser Asp Ser Leu Glu Lys Glu Val Arg Asp Pro Pro
1105                1110                1115                1120

Pro Ala Leu Val Glu Leu Glu Arg His Ala Pro Glu Val Ile Lys Gly
                1125                1130                1135

Asp Phe Leu Lys Val Leu Thr Arg Asp Phe Val Glu Ser Leu Gly Lys
            1140                1145                1150

Gln Arg Lys Tyr Thr Gly Asn Lys Leu Leu Asp Leu Leu Arg Ala Leu
        1155                1160                1165

Arg Asn Lys Arg Asn His Tyr Glu Asp Met Ser Asp Ser Leu Lys Arg
    1170                1175                1180

Ser Val Gly Ser Leu Pro Asp Gly Tyr Leu Ala Tyr Trp Thr Val Lys
1185                1190                1195                1200

Phe Pro Met Leu Leu Leu Thr Cys Trp Asn Val Val Tyr Asn Leu Glu
                1205                1210                1215

Trp Glu Lys Thr Asp Arg Phe Arg Glu Tyr Tyr Glu Pro Ala Gly Leu
            1220                1225                1230

<210> SEQ ID NO 15
<211> LENGTH: 1669
<212> TYPE: DNA
<213> ORGANISM: Aspergillus niger

<400> SEQUENCE: 15 cttttattg ttctatggtt cttaaggaca cctgtccttc ttggccctat ccttcttgtt      60
gtctggtaca cttgacccca ggcaccactt ggccaggcct ggccccccca gcttcccccg    120
ttatgacacg gtggcctgtg ttcctgtgac acgggcaagc agacgtcctc cacaagctgt    180
gtcgacctac atcaccgtcc tcccttgcag tgcggttaag ataaggctca tagtaaatcg    240
attgatccac aattaaagat caatcacctg tcacgcttga atgatggaa gaagcattct     300 ctccagtcga ctccctcgcc ggctccccga cgcctgagtt gccattgttg acagtgtccc    360
cggcggacac gtcgcttgat gactcgtcag tacaggcagg ggagaccaag gcggaagaga    420
agaagcctgt gaagaagaga aagtcatggg gccaggaatt gccagtcccg aagactaact    480
tgcccccaag gaaacgggcc aagactgaag atgagaaaga gcaacgtcgt atcgagcgcg    540
ttcttcgcaa tcgtgcggca gcacaaacat cacgcgagcg caagaggctc gaaatggaga    600
agttggaaaa tgagaagatt cagatggaac agcaaaacca gttccttctg caacgactat    660
cccagatgga agctgagaac aatcgcttaa ccaacaagt cgctcaacta tctgctgagg     720 tccgggctc ccgtggcaac actcccaagc ccggctcccc cgtctcagct tctcctaccc     780
taactcctac cctatttaaa caagaacgcg acgaaatccc tcttgaacgg attcctttcc    840
ccacacccct tatcaccgac tactccccta ccttgaggcc ttccactctg ctgagtcct    900 ccgacgtgac acaacatcct gcagcggtgt tgtgcgacct gcagtgtccg tcgctggact    960
cgaaggagaa ggaagtgccc tctctctctt tgacgtcggc tcaaacctg aacctcacgc     1020 tgccgatgat cttgcagctc ctctttctga cgatgacttc caccgcctat tcaacgttga    1080
ttcacccgtt gggtcagatt cttcagtcct gaagacggg ttcgcctttg acgttctcga     1140
cggaggagat ctatcagcat ttccatttga ttctatggtt gatttcgacc ccgaatctgt    1200
tggcttcgaa ggcatcgagc cgcccacgg tcttccggat gagacttctc gccagacttc    1260
tagcgtgcaa cccagccttg gcgcgtccac ttcgcgatgc gacgggcagg gcattgcagc    1320
```

```
tggctgttag cgagcagttt cgccaggag atgcatcggc tgtcgatggt aacggagtcc    1380
aatggagctg ggagtctttg ttgaccttgg cgtggacgat agacctactc gaacagccgg    1440
gacgacgcaa acgaatcttg agcggtttga atcagcgaa actggacgg cgaagtaata     1500 ttggcaagtc tcaaaggagt acacggagtt catggagttc acgaagcacc caagaggcgt    1560
tgacgtctct ccttatgggc aagcatagtt gaggttccgg ctgtaaatta tcataaatcc    1620
ttataatttt attctagatt tcaatacagc agttgattgt ctgctcatc               1669
```

<210> SEQ ID NO 16
<211> LENGTH: 386
<212> TYPE: PRT
<213> ORGANISM: Aspergillus niger

<400> SEQUENCE: 16

```
Met Val Leu Lys Asp Thr Cys Pro Ser Trp Pro Tyr Pro Ser Cys Cys
  1               5                  10                  15

Leu Val His Leu Thr Pro Gly Thr Thr Trp Pro Gly Leu Ala Pro Pro
             20                  25                  30

Ala Ser Pro Val Met Thr Arg Trp Pro Val Phe Leu Met Met Glu Glu
         35                  40                  45

Ala Phe Ser Pro Val Asp Ser Leu Ala Gly Ser Pro Thr Pro Glu Leu
     50                  55                  60

Pro Leu Leu Thr Val Ser Pro Ala Asp Thr Ser Leu Asp Asp Ser Ser
 65                  70                  75                  80

Val Gln Ala Gly Glu Thr Lys Ala Glu Lys Lys Pro Val Lys Lys
                 85                  90                  95

Arg Lys Ser Trp Gly Gln Glu Leu Pro Val Pro Lys Thr Asn Leu Pro
            100                 105                 110

Pro Arg Lys Arg Ala Lys Thr Glu Asp Glu Lys Glu Gln Arg Arg Ile
        115                 120                 125

Glu Arg Val Leu Arg Asn Arg Ala Ala Ala Gln Thr Ser Arg Glu Arg
    130                 135                 140

Lys Arg Leu Glu Met Glu Lys Leu Glu Asn Glu Lys Ile Gln Met Glu
145                 150                 155                 160

Gln Gln Asn Gln Phe Leu Leu Gln Arg Leu Ser Gln Met Glu Ala Glu
                165                 170                 175

Asn Asn Arg Leu Asn Gln Val Ala Gln Leu Ser Ala Glu Val Arg
            180                 185                 190

Gly Ser Arg Gly Asn Thr Pro Lys Pro Gly Ser Pro Val Ser Ala Ser
        195                 200                 205

Pro Thr Leu Thr Pro Thr Leu Phe Lys Gln Glu Arg Asp Glu Ile Pro
    210                 215                 220

Leu Glu Arg Ile Pro Phe Pro Thr Pro Ser Ile Thr Asp Tyr Ser Pro
225                 230                 235                 240

Thr Leu Arg Pro Ser Thr Leu Ala Glu Ser Ser Asp Val Thr Gln His
                245                 250                 255

Pro Ala Val Ser Val Ala Gly Leu Glu Gly Glu Gly Ser Ala Leu Ser
            260                 265                 270

Leu Phe Asp Val Gly Ser Asn Pro Glu Pro His Ala Ala Asp Asp Leu
        275                 280                 285

Ala Ala Pro Leu Ser Asp Asp Asp Phe His Arg Leu Phe Asn Val Asp
    290                 295                 300

Ser Pro Val Gly Ser Asp Ser Val Leu Glu Asp Gly Phe Ala Phe
305                 310                 315                 320
```

-continued

```
Asp Val Leu Asp Gly Gly Asp Leu Ser Ala Phe Pro Phe Asp Ser Met
            325                 330                 335

Val Asp Phe Asp Pro Glu Ser Val Gly Phe Glu Gly Ile Glu Pro Pro
        340                 345                 350

His Gly Leu Pro Asp Glu Thr Ser Arg Gln Thr Ser Val Gln Pro
            355                 360                 365

Ser Leu Gly Ala Ser Thr Ser Arg Cys Asp Gly Gln Gly Ile Ala Ala
        370                 375                 380

Gly Cys
385

<210> SEQ ID NO 17
<211> LENGTH: 20
<212> TYPE: DNA
<213> ORGANISM: Aspergillus niger

<400> SEQUENCE: 17
cggtgttgtg cgacctgcag                                              20

<210> SEQ ID NO 18
<211> LENGTH: 44
<212> TYPE: PRT
<213> ORGANISM: Aspergillus niger

<400> SEQUENCE: 18

Met Val Leu Lys Asp Thr Cys Pro Ser Trp Pro Tyr Pro Ser Cys Cys
1               5                   10                  15

Leu Val His Leu Thr Pro Gly Thr Thr Trp Pro Gly Leu Ala Pro Pro
            20                  25                  30

Ala Ser Pro Val Met Thr Arg Trp Pro Val Phe Leu
        35                  40

<210> SEQ ID NO 19
<211> LENGTH: 342
<212> TYPE: PRT
<213> ORGANISM: Aspergillus niger

<400> SEQUENCE: 19

Met Met Glu Glu Ala Phe Ser Pro Val Asp Ser Leu Ala Gly Ser Pro
1               5                   10                  15

Thr Pro Glu Leu Pro Leu Leu Thr Val Ser Pro Ala Asp Thr Ser Leu
            20                  25                  30

Asp Asp Ser Ser Val Gln Ala Gly Glu Thr Lys Ala Glu Glu Lys Lys
        35                  40                  45

Pro Val Lys Lys Arg Lys Ser Trp Gly Gln Glu Leu Pro Val Pro Lys
    50                  55                  60

Thr Asn Leu Pro Pro Arg Lys Arg Ala Lys Thr Glu Asp Glu Lys Glu
65                  70                  75                  80

Gln Arg Arg Ile Glu Arg Val Leu Arg Asn Arg Ala Ala Ala Gln Thr
                85                  90                  95

Ser Arg Glu Arg Lys Arg Leu Glu Met Glu Lys Leu Glu Asn Glu Lys
            100                 105                 110

Ile Gln Met Glu Gln Gln Asn Gln Phe Leu Leu Gln Arg Leu Ser Gln
        115                 120                 125

Met Glu Ala Glu Asn Asn Arg Leu Asn Gln Gln Val Ala Gln Leu Ser
    130                 135                 140

Ala Glu Val Arg Gly Ser Arg Gly Asn Thr Pro Lys Pro Gly Ser Pro
145                 150                 155                 160
```

```
Val Ser Ala Ser Pro Thr Leu Thr Pro Thr Leu Phe Lys Gln Glu Arg
            165                 170                 175

Asp Glu Ile Pro Leu Glu Arg Ile Pro Phe Pro Thr Pro Ser Ile Thr
            180                 185                 190

Asp Tyr Ser Pro Thr Leu Arg Pro Ser Thr Leu Ala Glu Ser Ser Asp
            195                 200                 205

Val Thr Gln His Pro Ala Val Ser Val Ala Gly Leu Glu Gly Glu Gly
            210                 215                 220

Ser Ala Leu Ser Leu Phe Asp Val Gly Ser Asn Pro Glu Pro His Ala
225                 230                 235                 240

Ala Asp Asp Leu Ala Ala Pro Leu Ser Asp Asp Phe His Arg Leu
            245                 250                 255

Phe Asn Val Asp Ser Pro Val Gly Ser Asp Ser Ser Val Leu Glu Asp
            260                 265                 270

Gly Phe Ala Phe Asp Val Leu Asp Gly Gly Asp Leu Ser Ala Phe Pro
            275                 280                 285

Phe Asp Ser Met Val Asp Phe Asp Pro Glu Ser Val Gly Phe Glu Gly
            290                 295                 300

Ile Glu Pro Pro His Gly Leu Pro Asp Glu Thr Ser Arg Gln Thr Ser
305                 310                 315                 320

Ser Val Gln Pro Ser Leu Gly Ala Ser Thr Ser Arg Cys Asp Gly Gln
            325                 330                 335

Gly Ile Ala Ala Gly Cys
            340

<210> SEQ ID NO 20
<211> LENGTH: 36
<212> TYPE: DNA
<213> ORGANISM: Artificial Sequence
<220> FEATURE:
<223> OTHER INFORMATION: primer

<400> SEQUENCE: 20
atcgcaggat cccacctac gacaacaacc gccact                                 36

<210> SEQ ID NO 21
<211> LENGTH: 36
<212> TYPE: DNA
<213> ORGANISM: Artificial Sequence
<220> FEATURE:
<223> OTHER INFORMATION: primer

<400> SEQUENCE: 21
tacagcggat ccctatggat tacgccaatt gtcaag                                36

<210> SEQ ID NO 22
<211> LENGTH: 72
<212> TYPE: DNA
<213> ORGANISM: Artificial Sequence
<220> FEATURE:
<223> OTHER INFORMATION: primer

<400> SEQUENCE: 22
ccacctacga caacaaccgc cactatggaa atgactgatt ttgaactact tgcctcgtcc      60
ccgccgggtc ac                                                          72

<210> SEQ ID NO 23
<211> LENGTH: 75
<212> TYPE: DNA
<213> ORGANISM: Artificial Sequence
<220> FEATURE:
```

<223> OTHER INFORMATION: primer

<400> SEQUENCE: 23
aattataccc tcttgcgatt gtcttcatga agtgatgaag aaatcattga cactggatgg    60
cggcgttagt atcga                                                    75

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
gccatccttg gtgactgagc c                                             21

<210> SEQ ID NO 25
<211> LENGTH: 24
<212> TYPE: DNA
<213> ORGANISM: Artificial Sequence
<220> FEATURE:
<223> OTHER INFORMATION: primer

<400> SEQUENCE: 25
caattgctcg ctcttacatt gaat                                          24

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
aattaaccct cactaaaggg                                               20

<210> SEQ ID NO 27
<211> LENGTH: 40
<212> TYPE: DNA
<213> ORGANISM: Artificial Sequence
<220> FEATURE:
<223> OTHER INFORMATION: primer

<400> SEQUENCE: 27
tggttgatga cgacgatgcg aacagtcatg acaggcaacg                         40

<210> SEQ ID NO 28
<211> LENGTH: 24
<212> TYPE: DNA
<213> ORGANISM: Artificial Sequence
<220> FEATURE:
<223> OTHER INFORMATION: HAC1-specific oligonucleotide

<400> SEQUENCE: 28
gggagacgac tgctggaacg ccat                                          24

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
ccccgagcag tccttgatgg                                               20

```
<210> SEQ ID NO 30
<211> LENGTH: 17
<212> TYPE: DNA
<213> ORGANISM: Artificial Sequence
<220> FEATURE:
<223> OTHER INFORMATION: primer

<400> SEQUENCE: 30
gtcgttgatg tcgaagt                                                    17

<210> SEQ ID NO 31
<211> LENGTH: 22
<212> TYPE: DNA
<213> ORGANISM: Artificial Sequence
<220> FEATURE:
<223> OTHER INFORMATION: primer

<400> SEQUENCE: 31
gtaatacgac tcactatagg gc                                              22

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
ttaggacaga ggccacggtg t                                               21

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
cccatccttg gtgactgagc c                                               21

<210> SEQ ID NO 34
<211> LENGTH: 21
<212> TYPE: DNA
<213> ORGANISM: Artificial Sequence
<220> FEATURE:
<223> OTHER INFORMATION: primer

<400> SEQUENCE: 34
aagagtcggt gtcagagttg g                                               21

<210> SEQ ID NO 35
<211> LENGTH: 72
<212> TYPE: DNA
<213> ORGANISM: Artificial Sequence
<220> FEATURE:
<223> OTHER INFORMATION: primer

<400> SEQUENCE: 35
attaatattt tagcactttg aaaaatgcgt ctacttcgaa gaaacatgct tgcctcgtcc     60
ccgccgggtc ac                                                         72

<210> SEQ ID NO 36
<211> LENGTH: 75
<212> TYPE: DNA
<213> ORGANISM: Artificial Sequence
<220> FEATURE:
```

<223> OTHER INFORMATION: primer

<400> SEQUENCE: 36
aagcagaggg gcatgaacat gttatgaata caaaaattca cgtaaaatgt cgacactgga    60
tggcggcgtt agtat                                                    75

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
ccgcaacacg acacggcagg caac                                          24

<210> SEQ ID NO 38
<211> LENGTH: 21
<212> TYPE: DNA
<213> ORGANISM: Artificial Sequence
<220> FEATURE:
<223> OTHER INFORMATION: primer

<400> SEQUENCE: 38
ctaggtagac gttgtatttt g                                             21

<210> SEQ ID NO 39
<211> LENGTH: 36
<212> TYPE: DNA
<213> ORGANISM: Artificial Sequence
<220> FEATURE:
<223> OTHER INFORMATION: primer

<400> SEQUENCE: 39
tcgaacggat ccgaaaagaa gcccgtcaag aagagg                             36

<210> SEQ ID NO 40
<211> LENGTH: 39
<212> TYPE: DNA
<213> ORGANISM: Artificial Sequence
<220> FEATURE:
<223> OTHER INFORMATION: primer

<400> SEQUENCE: 40
atcgcaggat ccctaggttt ggccatcccg cgagccaaa                          39

<210> SEQ ID NO 41
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 41
cggctgaacc agcgcggcag ccagatgtgg ccaaaggg                           38

<210> SEQ ID NO 42
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 42
ggtacctgct aaccagcgcg gcatgattca ac                                 32

```
<210> SEQ ID NO 43
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 43
ggatcttgca tagccagatg tggcctcgat tgact                               35

<210> SEQ ID NO 44
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 44
ggattagaaa acgccaacgt gtccataacg gtc                                 33

<210> SEQ ID NO 45
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 45
gggcgtggag aagcgagaag tggcctcttc ttctcc                              36

<210> SEQ ID NO 46
<211> LENGTH: 11
<212> TYPE: DNA
<213> ORGANISM: Artificial Sequence
<220> FEATURE:
<223> OTHER INFORMATION: binding consensus sequence
<220> FEATURE:
<221> NAME/KEY: misc_feature
<222> LOCATION: (1)...(11)
<223> OTHER INFORMATION: n = AW or C

<400> SEQUENCE: 46
gcsarngtgk c                                                         11

<210> SEQ ID NO 47
<211> LENGTH: 21
<212> TYPE: DNA
<213> ORGANISM: Artificial Sequence
<220> FEATURE:
<223> OTHER INFORMATION: primer

<400> SEQUENCE: 47
gtggtaatat tacctttaca g                                              21

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
caatttcaat acgggtggac                                                20

<210> SEQ ID NO 49
<211> LENGTH: 20
<212> TYPE: DNA
```

```
<213> ORGANISM: Artificial Sequence
<220> FEATURE:
<223> OTHER INFORMATION: primer

<400> SEQUENCE: 49
tgtcatcact gctccatctt                                               20

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
ttaagccttg gcaacatatt                                               20

<210> SEQ ID NO 51
<211> LENGTH: 21
<212> TYPE: DNA
<213> ORGANISM: Artificial Sequence
<220> FEATURE:
<223> OTHER INFORMATION: primer

<400> SEQUENCE: 51
ttgaacagca gatcgttact g                                             21

<210> SEQ ID NO 52
<211> LENGTH: 21
<212> TYPE: DNA
<213> ORGANISM: Artificial Sequence
<220> FEATURE:
<223> OTHER INFORMATION: primer

<400> SEQUENCE: 52
tataaagttc gtcaatagtg g                                             21

<210> SEQ ID NO 53
<211> LENGTH: 21
<212> TYPE: DNA
<213> ORGANISM: Artificial Sequence
<220> FEATURE:
<223> OTHER INFORMATION: primer

<400> SEQUENCE: 53
cggaggcaag agtcatagac g                                             21

<210> SEQ ID NO 54
<211> LENGTH: 23
<212> TYPE: DNA
<213> ORGANISM: Artificial Sequence
<220> FEATURE:
<223> OTHER INFORMATION: primer

<400> SEQUENCE: 54
caatatattt ctgaaccagt acg                                           23

<210> SEQ ID NO 55
<211> LENGTH: 45
<212> TYPE: RNA
<213> ORGANISM: Trichoderma reesei

<400> SEQUENCE: 55
acugauucga cacaacgucc ugcagagaug uugugcgacc cgcag                   45

<210> SEQ ID NO 56
```

```
<211> LENGTH: 45
<212> TYPE: RNA
<213> ORGANISM: Aspergillus nidulans

<400> SEQUENCE: 56
cccgauuuga cacaacaucc ugcagcgaug uugugcgacc ugcag          45

<210> SEQ ID NO 57
<211> LENGTH: 28
<212> TYPE: RNA
<213> ORGANISM: Saccharomyces cerevisiae

<400> SEQUENCE: 57
ccuuguacug uccgaagcgc agucaggu                              28

<210> SEQ ID NO 58
<211> LENGTH: 60
<212> TYPE: DNA
<213> ORGANISM: Trichoderma reesei

<400> SEQUENCE: 58
ccactgattc gacacaacgt cctgcagaga tgttgtgcga cccgcagtgt caatcggtgg   60

<210> SEQ ID NO 59
<211> LENGTH: 60
<212> TYPE: DNA
<213> ORGANISM: Aspergillus nidulans

<400> SEQUENCE: 59
cccccgattt gacacaacat cctgcagcga tgttgtgcga cctgcagtgt cagtcggcgg   60

<210> SEQ ID NO 60
<211> LENGTH: 68
<212> TYPE: PRT
<213> ORGANISM: Saccharomyces cerevisiae

<400> SEQUENCE: 60

Lys Ser Thr Leu Pro Pro Arg Lys Arg Ala Lys Thr Lys Glu Glu Lys
 1               5                  10                  15

Glu Gln Arg Arg Ile Glu Arg Ile Leu Arg Asn Arg Arg Ala Ala His
             20                  25                  30

Gln Ser Arg Glu Lys Lys Arg Leu His Leu Gln Tyr Leu Glu Arg Lys
         35                  40                  45

Cys Ser Leu Leu Glu Asn Leu Leu Asn Ser Val Asn Leu Glu Lys Leu
     50                  55                  60

Ala Asp His Glu
65

<210> SEQ ID NO 61
<211> LENGTH: 12
<212> TYPE: DNA
<213> ORGANISM: Trichoderma reesei

<400> SEQUENCE: 61
gccagatgtg gc                                                12

<210> SEQ ID NO 62
<211> LENGTH: 11
<212> TYPE: DNA
<213> ORGANISM: Trichoderma reesei

<400> SEQUENCE: 62
gccaacgtgt c                                                 11
```

```
<210> SEQ ID NO 63
<211> LENGTH: 12
<212> TYPE: DNA
<213> ORGANISM: Trichoderma reesei

<400> SEQUENCE: 63
gcgagaagtg gc                                                          12
```